United States Patent
Chen et al.

(10) Patent No.: US 9,987,280 B2
(45) Date of Patent: Jun. 5, 2018

(54) SIRT1 INHIBITORS AND STEM CELL REJUVENATION

(71) Applicant: City of Hope, Duarte, CA (US)

(72) Inventors: WenYong Chen, Temple, CA (US); Zhiqiang Wang, Covina, CA (US)

(73) Assignee: City of Hope, Duarte, CA (US)

( * ) Notice: Subject to any disclaimer, the term of this patent is extended or adjusted under 35 U.S.C. 154(b) by 0 days. days.

(21) Appl. No.: 14/456,484

(22) Filed: Aug. 11, 2014

(65) Prior Publication Data

US 2015/0044184 A1 Feb. 12, 2015

Related U.S. Application Data

(60) Provisional application No. 61/864,370, filed on Aug. 9, 2013.

(51) Int. Cl.
| | | |
|---|---|---|
| *A61K 31/17* | (2006.01) | |
| *A61K 31/513* | (2006.01) | |
| *A61K 35/28* | (2015.01) | |
| *A61K 35/12* | (2015.01) | |

(52) U.S. Cl.
CPC ............ *A61K 31/513* (2013.01); *A61K 31/17* (2013.01); *A61K 35/28* (2013.01); *A61K 2035/124* (2013.01)

(58) Field of Classification Search
None
See application file for complete search history.

(56) References Cited

U.S. PATENT DOCUMENTS

2010/0137345 A1\* 6/2010 Leo ...................... A61K 31/166
514/274
2011/0092695 A1 4/2011 Chen et al.
2011/0301163 A1\* 12/2011 Liu ........................ A61K 31/47
514/235.2

OTHER PUBLICATIONS

Kaur, Maninderjeet; et al; "Suramin's development: what did we learn?" Investigational New Drugs, 20, 209-219, 2002.*
Singh, Satyendra K; et al; "Sirt1 ablation promotes stress-induced loss of epigenetic and genomic hematopoietic stem and progenitor cell maintenance" Journal of Experimental Medicine, 21-, 987-1001, 2013.*
Ng, WL; et al; "Lymphopenia at presentation is associated with increased risk of infections in patient with systemic lupus erythematosus" Quarterly Journal of Medicine, 99,37-47, 2006.*
Makipour, Sasan; et al; "Unexplained Anemia in the Elderly" Seminar is Hematology, 45, 250-254, 2008.*
Beghe, C. et al. (Apr. 5, 2004). "Prevalence and outcomes of anemia in geriatrics: a systematic review of the literature," *Am J Med* 116 Suppl 7A:3S-10S.
Chen, W.Y. et al. (Nov. 4, 2005). "Tumor suppressor HIC1 directly regulates SIRT1 to modulate p53-dependent DNA-damage responses," *Cell* 123:437-448.
Chen, C. et al. (Nov. 24, 2009). "mTOR regulation and therapeutic rejuvenation of aging hematopoietic stem cells," *Sci Signal* 2(98):ra75.
Cho, R.H. et al. (Jun. 15, 2008, e-published Apr. 15, 2008). "A new mechanism for the aging of hematopoietic stem cells: aging changes the clonal composition of the stem cell compartment but not individual stem cells," *Blood* 111(12):5553-5561.
Houtkooper, R.H. et al. (Mar. 7, 2012). "Sirtuins as regulators of metabolism and healthspan," *Nat Rev Mol Cell Bio* 13(4):225-238.
Lain, S. et al. (May 2008). "Discovery, in vivo activity, and mechanism of action of a small-molecule p53 activator," *Cancer Cell* 13(5):454-463.
Lichtman, M.A. (Apr. 2004). "The relationship of patient age to the pathobiology of the clonal myeloid diseases," *Semin Oncol* 31(2):185-197.
Linton, P.J. et al. (Feb. 2004). "Age-related changes in lymphocyte development and function," *Nat Immunol* 5(2):133-139.
Oberdoerffer, P. et al. (Nov. 28, 2008). "SIRT1 redistribution on chromatin promotes genomic stability but alters gene expression during aging," *Cell* 135(5):907-918.
Rossi, D.J. et al. (Jun. 28, 2005, e-published Jun. 20, 2005). "Cell intrinsic alterations underlie hematopoietic stem cell aging," *Proc Natl Acad Sci U S A* 102(26):9194-9199.
Rossi, D.J. et al. (Feb. 22, 2008). "Stems cells and the pathways to aging and cancer," *Cell* 132(4):681-696.
Saunders, L.R. et al. (Aug. 13, 2007). "Sirtuins: critical regulators at the crossroads between cancer and aging," *Oncogene* 26(37):5489-5504.
Siegel, R. et al. (Jan. 2013, e-published Jan. 17, 2013). "Cancer statistics, 2013," *CA: A Cancer Journal for Clinicians* 63(1):11-30.
Wang, R.H. et al. (Oct. 7, 2008). "Impaired DNA damage response, genome instability, and tumorigenesis in SIRT1 mutant mice," *Cancer Cell* 14(4):312-323.
Yuan, H. et al. (Feb. 23, 2012, e-published Dec. 29, 2011). "Activation of stress response gene SIRT1 by BCR-ABL promotes leukemogenesis," *Blood* 119(8):1904-1914.

\* cited by examiner

*Primary Examiner* — David W Berke-Schlessel
(74) *Attorney, Agent, or Firm* — Mintz Levin Cohn Ferris Glovsky and Popeo, P.C.

(57) ABSTRACT

Provided herein are, inter alia, methods and compositions for treating or preventing diseases using SIRT1 inhibitors. The methods provided herein are particularly useful for treating or preventing age-related hematological diseases as well as cancerous hematological diseases. Further provided herein are hematopoietic cells useful for treating or preventing hematological diseases.

11 Claims, 40 Drawing Sheets

| Sirtuin protein and catalytic domain | Enzymatic Activities | Primary Localization |
|---|---|---|
| SIRT1  254–495  747 | Deacetylase | Nucleus |
| SIRT2  40–294  352 | Deacetylase | Cytosol |
| SIRT3  137–373  399 | Deacetylase | Mitochondria |
| SIRT4  47–308  314 | ART | Mitochondria |
| SIRT5  51–301  310 | Deacetylase & Deacylase | Mitochondria |
| SIRT6  45–257  355 | Deacetylase & ART | Nucleus |
| SIRT7  100–314  410 | Deacetylase | Nucleolus |

| Gene Symbol | Gene Title | p-value (Young WT vs. Old WT) | Fold-Change (Young WT vs. Old WT) | p-value (Old KO vs. Old WT) | Fold-Change (Old KO vs. Old WT) |
|---|---|---|---|---|---|
| Speg | SPEG complex locus | 0.002536 | -6.07078 | 0.00316047 | -7.24551 |
| Trim26 | tripartite motif-containing 26 | 0.00247612 | -5.26186 | 0.00460583 | -5.26698 |
| Prr15 | proline rich 15 | 0.0010643 | -5.12808 | 0.000754797 | -7.64357 |
| --- | --- | 0.0300757 | -4.6361 | 0.0423458 | -4.94697 |
| Rian | RNA imprinted and accumulated in nucleus | 0.0156153 | -4.61418 | 0.0320326 | -4.24906 |
| Exosc2 | Exosome component 2 | 0.00112441 | -3.90898 | 0.00263926 | -3.67495 |
| --- | --- | 0.00211727 | -3.75924 | 0.00537751 | -3.43125 |
| --- | --- | 0.00748311 | -3.66969 | 0.0257316 | -2.96624 |
| Polr3f | polymerase (RNA) III (DNA directed) polypeptide F | 0.0062971 | -3.62114 | 0.0126632 | -3.48675 |
| LOC10050362 | hypothetical LOC100503627 | 0.00430602 | -3.46757 | 0.0074835 | -3.51864 |

SIRT1 INHIBITORS AND STEM CELL REJUVENATION

CROSS-REFERENCE TO RELATED APPLICATIONS

This application claims the benefit of U.S. Provisional Application No. 61/864,370 filed Aug. 9, 2013, which is hereby incorporated in its entirety and for all purposes.

STATEMENT AS TO RIGHTS TO INVENTIONS MADE UNDER FEDERALLY SPONSORED RESEARCH AND DEVELOPMENT

This invention was made with government support under RO1 CA143421 awarded by the National Institutes of Health. The Government has certain rights in the invention.

BACKGROUND OF THE INVENTION

Mammalian aging is a multi-organ process characterized by loss of tissue regenerative potential. It has been increasingly recognized that tissue-specific stem cells may underlie the aging process, but the degree that they are involved may vary substantially between different tissues and should be carefully evaluated on a tissue-by-tissue basis. (Rossi, D. J. et al., Cell 132, 681-696 (2008)) Hematopoietic stem cells (HSCs) are the best characterized adult tissue stem cells. HSC aging contributes to several pathophysiological conditions in the elderly including the onset of anemia, (Beghe, C. et al., Am J Med 116 Suppl 7A, 3S-10S (2004).) the decline of immune competence, (Linton, P. J. & Dorshkind, Nat Immunol 5, 133-139 (2004)) and the increased incidence of hematological malignancies particularly myeloid leukemia. (Lichtman, M. A. & Rowe, J. M., Semin Oncol 31, 185-197 (2004)) Aging HSCs exhibit increased cell cycle entry and expansion of the HSC compartment along with a skewed differentiation program favoring myeloid lineage. (Morrison, S. J. et al., Nat Med 2, 1011-1016 (1996); Pang, W. W. et al., Proc Natl Acad Sci USA 108, 20012-20017 (2011)) Aging HSCs display an intrinsic transcriptome change, (Rossi, D. J. et al., Proc Natl Acad Sci USA 102, 9194-9199 (2005)) and the skewing of lineage potential is attributed to clonal expansion of myeloid-biased HSCs during aging. (Challen, G. A. et al., Cell stem cell 6, 265-278 (2010); Beerman, I. et al., Proc Natl Acad Sci USA 107, 5465-5470 (2010); Cho, R. H. et al., Blood 111, 5553-5561 (2008)) It has been postulated that aging is a consequence of life long exposure to free radical or oxidative stress, (Harman, D., J Gerontol 11, 298-300 (1956)) which causes cellular damage. Spontaneous DNA damage is indeed accumulated in aged HSCs and genome maintenance machineries including non-homologous end joining (NHEJ) repair are required for maintaining HSC functions during aging. (Rossi, D. J. et al., Nature 447, 725-729 (2007); Nijnik, A. et al., Nature 447, 686-690 (2007)) But, how self-renewal and lineage determination of HSCs during aging are molecularly controlled is poorly understood.

Sirtuins are a family of mammalian lysine modifying enzymes involved in regulating metabolism, aging and cancer. (Houtkooper, R. H. et al., Nat Rev Mol Cell Bio 13, 225-238 (2012); Saunders, L. R. et al., Oncogene 26, 5489-5504 (2007)) Sirtuins are homologues of yeast silent information regulator 2 (Sir2) that encodes a NAD-dependent histone deacetylase. (Imai, S. et al., Nature 403, 795-800 (2000)) Initial studies in lower organisms showed that increased Sir2 gene dosage is sufficient to extend lifespan, (Kaeberlein, M. et al., Genes Dev 13, 2570-2580 (1999); Tissenbaum, H. A. & Guarente, L., Nature 410, 227-230 (2001)) and that Sir2 is the major effector for caloric restriction (CR) or CR mimetics for increasing longevity. (Howitz, K. T. et al., Nature 425, 191-196 (2003); Wood, J. G. et al., Nature 430, 686-689 (2004)) Sirtuin 1 (SIRT1) shares the highest homology with yeast Sir2 and is the most extensively studied mammalian sirtuin. SIRT 1 is a stress response gene encoding a multi-functional protein deacetylase that regulates epigenetic gene silencing, DNA damage repair, cell survival under stress, and energy homeostasis. (Houtkooper, R. H. et al., Nat Rev Mol Cell Bio 13, 225-238 (2012); Saunders, L. R. et al., Oncogene 26, 5489-5504 (2007)) Over-expression of SIRT1 is shown to improve mouse aging but fails to increase lifespan, and noticeably, does not reduce age-dependent development of lymphoma and histiocytic lymphoma. (Herranz, D. et al., Nat Commun 1, 3 (2010))

There is a need in the art for methods and compostions of treating hematological diseases. Disclosed herein are methods of using SIRT1 inhibitors, which are surprisingly effective to prevent or treat age-related, cancerous or non-cancerous hematological disease, thereby curing these and other needs in the art.

BRIEF SUMMARY OF THE INVENTION

In one aspect, a method of treating or preventing a hematological disease in a subject in need thereof is provided. The method includes administering a therapeutically effective amount of a SIRT1 inhibitor to a subject, thereby treating or preventing a hematological disease in the subject, wherein the disease is not a cancerous hematological disease.

In another aspect, a method of increasing immune competence in a subject in need thereof is provided. The method includes administering a therapeutically effective amount of a SIRT1 inhibitor to a subject, thereby increasing immune competence in the subject.

In another aspect, a method of treating or preventing a hematological disease in a subject in need thereof is provided. The method includes isolating a hematopoietic stem cell (HSC) from a subject, thereby forming an isolated HSC. The isolated HSC is contacted with a SIRT1 inhibitor, thereby forming a rejuvenated HSC. The rejuvenated HSC is adminstered to the subject, thereby treating or preventing a hematological disease in the subject.

In another aspect, a method of forming a red blood cell is provided. The method includes contacting a hematopoietic stem cell (HSC) with a SIRT1 inhibitor, thereby forming a rejuvenated HSC. And the rejuvenated HSC is allowed to divide, thereby forming a red blood cell.

In another aspect, a hematopoietic stem cell (HSC) modified by an exogenous SIRT1 inhibitor is provided.

and blood (D) analyzed 5 month later. (E) SP cell analysis of reconstituted mice 5 month after transplantation.

Figure 2:
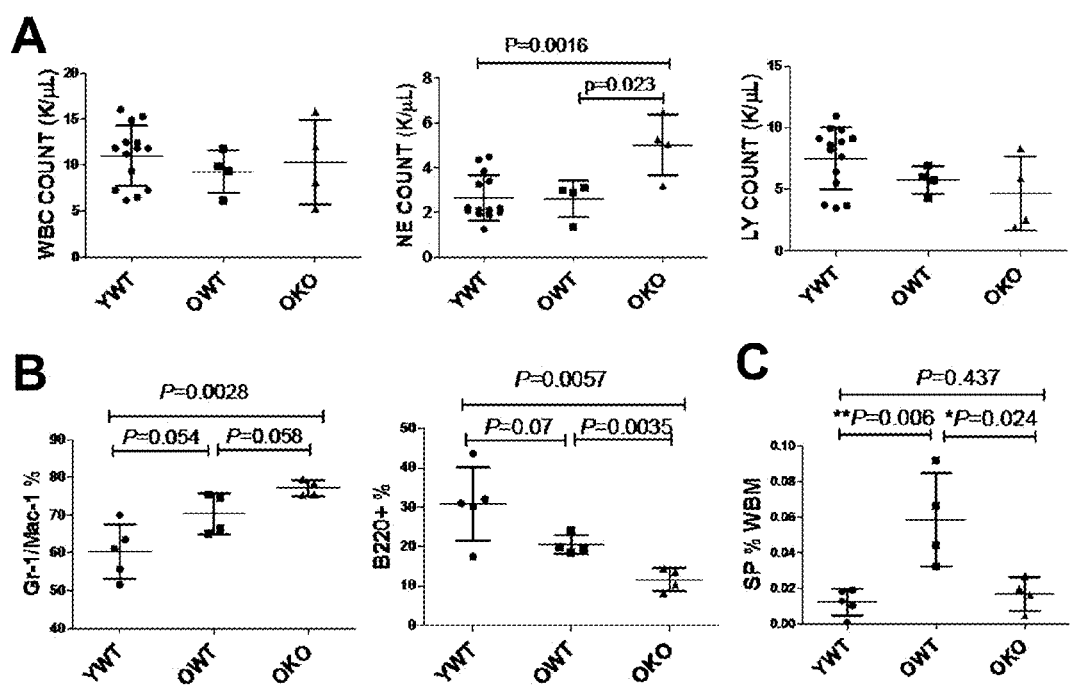

FIG. 2 SIRT1 knockout inhibited HSC expansion in aging BALB/c mice. (A) Comparison of blood cell counts of old wild type (OWT), old SIRT1$^{-/-}$ (OKO) and young wild type (YWT). Old mice were in 16-20 months, and YWT in 2 to 3 months. (B) Bone marrow lineage analysis of old versus young mice. (C) Bone marrow SP cell analysis of old versus young mice.

Figure 3:
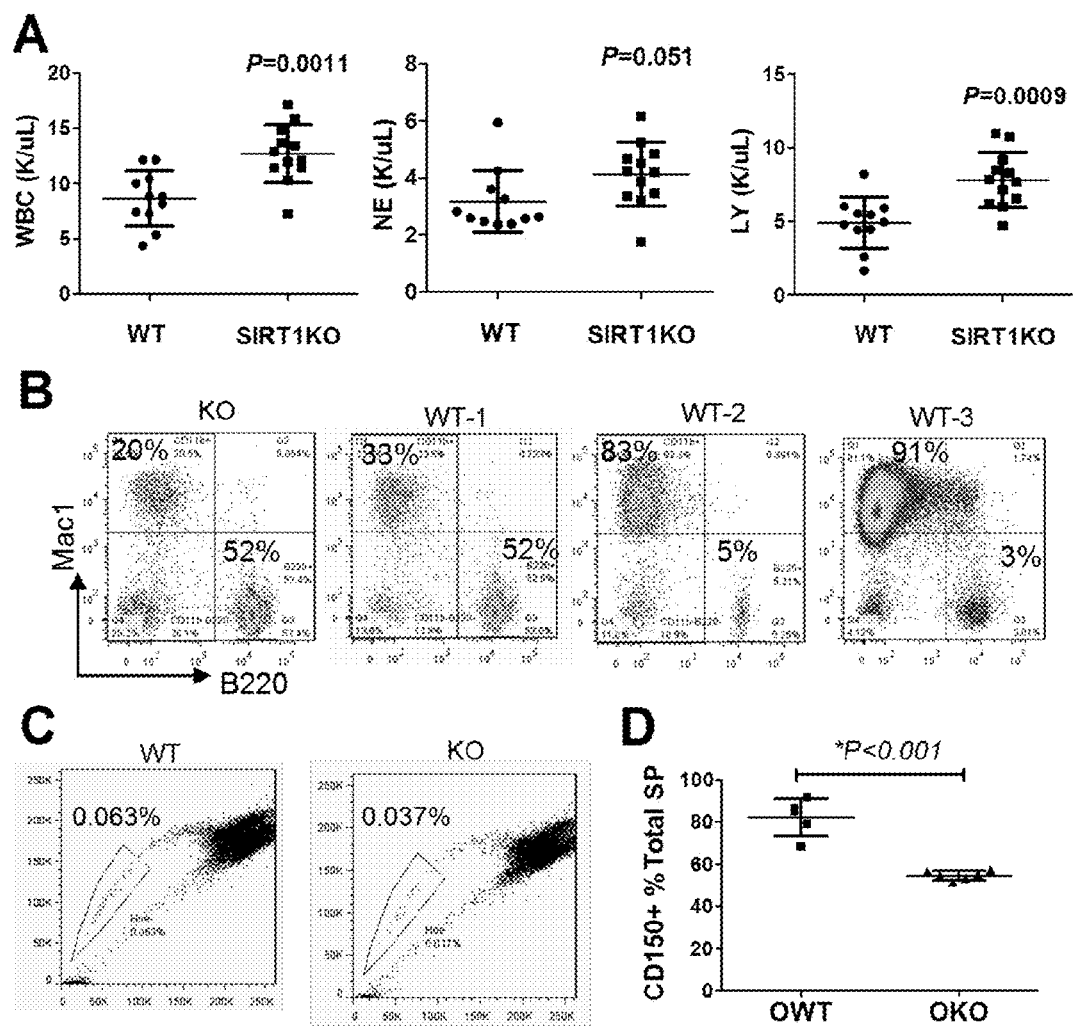

FIG. 3 SIRT1 knockout inhibited biased HSC differentiation in 1$^{st}$ BMT recipients. (A) Differential blood cell counts in 1$^{st}$ BMT recipients 8 month after transplantation with 14-month donor marrow (14-8 series). (B-D) Analysis of another BMT series 10 month after transplantation with 20 month old donor marrow (20-10 series). B, peripheral blood B220$^+$ vs Mac1$^+$ cells; C, bone marrow SP cell analysis; D, CD150 fraction of bone marrow SP cells.

Figure 4:
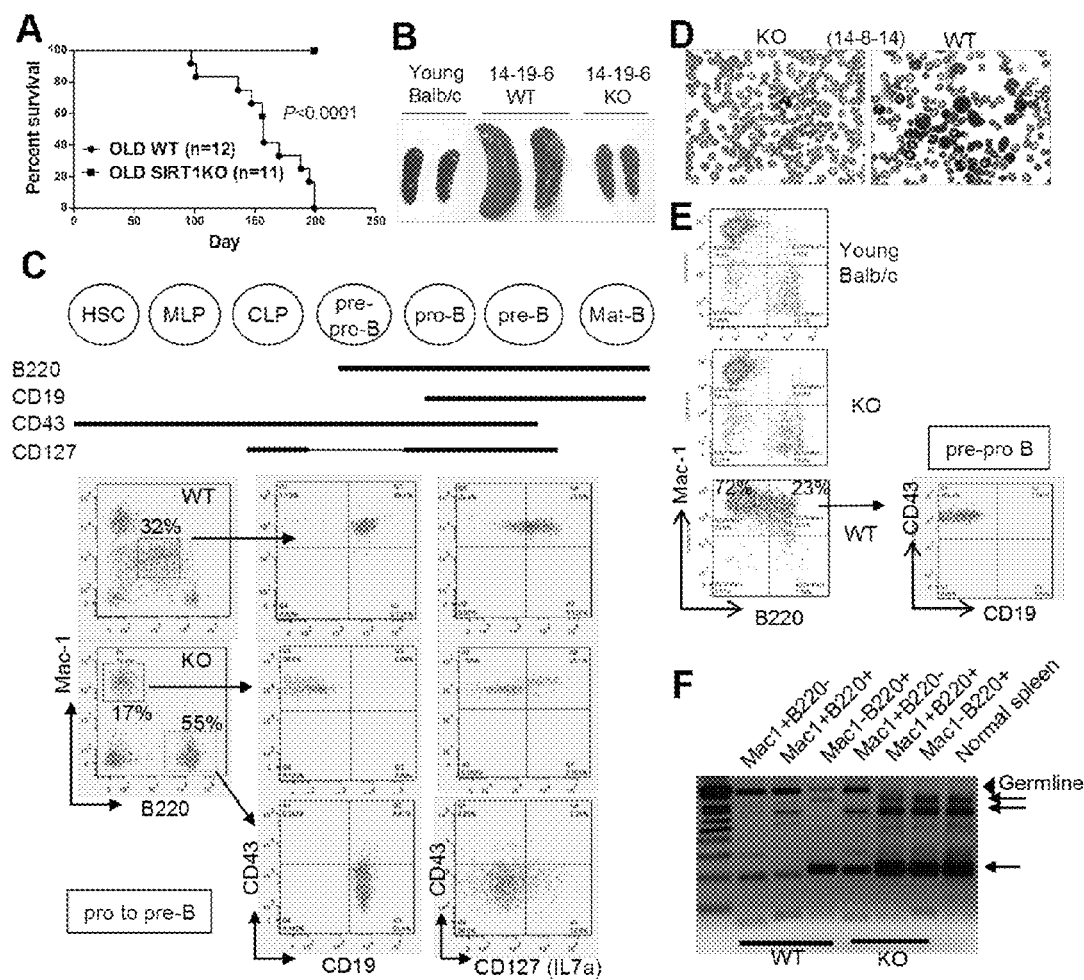

FIG. 4 SIRT1 knockout inhibited hematological malignancies in 2nd BMT recipients. (A) Survival curves of 2nd BMT recipients receiving marrow from 19 month old 1$^{st}$ BMT recipients with 14 month old original donors (14-19-Y series). (B) Splenomegaly in 14-19-6 BMT recipients with WT, but not SIRT1 knockout, cells. A lymphoma nodule on one WT spleen was obvious. (C) Immunotyping of blood immature cells in 14-19-4 BMT mice. Note the unusual immature cell population with intermediate B220 and Mac1 expression. Markers used for B-cell progenitor cells were drawn according to Hardy, R. R. Ann Rev Immunol 2001. (D) Blood smear of 14-8-14 series BMT mice. (E) Immunotyping of acute myeloid leukemia (AML) in 14-8-14 BMT mice. Note high percentage of B220$^+$Mac1$^+$ cells and absence of mature B cells in bone marrow of mice receiving WT cells. (F) V-D-J recombination assay of 14-8-14 AML cells. B220$^+$ Mac1$^+$ WT cells retained D-J germline allele.

Figure 5:
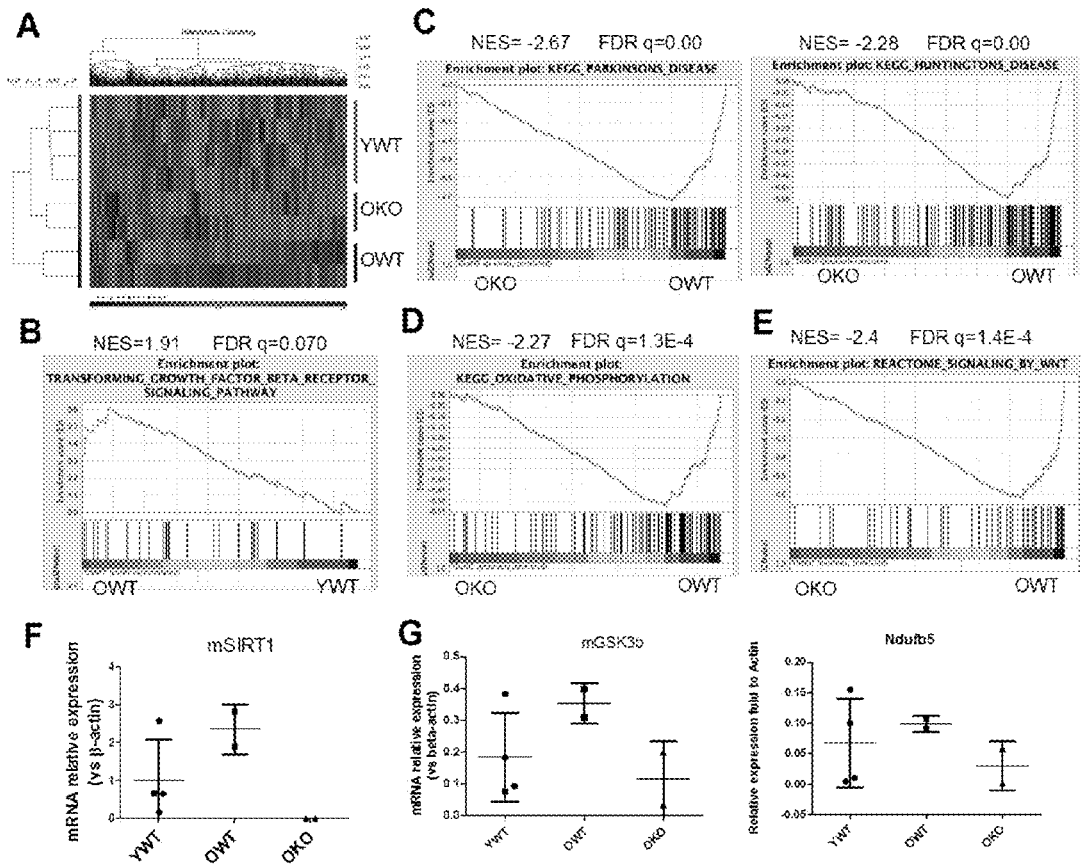

FIG. 5 Microarray gene expression analysis of SP HSCs. (A) Hierarchical clustering of gene expression data of sorted SP cells from YWT (10 weeks) vs old (16-20 months) WT or SIRT1 KO mice. (B) GSEA enrichment plot for TGF-β pathway in OWT vs YWT mice. (C-E) GSEA enrichment plots for Parkinson's and Huntington's diseases (C), oxidative phosphorylation (D) and WNT signaling pathway (E). (F,G) Real-time PCR confirmation of expression of SIRT1 (F) and selected genes, mGSK3b for WNT signaling pathway and Ndufb5 for oxidative phosphorylation (G).

Figure 6:
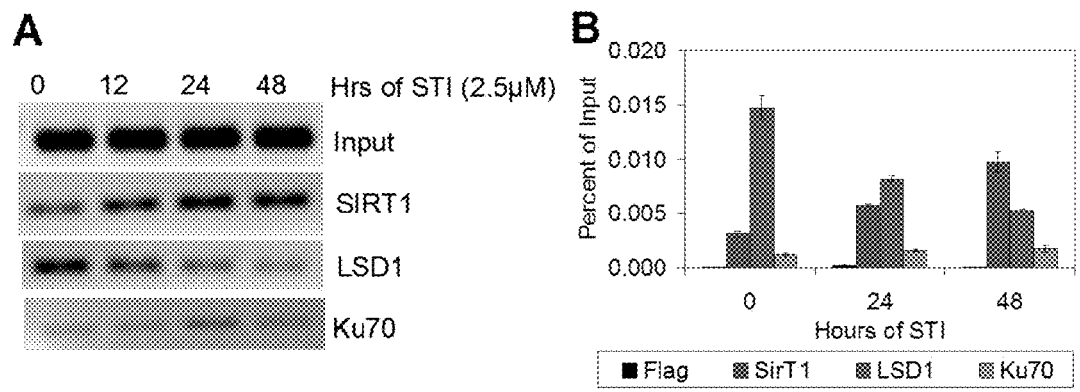

FIG. 6 Opposing recruitment of SIRT1 and LSD1 on the BCR-ABL locus ChIP assay with conventional PCR (A) and real-time PCR (B) were performed on chromatin-bound SIRT1, LSD1 and Ku70 on the ABL exon 5.

Figure 7:
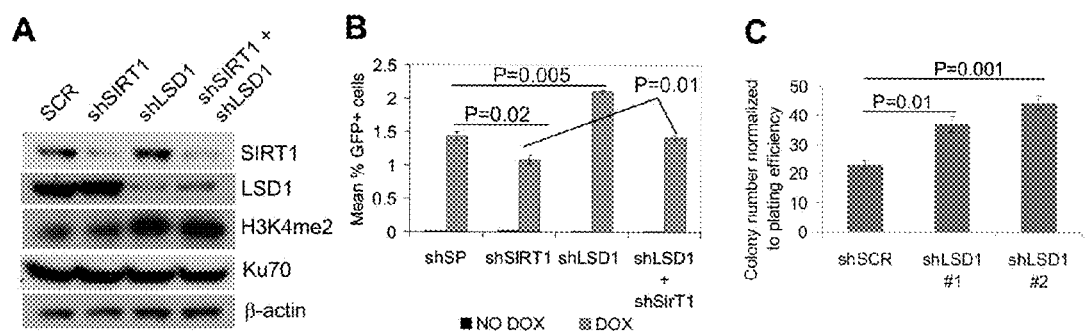

FIG. 7 Opposing roles of SIRT1 and LSD1 in DNA damage repair and BCR-ABL mutation acquisition (A) Western blot analysis of individual and double knockdown of SIRT1 and LSD1. SCR, scrambled shRNA. (B) Effects of SIRT1 and LSD1 knockdown on DNA damage repair. (C) Effect of LSD1 knockdown on formation of BCR-ABL mutant colonies.

Figure 8:
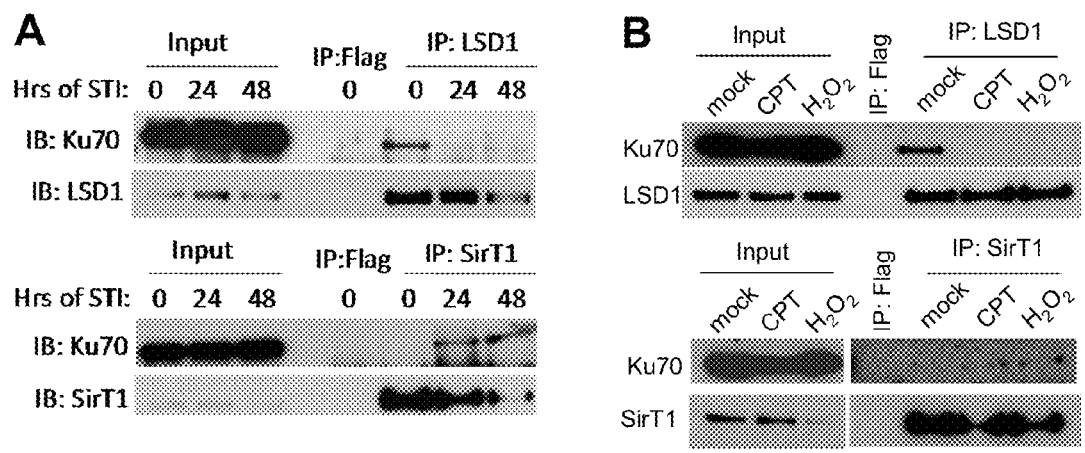

FIG. 8 Differential interaction of LSD1 and SIRT1 with Ku70 in response to stress. IP of LSD1 or SIRT1 was carried out in KCL-22 cells to detect their interaction with Ku70, respectively. (A) In the absence and presence of 2.5 μM imatinib (STI) for 24 and 48 h. (B) Without and with treatment of 1 mM H$_2$O$_2$ for 1 h and 0.25 μM camptothecin (CPT) for 12 h. Flag was used for IP control.

Figure 9:
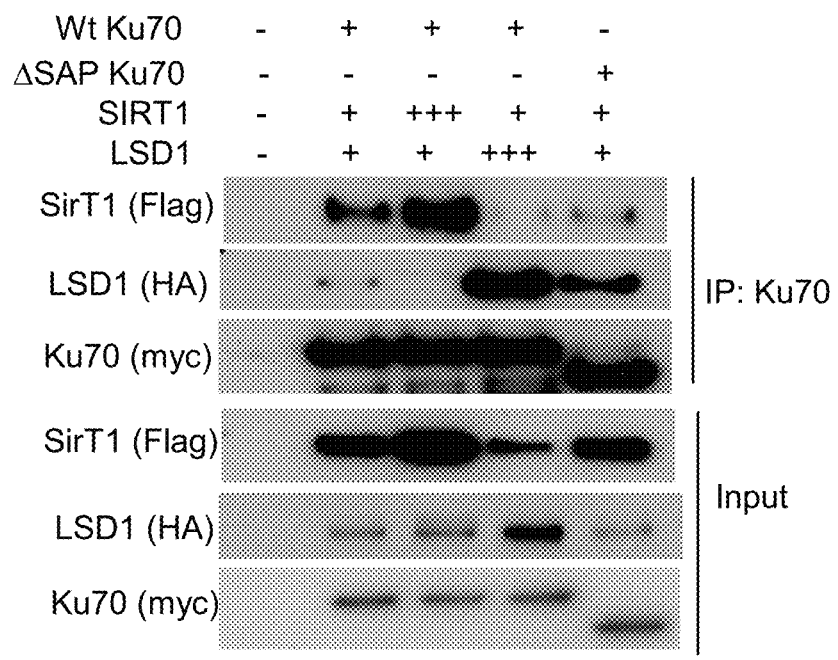

FIG. 9 Competitive binding of Ku70 by LSD1 and SIRT1 Flag-SIRT1, HA-LSD1 and Myc-Ku70 were expressed in 293 cells with different amount indicated. Ku70 was pulled down for detection of binding partners. ΔSAP Ku70 had enhanced LSD1 interaction shown in FIG. 10.

Figure 10:
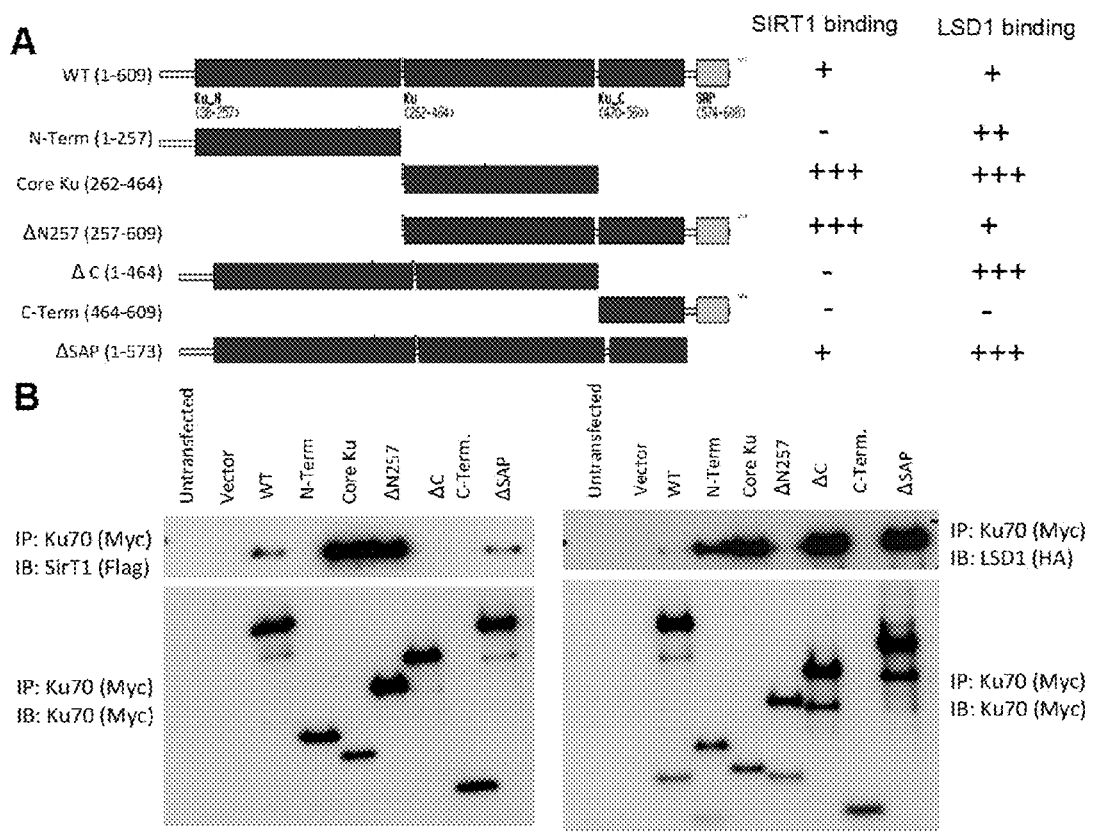

FIG. 10 Mapping Ku70 domains interacting with SIRT1 and LSD1 (A) Ku70 truncation constructs and summary of interaction. (B) Co-IP for interaction of Myc-tagged Ku70 constructs with Flag-tagged SIRT1 (left) or HA-tagged LSD1 (right) expressed in 293 cells.

Figure 11:
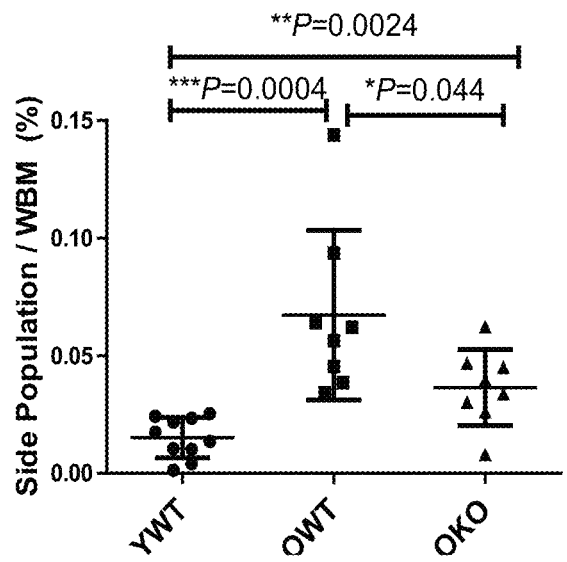

FIG. 11 SIRT1 knockout inhibited HSC expansion in aging BALB/c mice. Young wild type (YWT) for comparison.

Figure 12:
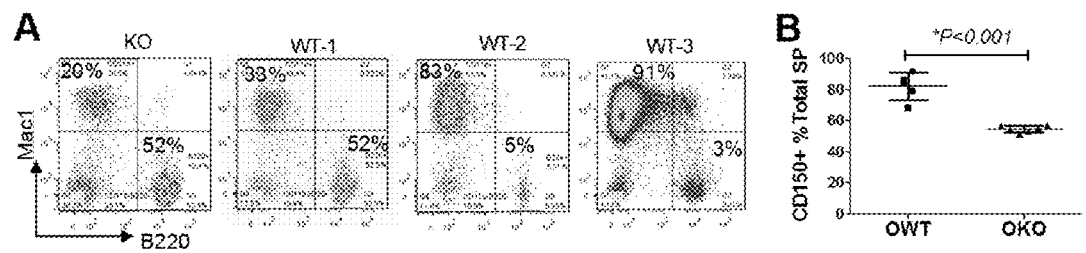

FIG. 12 SIRT1 knockout inhibited biased HSC differentiation in 1st BMT recipients. (A) Analysis of another BMT series 10 month after transplantation with 20 month old donor marrow (20-10 series). (B) CD150 fraction of bone marrow SP cells.

Figure 13:
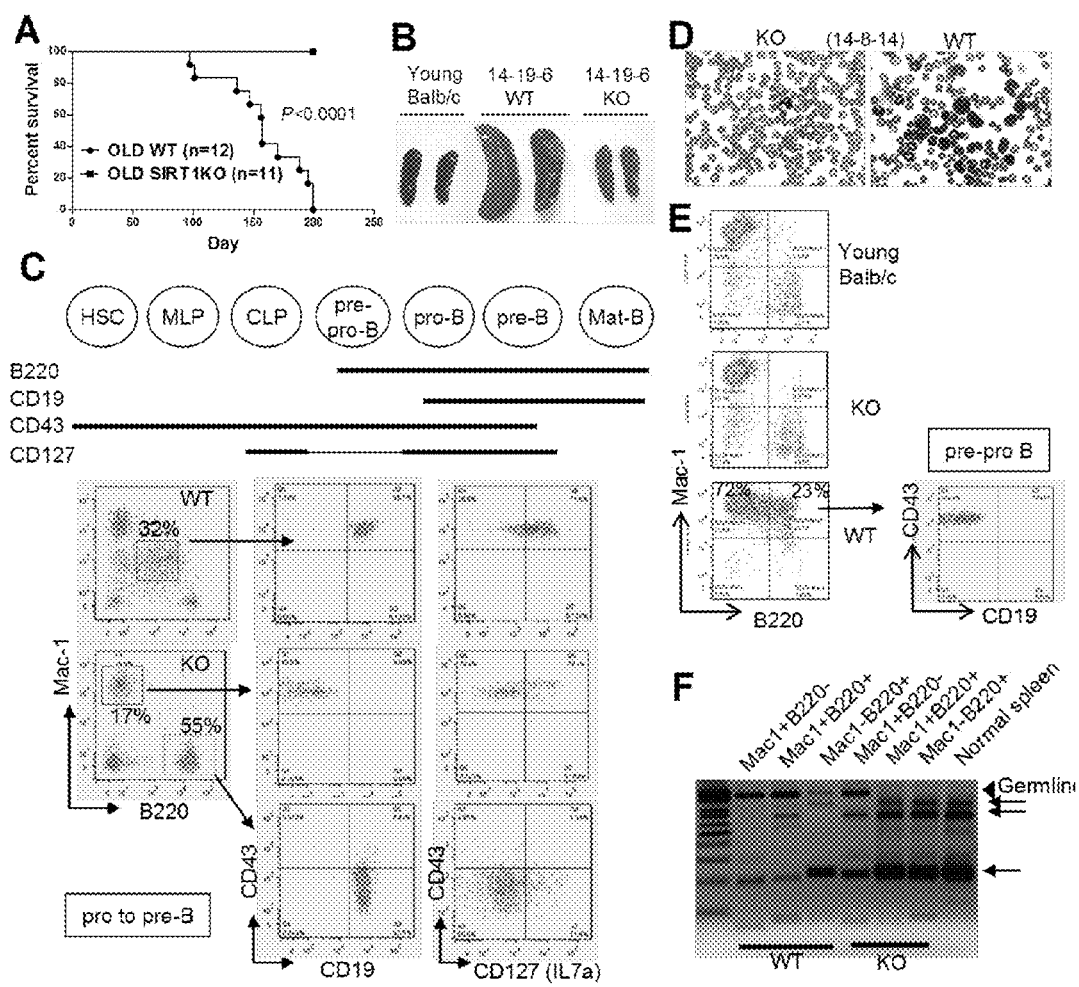

FIG. 13 SIRT 1 knockout inhibited hematological malignancies in 2$^{nd}$ BMT recipients. (A) Survival curves of 2$^{nd}$ BMT recipients receiving marrow from 19 month old 1$^{st}$ BMT recipients with 14 month old original donors (14-19-Y series). (B) Splenomegaly in 14-19-6 BMT recipients with WT, but not SIRT1 knockout cells. A lymphoma nodule on one WT spleen was obvious. (C) Immunotyping of blood immature cells in 14-19-4 BMT mice. Note the unusual immature cell population with intermediate B220 and Mac1 expression. Markers used for B-cell progenitor cells were drawn according to Hardy R. R. Ann Rev Immunol 2001. (D) Blood smear of 14-8-14 BMT mice. (E) Immunotyping of acute myeloid leukemia (AML) in 14-8-14 BMT mice. Note high percentage of B220+Mac1+ cells and absence of mature B cells in bone marrow of mice receiving WT cells. (F) V-D-J recombination assay of 14-8-14 AML cells. B220+Mac1+ WT cells retained D-J germline allele.

Figure 14:
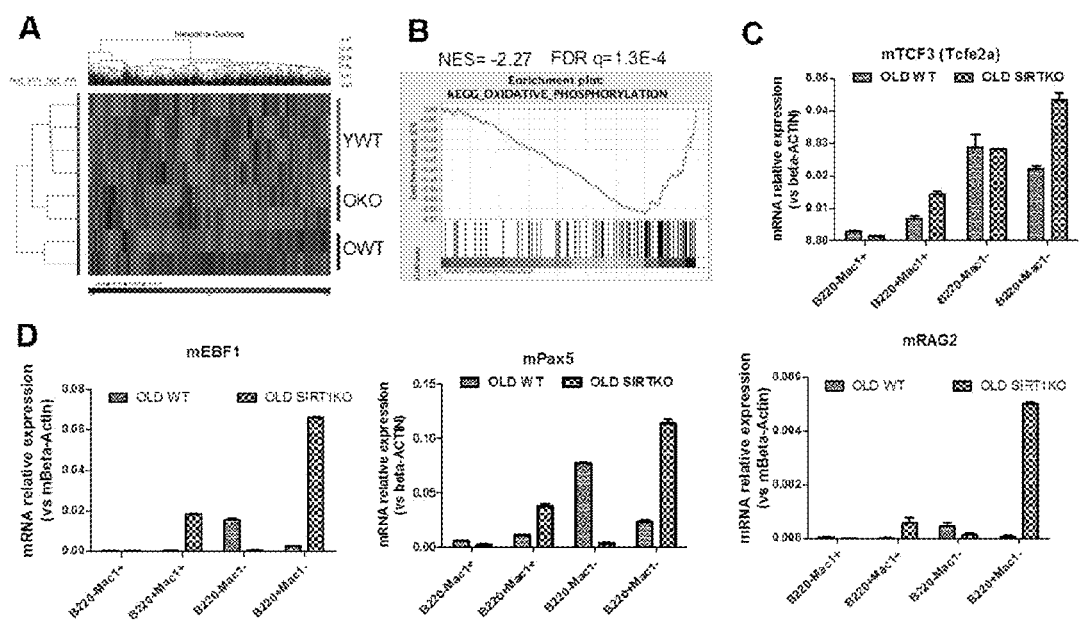

FIG. 14 Molecular characterization of aging HSCs and B-cell differentiation defect. (A) Hierarchical clustering of microarray expression data of sorted SP cells from YWT (10 weeks) vs old (16-20 months) WT or SIRT1 KO mice. (B) GSEA enrichment plot for oxidative phosphorylation pathway. (C) Real-time RTPCR analysis of E2A (encoded by mouse TCF3 gene) expression. (D) Realtime RT-PCR analysis of E2A target genes mEbf1, mPAX5 and mRag5.

Figure 15:
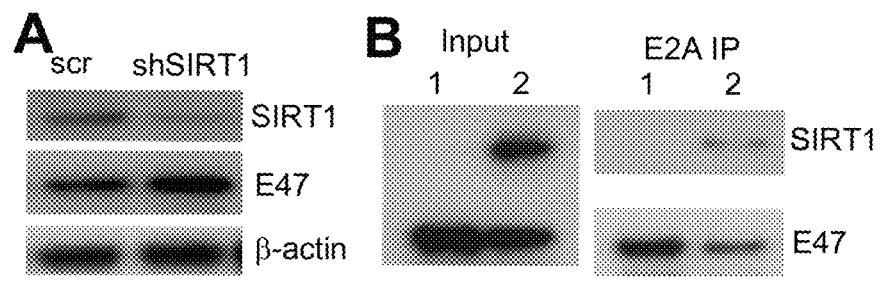

FIG. 15 SIRT1 regulates E2A in human cells. (A) Effect of SIRT1 knockdown on endogenous E47 (the large splice variant of E2A) expression in Sup-B15 cells. (B) E2A was co-expressed with empty vector (lane 1) or flag-SIRT1 (lane 2) in 293 cells for co-IP with an E2A antibody.

FIG. 16 Sirtuins in the quest for longevity.

Figure 17:
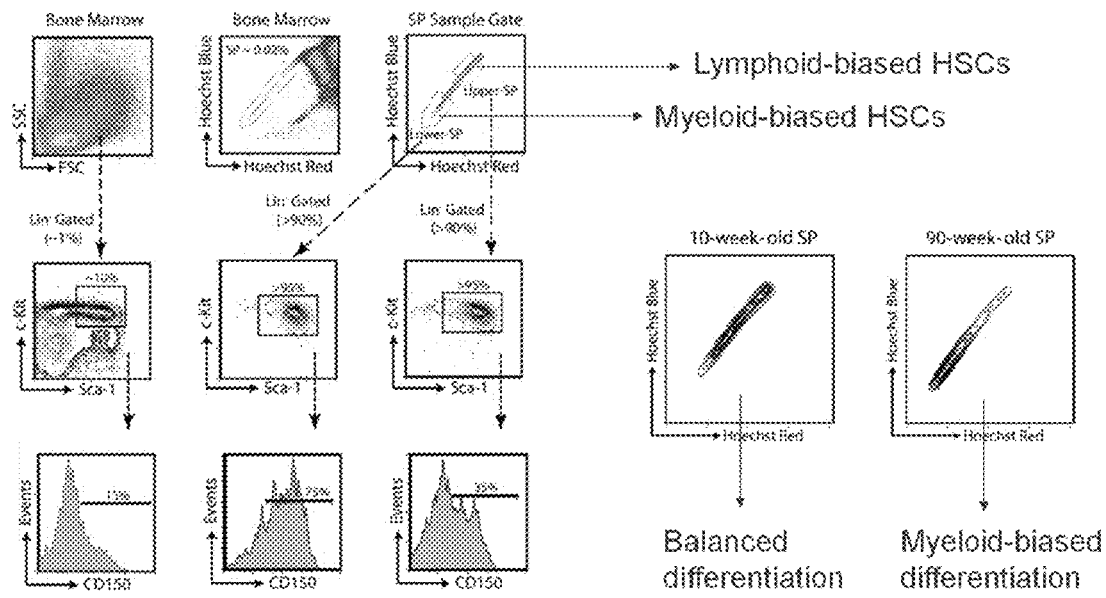

FIG. 17 Compartmental changes of aging HSCs.

Figure 18:
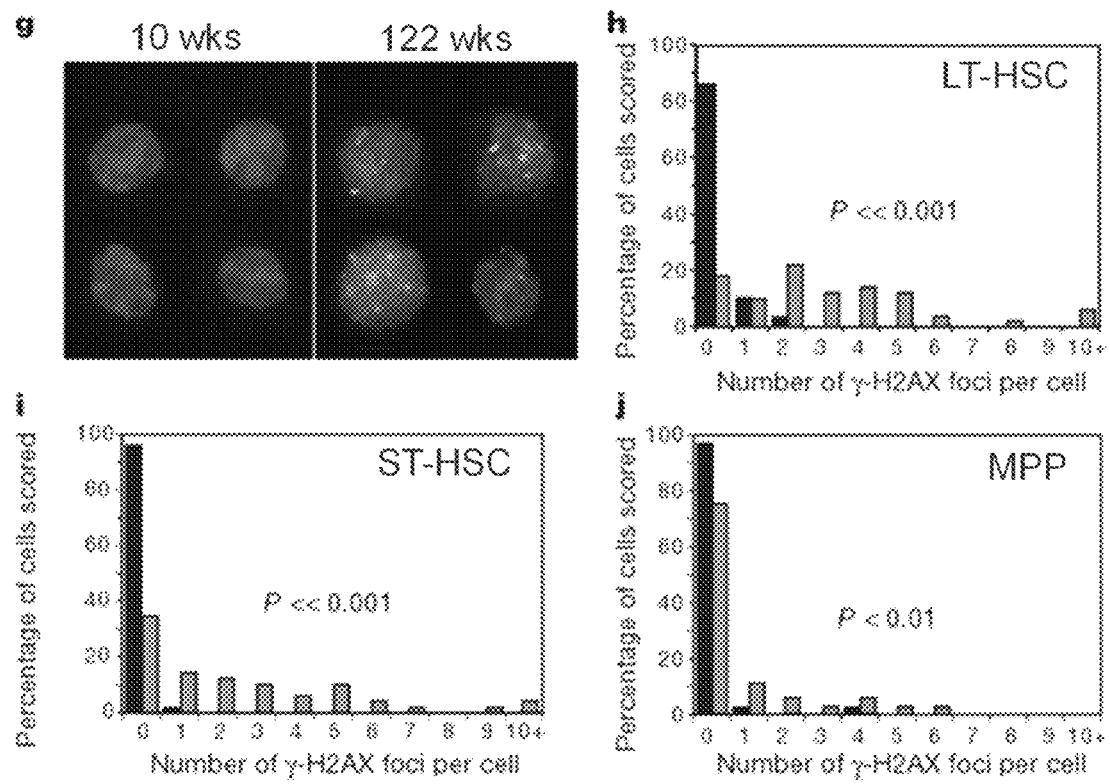

FIG. 18 DNA damage in aging HSCs.

Figure 19:
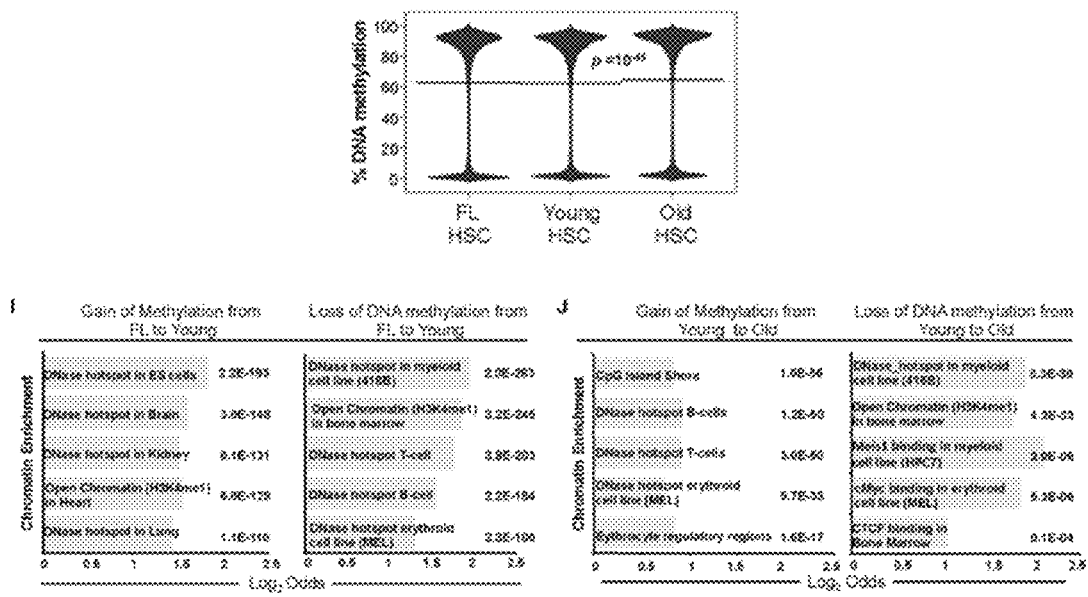

FIG. 19 Global DNA methylation changes in aging HSCs.

Figure 20:
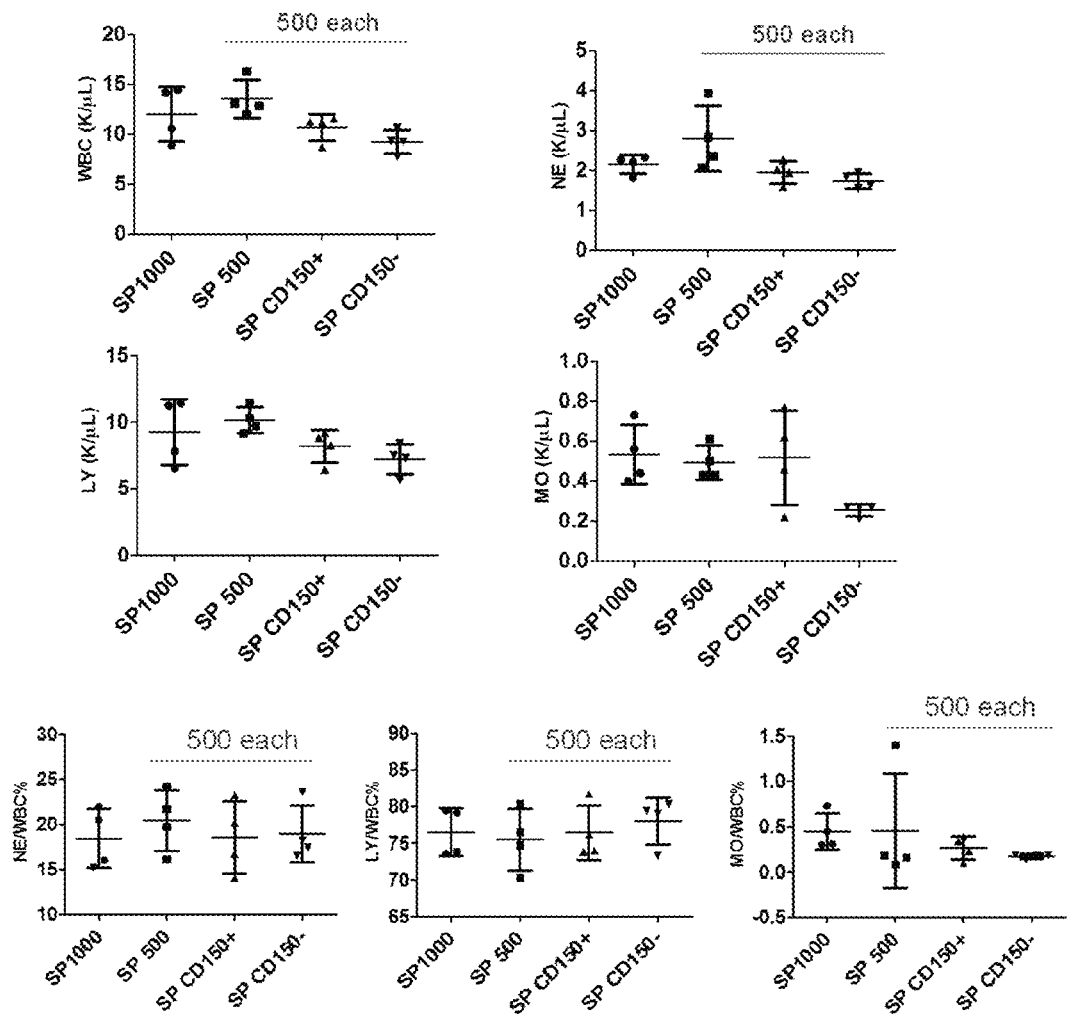

FIG. 20 Comparison of long term reconstitution of 500 and 1000 SP cells, and 500 each CD150$^+$ SP and CD150-SP cells. Blood cells were counted 4 months after transplantation. N=4 for each histogram depicted.

Figure 21:
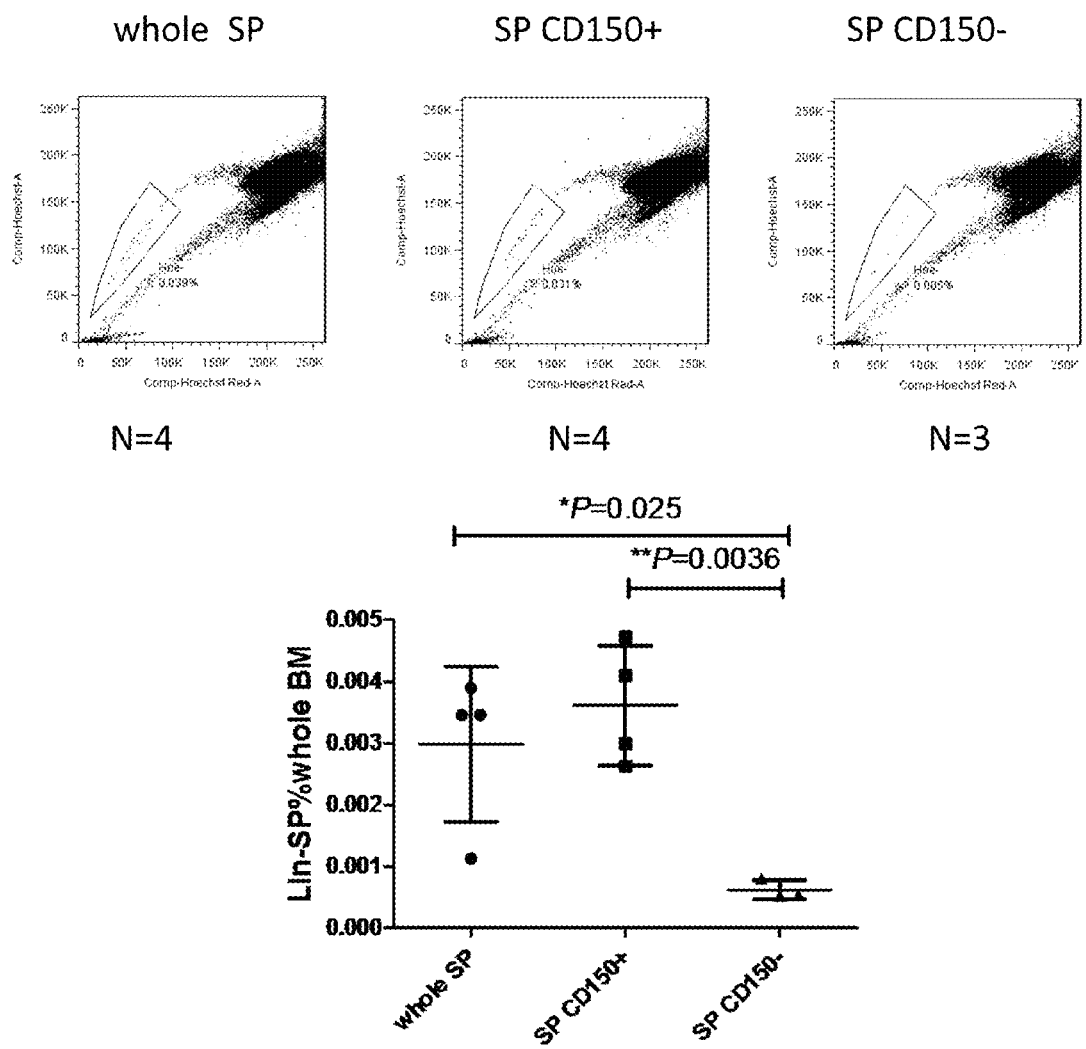

FIG. 21 Sorting scheme for Lin– side population and further separation with CD150 shown in the three top histograms. Bone marrow SP cell analysis shown in the bottom histogram.

Figure 22:
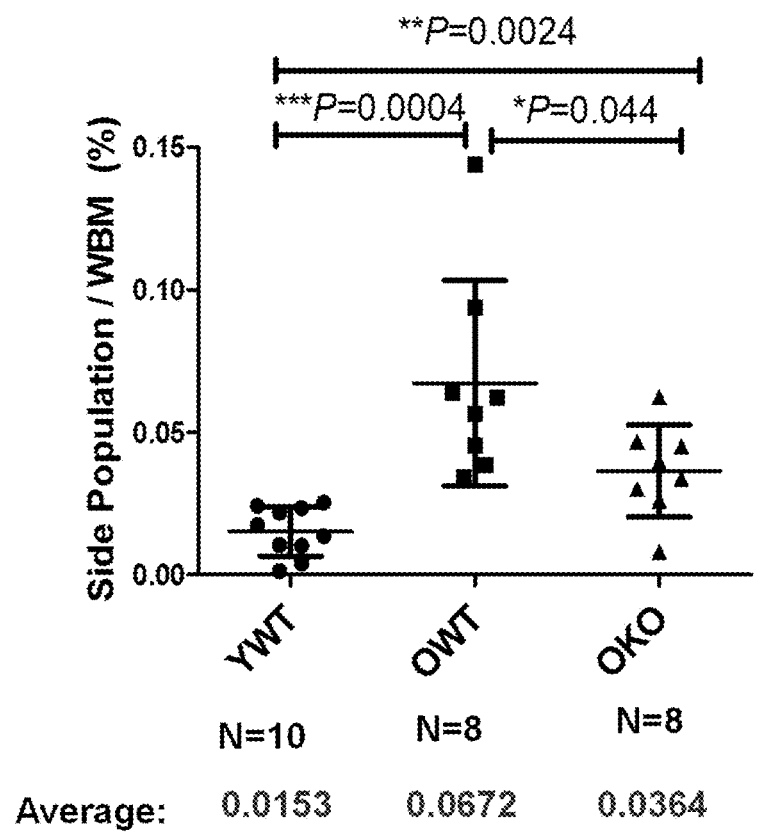

FIG. 22 Effects of aging on BALB/c mouse HSCs. YWT (young wild type; 2-3 months); OWT (old wild type; 16-22 months); OKO (old knock out; 16-22 months).

Figure 23:
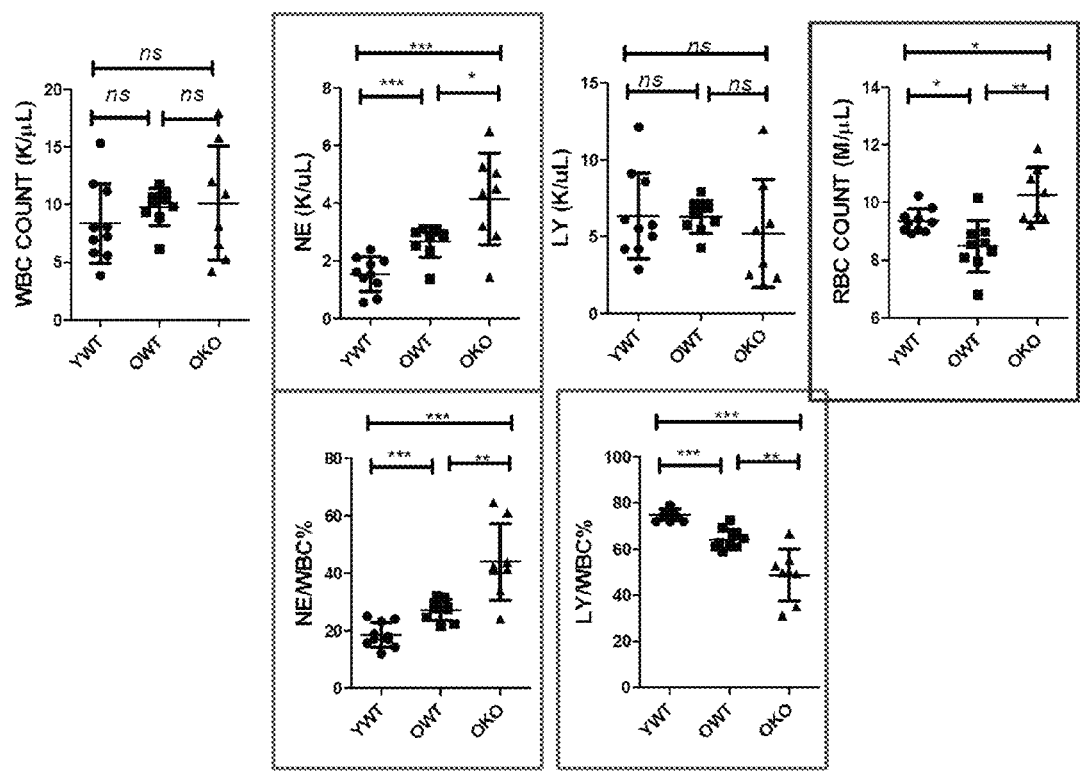

FIG. 23 Increased myeloid output in blood of aged mice. Y (young; 2-3 months); 0 (old 16-22 months).

Figure 24:
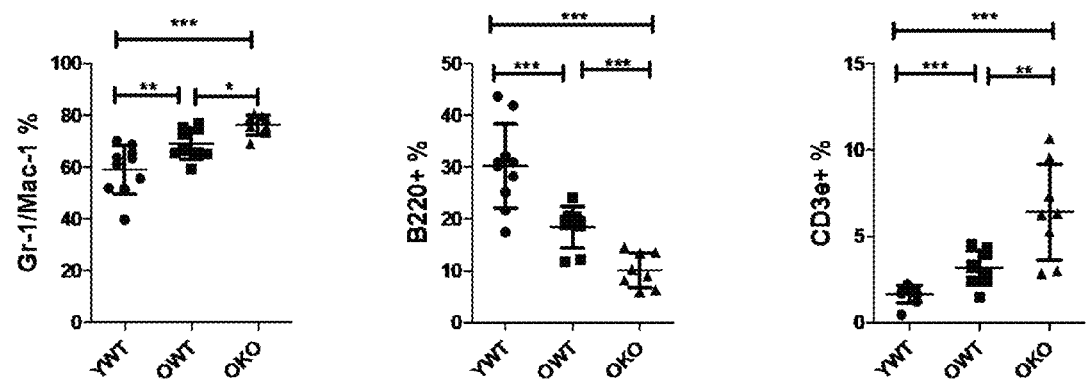

FIG. 24 Increased myeloid output in bone marrow of aged mice. YWT (young wild type; 2-3 months); OWT (old wild type; 16-22 months); OKO (old knock out; 16-22 months).

Figure 25:
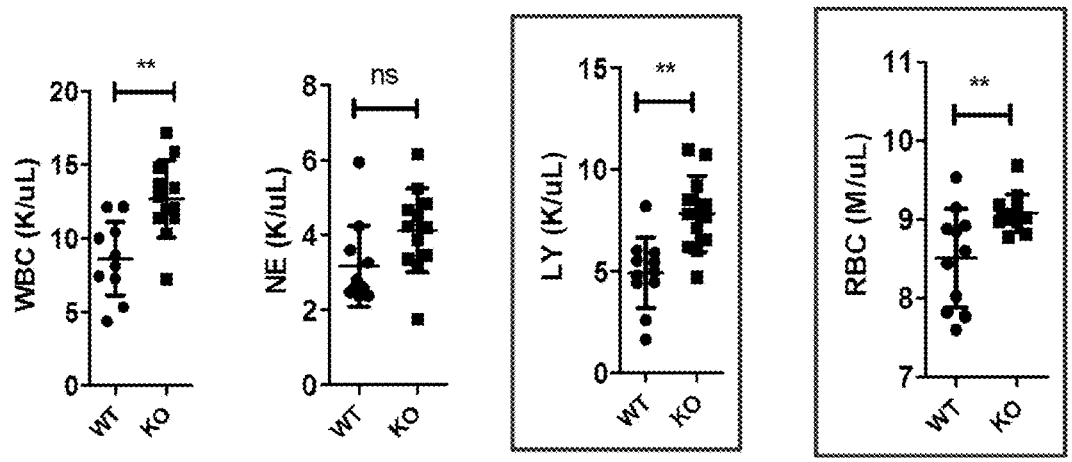
Figure 25:
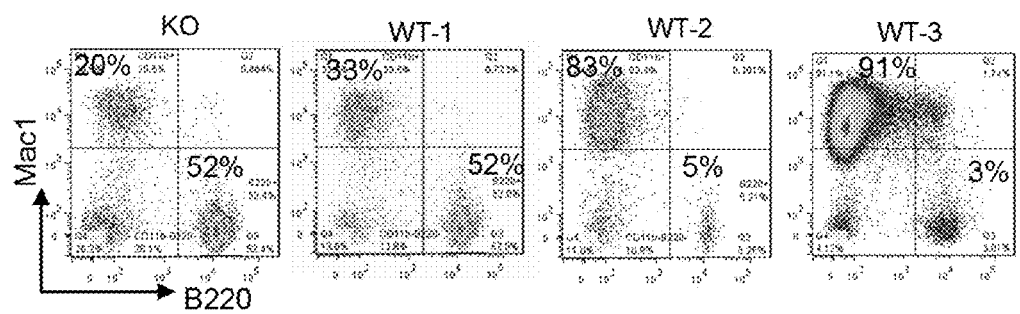
Figure 26:
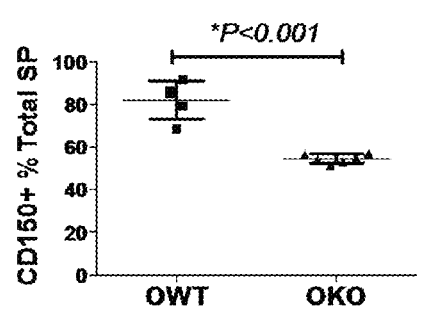
Figure 26:
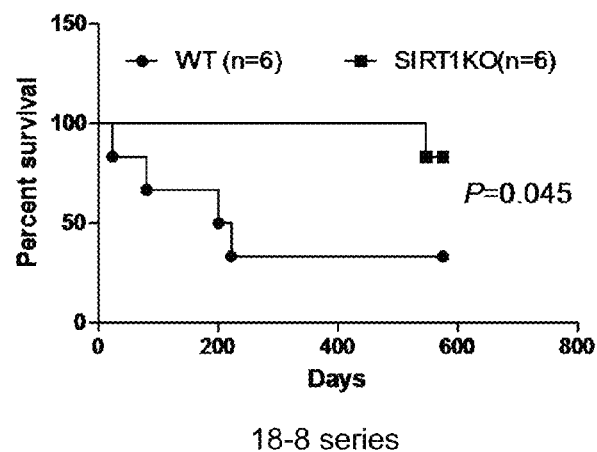

FIG. 25 14-8 series with old (14 months) original donors (upper panel). 20-10 series with old (20 months) original donors (lower panel).

FIG. 26 14-8 and 20-10 series showing percentage of CD150+ expression in OWT and OKO cells (left histogram). Survival rate of WT and SIRT1 knock out 18-8 carriers (right panel).

Figure 27:
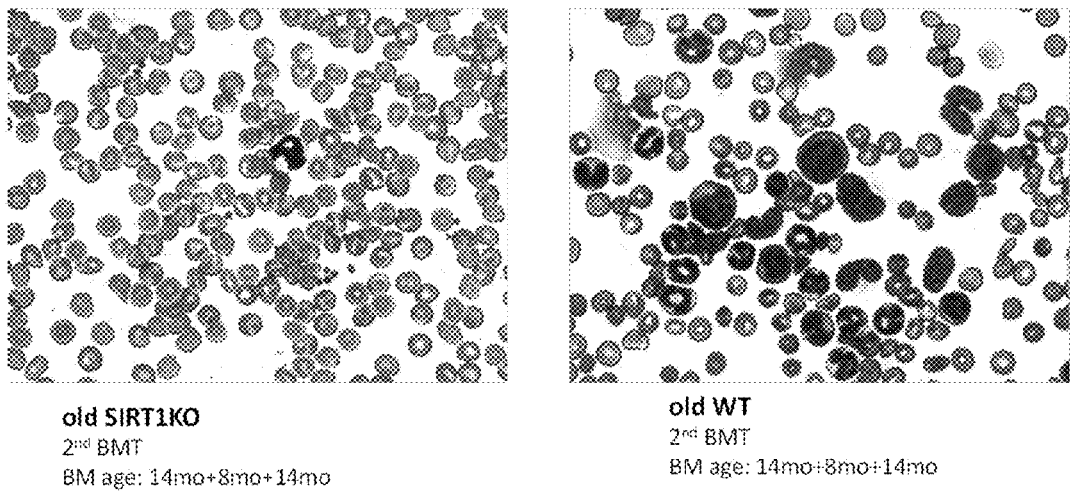

FIG. 27 Acute myeloid leukemia pathology in old WT mice. Left histogram shows immunohistochemistry of old SIRT1 knock out cells ($2^{nd}$ BMT, BM age 14-8-14). Right histogram shows immunohistochemistry of old wild type cells ($2^{nd}$ BMT, BM age 14-8-14).

Figure 28:
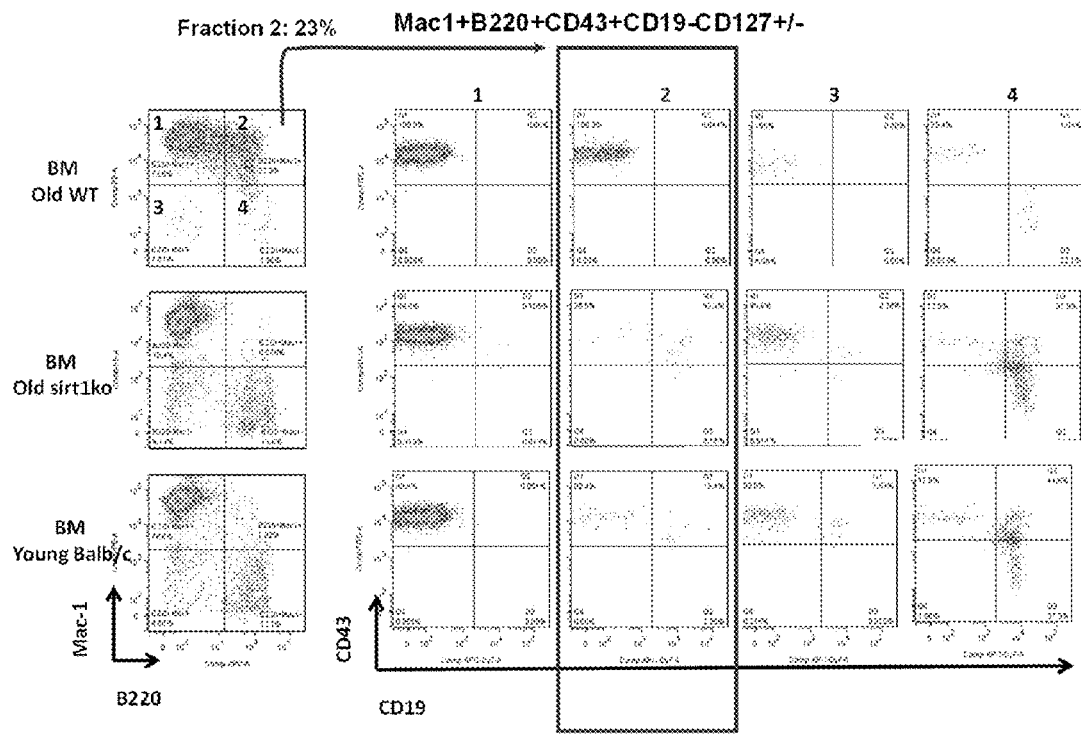

FIG. 28 FACS analysis of bone marrow derived from old wild type mice (histograms in top panel), old SIRT1 knock out mice (histograms in middle panel) and young BALB/C mice (histogram in bottom panel).

Figure 29:
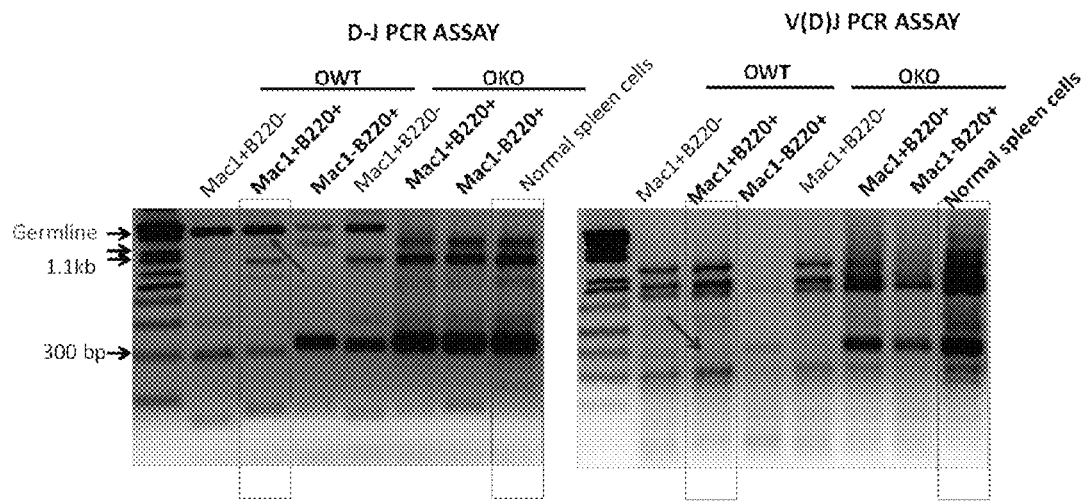

FIG. 29 Defective V(D)J recombination in B220+Mac1+ AML cells.

Figure 30:
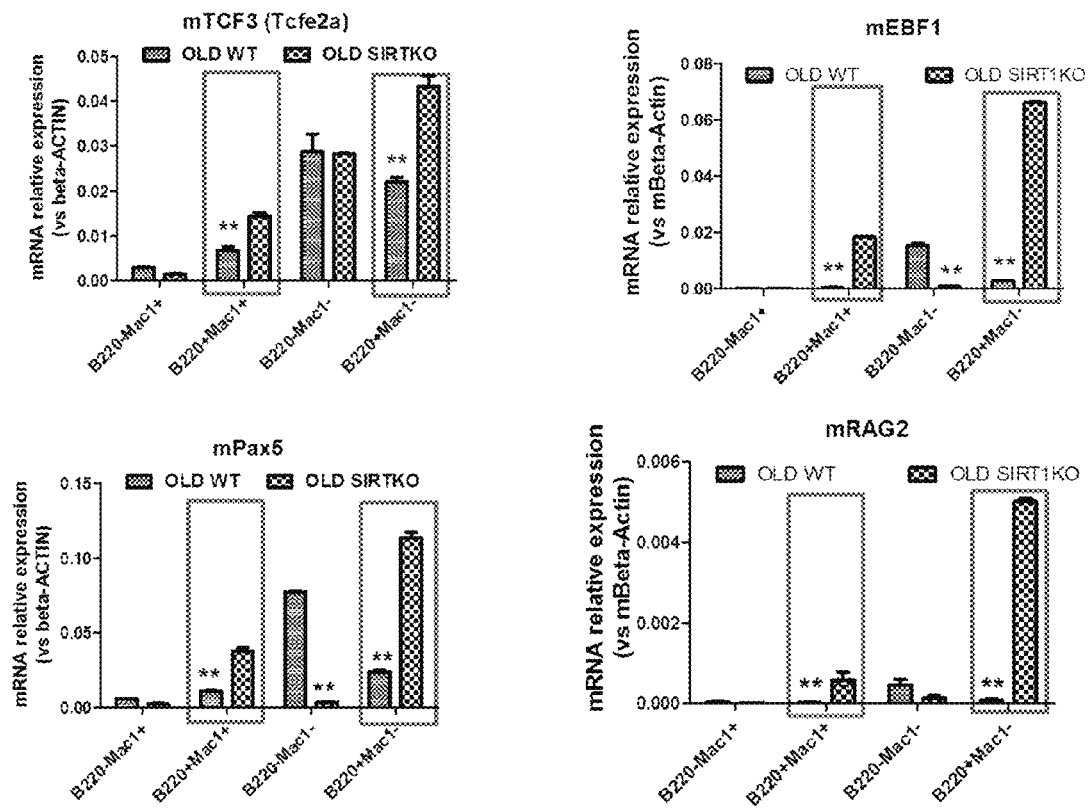

FIG. 30 B cell development related gene expression in OKO vs OWT animals. mRNA expression levels of TCF3 (top left histogram), EBF1 (top right histogram), Pac5 (bottom left histogram) and RAG2 (bottom right histogram) are shown.

Figure 31:
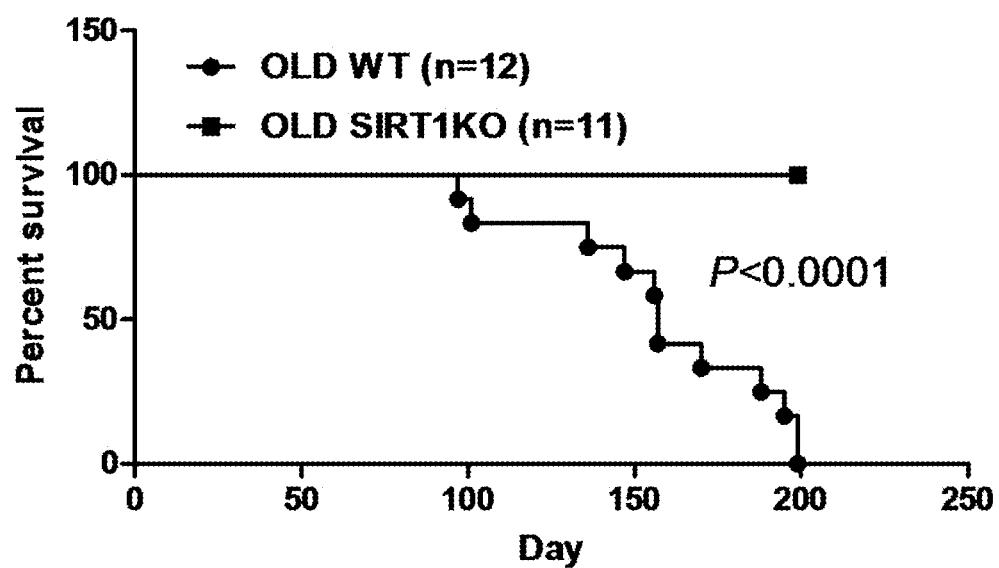

FIG. 31 Survival rate of old wild type and old knock out 14-19 recipients.

Figure 32:
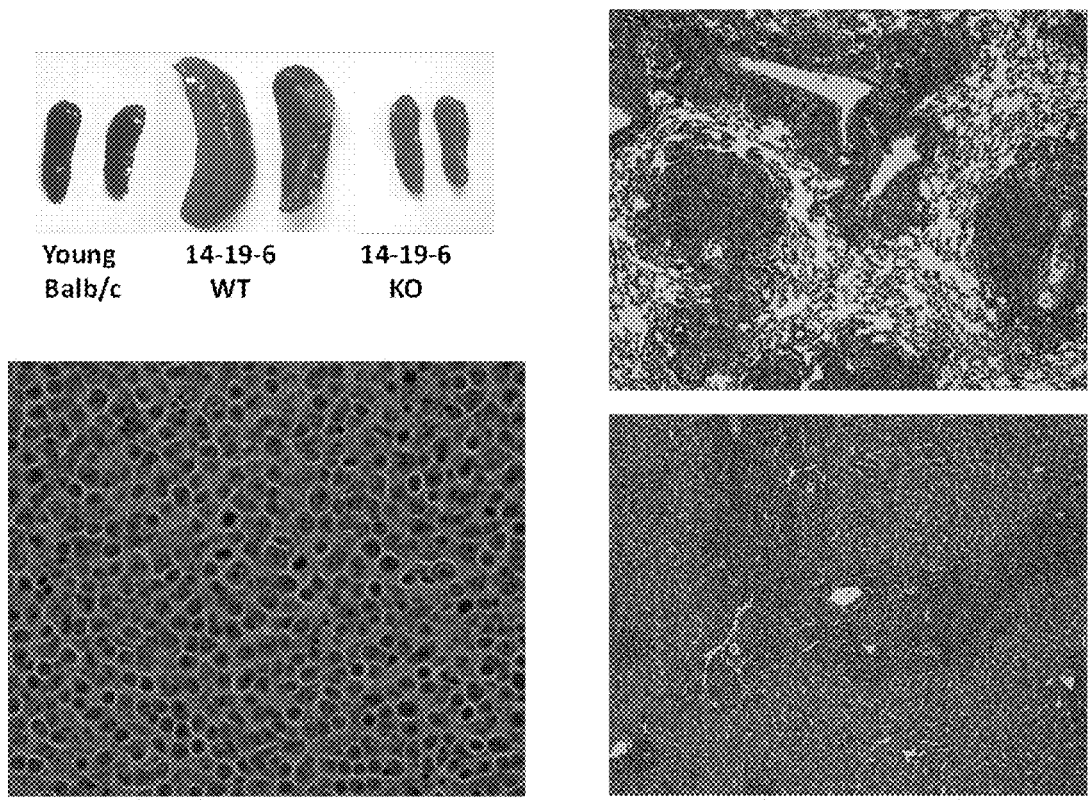

FIG. 32 Histochemcial analysis of spleen of old wild type and old knock out 14-19 recipients.

Figure 33:
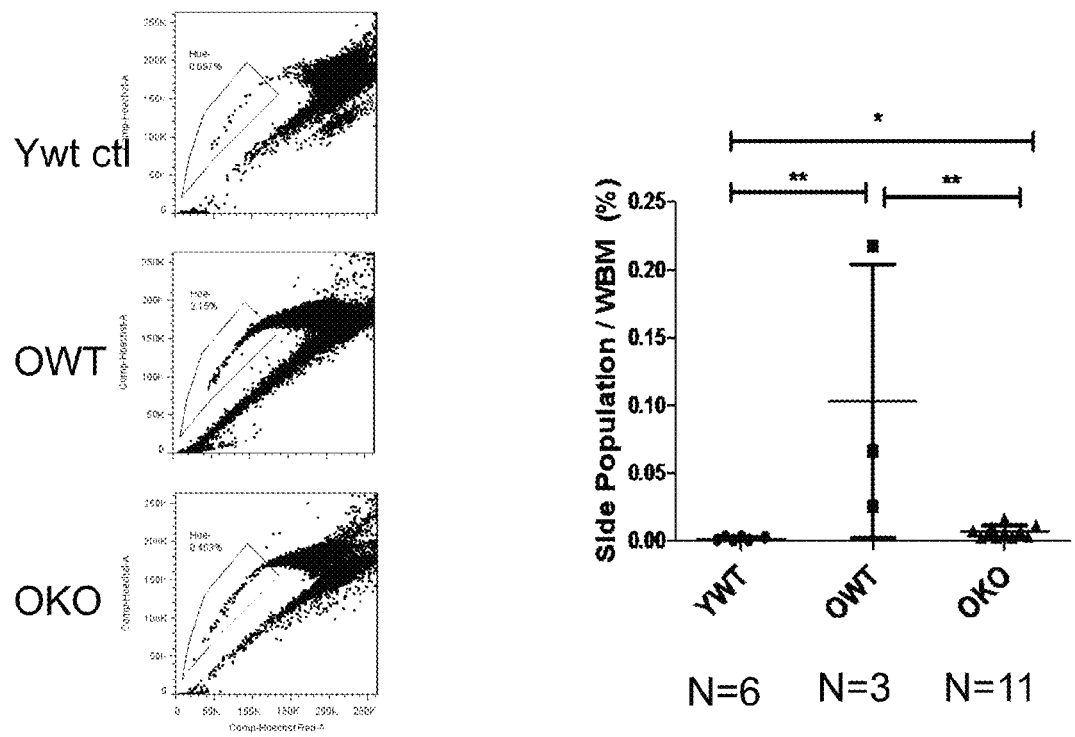

FIG. 33 Increased spleen size phenotype in old wild type animals is reversed in old SIRT1 knock out animals.

Figure 34:
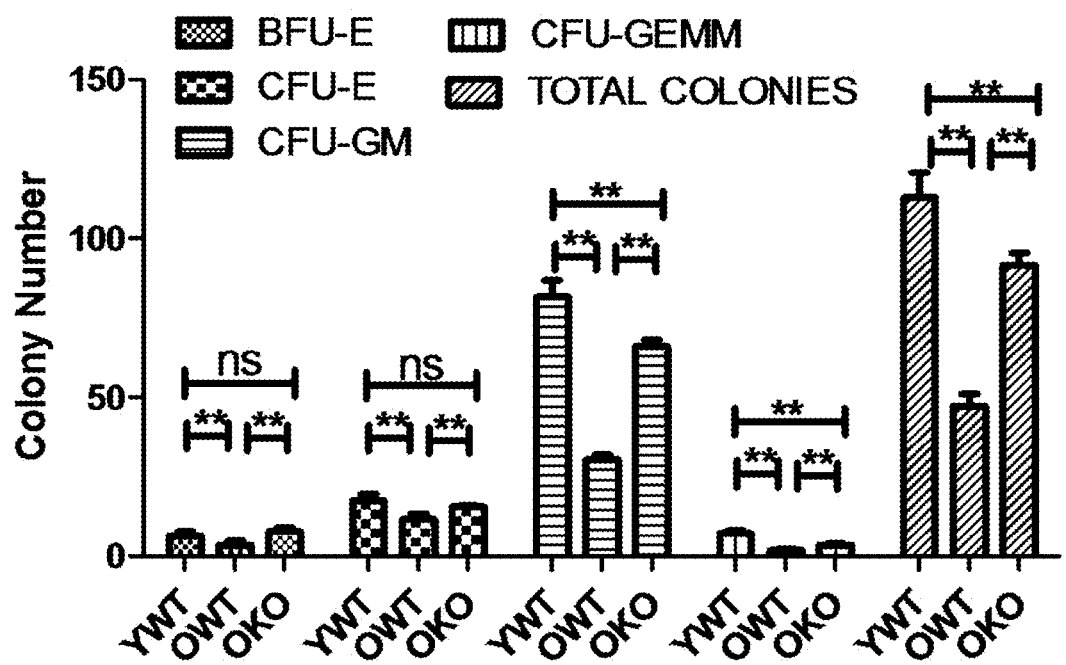
Figure 35:
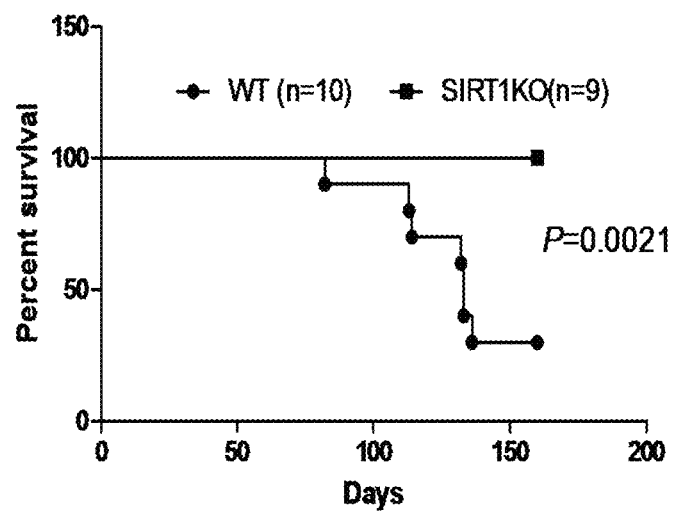

FIG. 34 Colony formation assay in young wild type (YWT), old wild type (OWT) and old knock out (OKO) animals.

FIG. 35 14-8-6 Z series: $3^{rd}$ transplant survival curve shows longer survival for knock out vs. wt p=0.0021.

Figure 36:
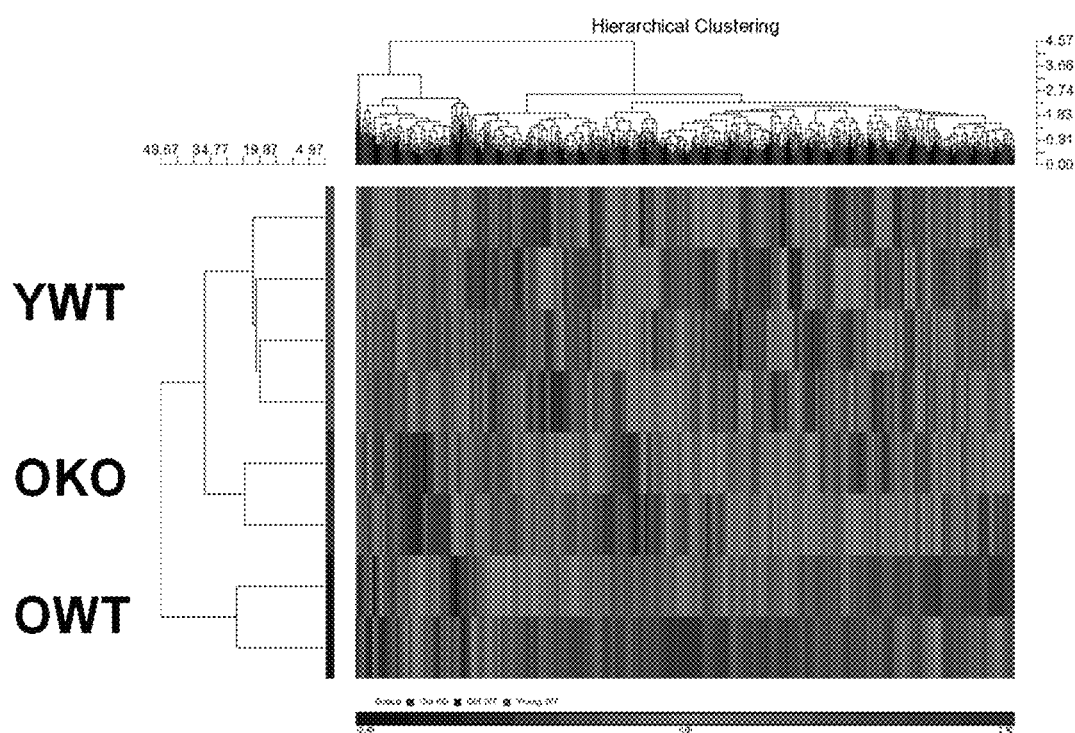

FIG. 36 SIRT1 knock out molecularly rejuvinates old HSCs.

Figure 37:
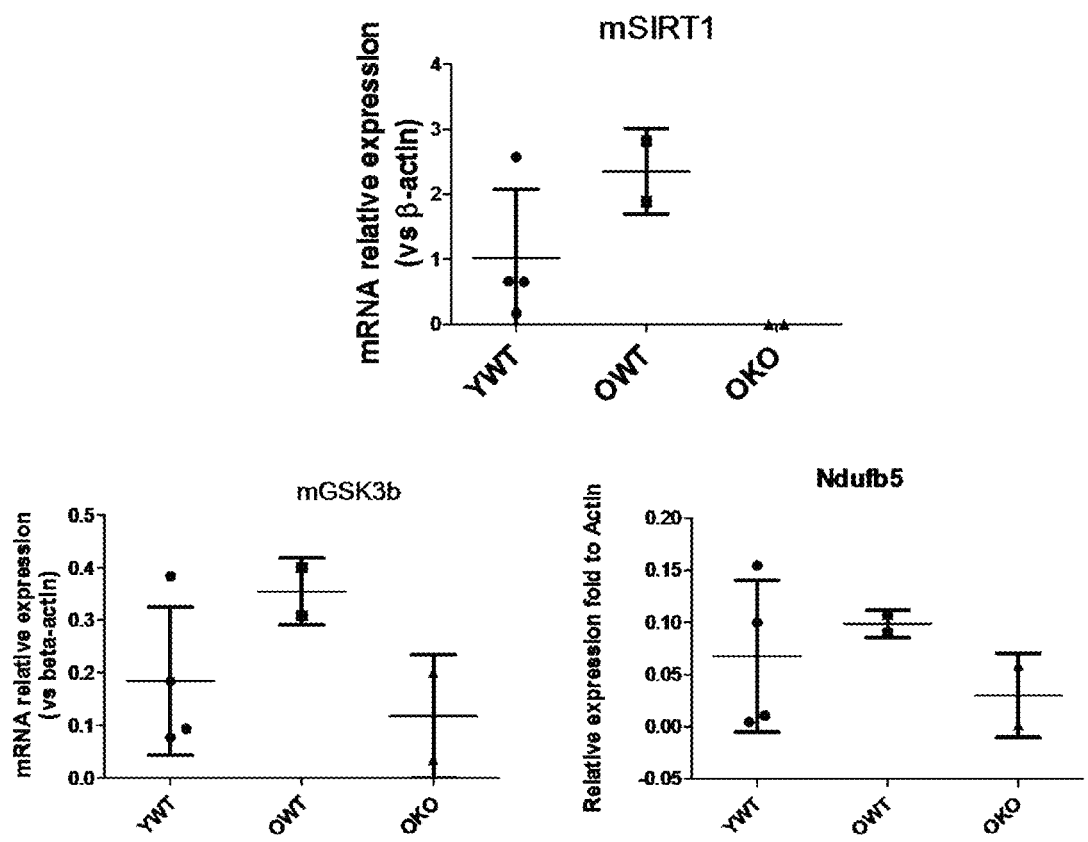

FIG. 37 mRNA expression analysis in YWT, OWT, and OKO animals. SIRT1 mRNA (top histogram); GSK3b mRNA (lower left histogram); Ndufb5 mRNA (bottom right histogram).

Figure 38:
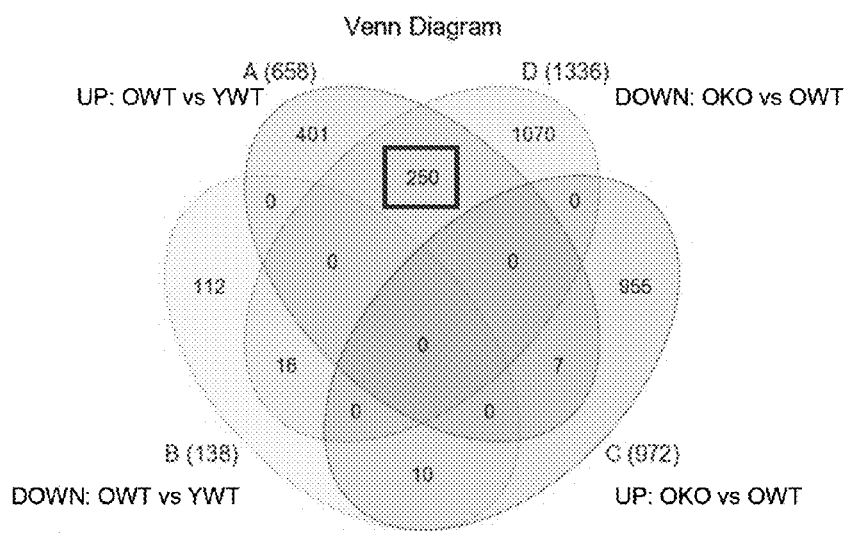

FIG. 38 Venn diagram analysis of expression changes. (A) Venn diagram analysis identified 250 genes that were upregulated in OWT compared to YWT, but were down regulated in OKO HSC cells. (B) The top 10 list of 250 genes identified in A.

Figure 39:
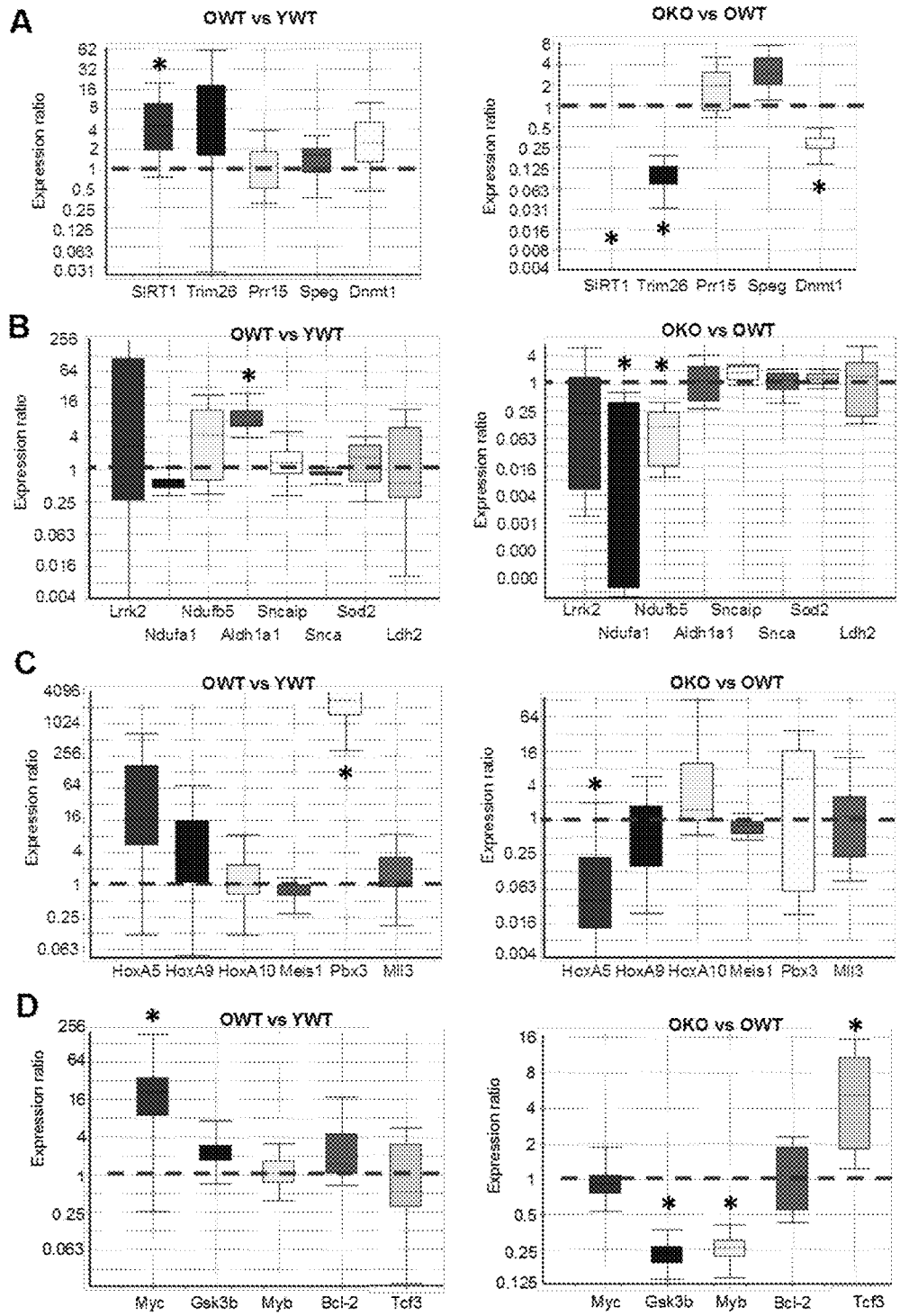

FIG. 39 Real-time quantitative RT-PCR assay of selected genes from pathway analyses. Real-time RT-PCR data were processed by REST 2009 software and normalized to the geometric mean of a panel of internal control genes including β-actin, CD45 and 18S RNA. The relative gene expression levels were presented as Whisker-box plots. (A) Top-listed genes from pathway and Venn diagram analysis. (B) REDOX and related genes. (C) HOX genes and their regulators. (D) Transcriptional factors and related genes. Asterisks indicate statistically significant difference (p<0.05) from the neutral value of 1 (dashed line).

Figure 40:
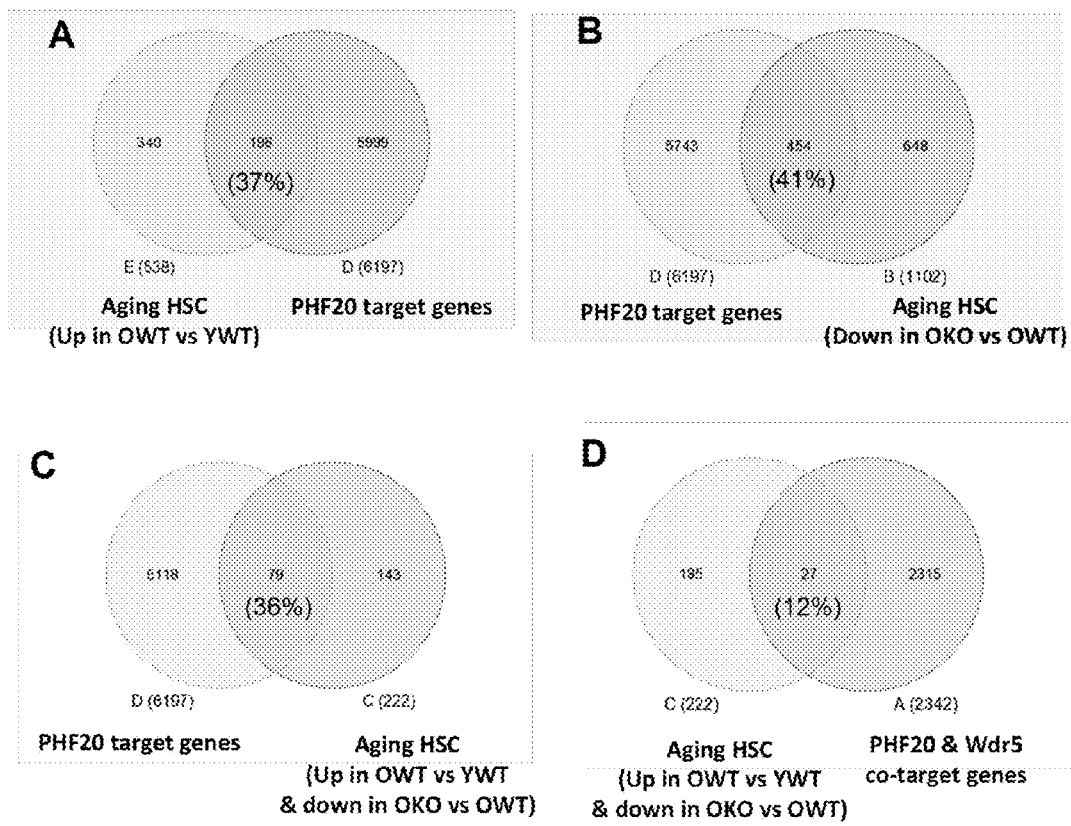

FIG. 40 Venn diagram analysis of SIRT1 vs PHF20 target genes. (A) Overlap of genes upregulated in OWT over YWT HSCs vs PHF20 target genes. (B) Overlap of genes down-regulated in OKO over OWT HSCs vs PHF20 target genes. (C, D) Overlap of PHF target genes (C) or PHF20/Wdr5 co-target genes (D) with 222 annotated genes from 250 genes that were up in OWT vs YWT but down in OKO.

DETAILED DESCRIPTION OF THE INVENTION

I. Definitions

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N.Y. 1989). Any methods, devices and materials similar or equivalent to those described herein can be used in the practice of this invention. The following definitions are provided to facilitate understanding of certain terms used frequently herein and are not meant to limit the scope of the present disclosure.

The terms "culture," "culturing," "grow," "growing," "maintain," "maintaining," "expand," "expanding," etc., when referring to cell culture itself or the process of culturing, can be used interchangeably to mean that a cell is maintained outside the body (e.g., ex vivo) under conditions suitable for survival. Cultured cells are allowed to survive, and culturing can result in cell growth, differentiation, or division. The term does not imply that all cells in the culture survive or grow or divide, as some may naturally senesce, etc. Cells are typically cultured in media, which can be changed during the course of the culture.

The terms "media" and "culture solution" refer to the cell culture milieu. Media is typically an isotonic solution, and can be liquid, gelatinous, or semi-solid, e.g., to provide a matrix for cell adhesion or support. Media, as used herein, can include the components for nutritional, chemical, and structural support necessary for culturing a cell.

As used herein, "conditions to allow growth" in culture and the like refers to conditions of temperature (typically at about 37° C. for mammalian cells), humidity, $CO_2$ (typically around 5%), in appropriate media (including salts, buffer, serum), such that the cells are able to undergo cell division or at least maintain viability for at least 24 hours, preferably longer (e.g., for days, weeks or months).

Suitable culture conditions are described herein, and can include standard tissue culture conditions. For example, HSCs, iPSCs, ES cells, or somatic cells can be cultured in a buffered media that includes amino acids, nutrients, growth factors, etc, as will be understood in the art. In some aspects, the culture of ES cells or iPSCs includes feeder cells (e.g., fibroblasts), while in others, the culture is devoid of feeder cells. Cell culture conditions are described in more detail, e.g., in Picot, Human Cell Culture Protocols (Methods in Molecular Medicine) 2010 ed. and Davis, Basic Cell Culture 2002 ed.

Culture conditions that support differentiation of HSCs to red blood cells, lymphoid or myeloid cells are well known in the art and described in more detail in Kevin D. Bunting (Ed) Hematopopietic Stem Cell Protocols in series Methods in Molecular Biology (John M. Walker, Series Ed.) ISBN 978-1-58829-868-3 and Dravid, G. et al. Molecular Therapy, 2011, 19: 768-781. Growth factors can also be included in the culture to promote HSC differentiation in to red blood cells, lymphoid cell or myeloid cells. Non-limiting examples of growth factors known in the art to support in vitro myeloid differentiation include stem cell factor (SCF), Flt3 ligand, thrombopoietin, interleukin-3 (IL-3) and erythropoietin. Non-limiting examples of growth factors known in the art to support in vitro lymphoid differentiation include SCF, Flt3 ligand, thrombopoietin, plus IL-7 (for B and T cells) or IL-15 (for NK cells). Further, Notch receptor ligand Delta-like 1 may be used to enhance T cell differentiation.

The term "derived from," when referring to cells or a biological sample, indicates that the cell or sample was obtained from the stated source at some point in time. For example, a cell derived from an individual can represent a primary cell obtained directly from the individual (i.e., unmodified), or can be modified, e.g., by introduction of a recombinant vector, by culturing under particular conditions, or immortalization. In some cases, a cell derived from a given source will undergo cell division and/or differentiation such that the original cell is no longer exists, but the continuing cells will be understood to derive from the same source.

A "somatic cell" is a cell forming the body of an organism. Somatic cells include cells making up organs, skin, blood, bones and connective tissue in an organism, but not germ line cells or stem cells.

A "hematologic cell" is a cell forming the blood, bone marrow and lymph nodes of an organism. Hematologic cells include platelets, neutrophils, monocytes, macrophages, basophils, lymphocytes, erythrocytes and eosinophils. Hematologic cells are derived from a common hematopoietic stem cell (HSC). A "hematopoietic stem cell" as provided herein refers to a somatic stem cell that is able to give rise to all blood cells. A hematopoietic stem cell has the capacity to differentiate into cells of the myeloid lineage (i.e. erythrocytes, mast cells, basophils, neutrophils, eosinophils, monocytes and macrophages) and the lymphoid lineage (i.e. natural killer cells, T cells and B cells).

A "stem cell" is a cell characterized by the ability of self-renewal through mitotic cell division and the potential to differentiate into a tissue or an organ. Among mammalian stem cells, embryonic stem cells (ES cells) and somatic stem cells (e.g., HSC) can be distinguished. Embryonic stem cells reside in the blastocyst and give rise to embryonic tissues, whereas somatic stem cells reside in adult tissues for the purpose of tissue regeneration and repair.

The term "pluripotent" or "pluripotency" refers to cells with the ability to give rise to progeny that can undergo differentiation, under appropriate conditions, into cell types that collectively exhibit characteristics associated with cell lineages from the three germ layers (endoderm, mesoderm, and ectoderm). Pluripotent stem cells can contribute to tissues of a prenatal, postnatal or adult organism. A standard art-accepted test, such as the ability to form a teratoma in 8-12 week old SCID mice, can be used to establish the pluripotency of a cell population. However, identification of various pluripotent stem cell characteristics can also be used to identify pluripotent cells.

An "induced pluripotent stem cell" or "iPSC" refers to a pluripotent stem cell artificially (e.g. non-naturally, in a laboratory setting) derived from a non-pluripotent cell. A "non-pluripotent cell" can be a cell of lesser potency to self-renew and differentiate than a pluripotent stem cell. Cells of lesser potency can be, but are not limited to adult stem cells, tissue specific progenitor cells, primary or secondary cells. An adult stem cell is an undifferentiated cell found throughout the body after embryonic development. Adult stem cells multiply by cell division to replenish dying cells and regenerate damaged tissue. Adult stem cells have the ability to divide and create another like cell and also divide and create a more differentiated cell. Even though adult stem cells are associated with the expression of pluripotency markers such as Rex1, Nanog, Oct4 or Sox2, they do not have the ability of pluripotent stem cells to differentiate into the cell types of all three germ layers. Adult stem cells have a limited potency to self-renew and generate progeny of distinct cell types. Without limitation, an adult stem cell can be a hematopoietic stem cell, a cord blood stem cell, a mesenchymal stem cell, an epithelial stem cell, a skin stem cell or a neural stem cell. A tissue specific progenitor refers to a cell devoid of self-renewal potential that is committed to differentiate into a specific organ or tissue. A primary cell includes any cell of an adult or fetal organism apart from egg cells, sperm cells and stem cells. Examples of useful primary cells include, but are not limited to, skin cells, bone cells, blood cells, cells of internal organs and cells of connective tissue. A secondary cell is derived from a primary cell and has been immortalized for long-lived in vitro cell culture.

The term "reprogramming" refers to the process of dedifferentiating a non-pluripotent cell (e.g., a somatic cell) into a cell exhibiting pluripotent stem cell characteristics (e.g., a human induced pluripotent stem cell).

Where appropriate the expanding transfected derived stem cell may be subjected to a process of selection. A process of selection may include a selection marker introduced into an induced pluripotent stem cell upon transfection. A selection marker may be a gene encoding for a polypeptide with enzymatic activity. The enzymatic activity includes, but is not limited to, the activity of an acetyltransferase and a phosphotransferase. In some embodiments, the enzymatic activity of the selection marker is the activity of a phosphotransferase. The enzymatic activity of a selection marker may confer to a transfected induced pluripotent stem cell the ability to expand in the presence of a toxin. Such a toxin typically inhibits cell expansion and/or causes cell death. Examples of such toxins include, but are not limited to, hygromycin, neomycin, puromycin and gentamycin. In some embodiments, the toxin is hygromycin. Through the enzymatic activity of a selection marker, a toxin may be converted to a non-toxin, which no longer inhibits expansion and causes cell death of a transfected induced pluripotent stem cell. Upon exposure to a toxin, a cell lacking a selection marker may be eliminated and thereby precluded from expansion.

Identification of the induced pluripotent stem cell may include, but is not limited to the evaluation of aforementioned pluripotent stem cell characteristics. Such pluripotent stem cell characteristics include without further limitation, the expression or non-expression of certain combinations of molecular markers. Further, cell morphologies associated with pluripotent stem cells are also pluripotent stem cell characteristics.

"Nucleic acid" refers to deoxyribonucleotides or ribonucleotides and polymers thereof in either single- or double-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, and 2-O-methyl ribonucleotides.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The terms "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

The terms "identical" or percent "identity," in the context of two or more nucleic acids or proteins, refer to two or more sequences or subsequences that are the same or have a specified percentage of nucleotides or amino acids that are the same (i.e., about 60% identity, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI web site at ncbi.nlm.nih.gov/BLAST. Such sequences are then said to be "substantially identical." This definition also refers to, or may be applied to, the compliment of a test sequence. The definition also includes sequences that have deletions and/or additions, as well as those that have substitutions. Identity typically exists over a region that is at least about 50 amino acids or nucleotides in length, or over a region that is 50-100 amino acids or nucleotides in length, or over the entire length of a given sequence.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell (Sambrook et al., 1989, *Molecular Cloning: A Laboratory Manual*, 18.1-18.88).

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. Transgenic cells and animals are those that express a heterologous gene or coding sequence, typically as a result of recombinant methods.

The term "exogenous" refers to a molecule or substance (e.g., a compound, nucleic acid or protein) that originates from outside a given cell or organism. Conversely, the term "endogenous" refers to a molecule or substance that is native to, or originates within, a given cell or organism.

The term "sample" includes sections of tissues such as biopsy and autopsy samples, and frozen sections taken for histological purposes. Such samples include blood and blood fractions or products (e.g., bone marrow, serum, plasma, platelets, red blood cells, and the like), sputum, tissue, cultured cells (e.g., primary cultures, explants, and transformed cells), stool, urine, other biological fluids (e.g., prostatic fluid, gastric fluid, intestinal fluid, renal fluid, lung fluid, cerebrospinal fluid, and the like), etc. A sample is typically obtained from a "subject" such as a eukaryotic organism, most preferably a mammal such as a primate, e.g., chimpanzee or human; cow; dog; cat; a rodent, e.g., guinea pig, rat, mouse; rabbit; or a bird; reptile; or fish. In some embodiments, the sample is obtained from a human.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

The terms "treat," "treating" or "treatment," and other grammatical equivalents as used herein, include alleviating, abating or ameliorating a disease, condition or symptoms (e.g. hematological disease), preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder.

The terms "prevent," "preventing" or "prevention," and other grammatical equivalents as used herein, include to keep from developing, occur, hinder or avert a disease or condition symptoms as well as to decrease the occurrence of symptoms. The prevention may be complete (i.e., no detectable symptoms) or partial, so that fewer symptoms are observed than would likely occur absent treatment. The terms further include a prophylactic benefit. For a disease or condition to be prevented, the compositions may be administered to a patient at risk of developing a particular disease (e.g. hematological disease), or to a patient reporting one or more of the physiological symptoms of a disease, even though a diagnosis of this disease may not have been made.

Where combination treatments are contemplated, it is not intended that the agents (i.e. SIRT1 inhibitors) described herein be limited by the particular nature of the combination. For example, the agents described herein may be administered in combination as simple mixtures as well as chemical hybrids. An example of the latter is where the agent is covalently linked to a targeting carrier or to an active pharmaceutical. Covalent binding can be accomplished in many ways, such as, though not limited to, the use of a commercially available cross-linking agent.

An "effective amount" is an amount sufficient to accomplish a stated purpose (e.g. achieve the effect for which it is administered, treat a disease, reduce enzyme activity, reduce one or more symptoms of a disease or condition, reduce kinase activity in a cell, reduce the activity of SIRT1 in a cell). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme or protein (e.g. SIRT1) relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

"Patient" or "subject in need thereof" refers to a living organism suffering from or prone to a disease or condition that can be treated by using the methods provided herein. The term does not necessarily indicate that the subject has been diagnosed with a particular disease, but typically refers to an individual under medical supervision. Non-limiting examples include humans, other mammals, bovines, rats, mice, dogs, monkeys, goat, sheep, cows, deer, and other non-mammalian animals. In embodiments, a patient is human.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. Contacting may include allowing two species to react, interact, or physically touch, wherein the two species may be a compound (e.g. SIRT1 inhibitor) as described herein and a protein or enzyme (e.g. SIRT1). In embodiments, the protein may be SIRT1. In embodiments contacting includes allowing a compound described herein to interact with a protein or enzyme that is involved in chromatin remodeling.

As defined herein, the term "inhibition", "inhibit", "inhibiting" and the like in reference to a protein-inhibitor interaction means negatively affecting (e.g. decreasing) the activity or function of the protein (e.g. decreasing gene transcription regulated by SIRT1) relative to the activity or function of the protein (e.g. SIRT1, histone deacetylase) in the absence of the inhibitor (e.g. SIRT1, histone deacetylase). In embodiments inhibition refers to reduction of a disease or symptoms of disease. In embodiments, inhibition refers to a reduction in the activity of a signal transduction pathway or signaling pathway (e.g. reduction of a pathway involving histone modification by SIRT1). Thus, inhibition includes, at least in part, partially or totally blocking stimulation, decreasing, preventing, or delaying activation, or inactivating, desensitizing, or down-regulating signal transduction or enzymatic activity or the amount of a protein (e.g. SIRT1). In embodiments, inhibition refers to inhibition of SIRT1.

The terms "inhibitor," "repressor" or "antagonist" or "downregulator" interchangeably refer to a substance that results in a detectably lower expression or activity level as compared to a control. The inhibited expression or activity can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control. An "inhibitor" is a compound or small molecule that inhibits SIRT1 activity (e.g., deacetylation) e.g., by binding, partially or totally blocking stimulation, decrease, prevent, or delay activation, or inactivate, desensitize, or down-regulate signal transduction or enzymatic activity necessary for protein activity Inhibition as provided herein may also include decreasing or blocking a protein activity (e.g., deacetylation) by expressing a mutant form of said protein thereby decreasing or blocking its activity.

"Disease" or "condition" refer to a state of being or health status of a patient or subject capable of being treated using the methods provided herein. In embodiments, the disease is a disease related to (e.g. caused by) SIRT1 or aberrant SIRT1 activity (e.g. anemia, leukemia, myeloid disease). Examples of diseases, disorders, or conditions include, but are not limited to immunodeficiency, immunomodulation, autoimmune diseases, and hematological diseases.

In some instances, "disease" or "condition" refer to "hematological disease." A hematological disease refers to a disease affecting a hematologic cell. In some instances the hematological disease is a non-cancerous (i.e. non-malignant) hematological disease. Non-cancerous hematological diseases as provided herein include any disease, disorder or condition related to hematologic cells which is not cancer. Examples of non-cancerous hematological diseases, disorders, or conditions include, but are not limited to hemoglobinopathies including sickle-cell disease, thalassemia, methemoglobinemia; anemias including iron deficiency anemia, folate deficiency, hemolytic anemias, megaloblastic anemia, vitamin B12 deficiency, pernicious anemia, immune mediated hemolytic anemia, drug-induced immune mediated hemolytic anemia (e.g. due to high dose of penicillin, methyldopa), hemoglobinopathies, paroxysmal nocturnal hemoglobinuria, and microangiopathic hemolytic anemia; disease characterized by decreased numbers of blood cells (e.g. erythrocytes, lymphocytes, myeloid cells) including myelodysplastic syndrome, myelofibrosis, neutropenia, agranulocytosis, Glanzmann's thrombasthenia, thrombocytopenia, idiopathic thrombocytopenic purpura, thrombotic thrombocytopenic purpura, and heparin-induced thrombocytopenia; myeloproliferative disorders including polycythemia vera, erythrocytosis, leukocytosis, and thrombocytosis; coagulopathies including thrombocytosis, recurrent thrombosis, disseminated intravascular coagulation, hemophilia, Von Willebrand disease, disseminated intravascular coagulation, protein S deficiency, and antiphospholipid syndrome.

In other instances the hematological disease is a cancerous (i.e. malignant) hematological disease. A cancerous hematological disease refers broadly to progressive, malignant diseases of the blood-forming organs and is generally characterized by a distorted proliferation and development of leukocytes and their precursors in the blood and bone marrow. A cancerous hematological disease is generally clinically classified on the basis of (1) the duration and character of the disease-acute or chronic; (2) the type of cell involved; myeloid (myelogenous), lymphoid (lymphogenous), or monocytic; and (3) the increase or non-increase in the number of abnormal cells in the blood-leukemic or aleukemic (subleukemic). Exemplary cancerous hematological diseases that may be treated with a method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia, lymphomas including Hodgkin's disease, non-Hodgkin's lymphoma, Burkitt's lymphoma, anaplastic large cell lymphoma, splenic marginal zone lymphoma, hepatosplenic T-cell lymphoma, and angioimmunoblastic T-cell lymphoma (AILT); myelomas including multiple myeloma and Waldenström macroglobulinemia; leukemia including acute lymphocytic leukemia (ALL), chronic lymphocytic leukemia (CLL), acute myelogenous leukemia (AML), chronic idiopathic myeloﬁbrosis (MF), chronic myelogenous leukemia (CML), T-cell prolymphocytic leukemia (T-PLL), B-cell prolymphocytic leukemia (B-PLL), chronic neutrophilic leukemia (CNL), hairy cell leukemia (HCL), T-cell large granular lymphocyte leukemia (T-LGL) and aggressive NK-cell leukemia.

As defined herein, the term "rejuvenation", "rejuvinated" or "rejuvenating" and the like in reference to an organism or a cell (e.g. hematopoietic stem cell) means the reversal of aging. Aging is the accumulation of damage to macromolecules, cells, tissues and organs. This damage may cause an increase or a decrease of certain cellular functionalities. For instance, while the potential of hematopoietic stem cells to self-renew declines with aging, their potential to develop into a cancerous cell may increase. Upon rejuvenation of a cell (e.g. hematopoietic stem cell) the damage that is associated with aging is repaired for example by treating a damaged cell (e.g. with a SIRT1 inhibitor) or by replacing it with new cells thereby restoring its functionality.

A "SIRT1 protein" (silent mating type information regulation 2 homolog) or NAD-dependent deacetylase sirtuin-1 as referred to herein is a member of the Class III histone deactylases (HDACs) and includes any of the naturally-occurring forms of the SIRT1 histone deacetylase protein or variants, homologs or functional fragments thereof that maintain SIRT 1 histone deacetylase protein activity (e.g. at least 50%, 80%, 90%, 95%, 96%, 97%, 98%, 99% or 100% activity compared to SIRT1). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion, e.g., the sirtuin core domain) compared to a naturally occurring SIRT1 polypeptide. In some aspects, the SOX2 protein is the protein as identified by the NCBI reference gi:215982798.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The term "associated" or "associated with" as used herein to describe a disease (e.g. an SIRT1 associated disease, a cancer associated with aberrant SIRT1 activity, SIRT1 associated cancer) means that the disease (e.g. cancer) is caused by, or a symptom of the disease is caused by SIRT1.

The tem "aberrant" as used herein refers to different from normal. When used to described enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by using a method as described herein), results in reduction of the disease or one or more disease symptoms.

II. Methods of Treatment

Provided herein are, inter alia, methods for treating and preventing diseases (e.g. hematological diseases) using SIRT1 inhibitors. The methods provided herein are particularly useful for treating or preventing a hematological diseases (e.g., non-cancerous, cancerous, age-related). Surprisingly, Applicants have discovered, inter alia, that treatment of aged hematopoietic stem cells (HSC) with a SIRT1 inhibitor results in rejuvenation of the aged HSC thereby restoring HSC functionality.

In one aspect, a method of treating or preventing a hematological disease in a subject in need thereof is provided. The method includes administering a therapeutically effective amount of a SIRT1 inhibitor to a subject, thereby treating or preventing a hematological disease in the subject, wherein the disease is not a cancerous hematological disease. In another aspect, a method of treating or preventing a hematological disease in a subject in need thereof is provided. The method includes administering a therapeutically effective amount of a SIRT1 inhibitor to a subject, thereby treating or preventing a hematological disease in the subject. In one embodiment, the disease is not a cancerous disease. The term "administer (or administering) an SIRT 1 inhibitor" means administering a compound that inhibits the activity, function or level (e.g. amount) of SIRT1 to a subject and, without being limited by mechanism, allowing sufficient time for the SIRT1 inhibitor to reduce the activity of SIRT1 or for the SIRT1 inhibitor to reduce one or more symptoms of a disease.

In one embodiment, the hematological disease is an age-related hematological disease. An "age-related" hematological disease as provided herein is a hematological disease, disorder or condition arising from senescence. Age-related hematological diseases as used herein therefore refer to diseases of an elderly subject. An elderly subject as referred to herein is a subject of 65 years or older. Thus, in one embodiment, the elderly subject is at least 60 years old. In other embodiments, the elderly subject is 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 years old. In some embodiments, the elderly subject is at least 65 years old. In other embodiments, the elderly subject is at least 70 years old. In some embodiments, the elderly subject is at least 75 years old. In other embodiments, the elderly subject is at least 80 years old. In some embodiments, the elderly subject is at least 85 years old. In other embodiments, the elderly subject is at least 90 years old.

In one embodiment, the method prevents an age-related hematological disease. In one embodiment, the hematological disease is a red blood cell disease, a lymphoid disease or a myeloid disease. Where the hematological disease is a red blood cell disease, the disease is a disease, disorder or condition affecting red blood cells (i.e. erythrocytes). In one embodiment, the red blood cell disease is anemia. In one embodiment, the anemia is age-related anemia (i.e. anemia occurring in an elderly subject). Where the hematological disease is a lymphoid disease, the hematological disease is a disease, disorder or condition affecting lymphoid cells (i.e. natural killer cells, B cells and T cells). In one embodiment, the lymphoid disease is age-related lymphocytopenia or lymphopenia. Where the hematological disease is a myeloid disease, the hematological disease is a disease, disorder or condition affecting myeloid cells (i.e. mast cells, basophils, neutrophils, eosinophils, monocytes and macrophages). In other embodiments, the myeloid disease is a pre-leukemic myeloid disease. In one embodiment, the pre-leukemic myeloid disease is an age-related pre-leukemic myeloid disease. In one embodiment, the pre-leukemic myeloid disease is a myelodysplastic syndrome or a chronic myeloproliferative disease. In another embodiment, the myelodysplastic syndrome is refractory anemia or refractory cytopenia. In one embodiment, the chronic myeloproliferative disease is polycythemia vera or essential thrombocythemia.

For the methods provided herein a SIRT1 inhibitor is administered to a subject to treat or prevent a hematological disease. A SIRT1 inhibitor is a compound or a small molecule that decreases the activity or the function, the level of activity or the level of function of SIRT1 or the level of SIRT1 or the level of SIRT1 in a particular physical state relative to the absence of the SIRT1 inhibitor. A "SIRT1 inhibitor" as used herein refers to an organic, bioorganic, or inorganic compound that alters the activity or function of a SIRT 1 protein, SIRT 1 encoding nucleic acid, or SIRT1 polysaccharide. Examples of a SIRT1 inhibitor include, but are not limited to nucleic acids, proteins, dominant negative proteins, peptides, oligosaccharides, polysaccharides, lipids, phospholipids, glycolipids, monomers, polymers, small molecules and organic compounds. The SIRT1 inhibitor may be a polynucleotide. In some embodiments, the SIRT1 inhibitor is a short hairpin RNA. In other embodiments, the SIRT1 inhibitor is a small interfering RNA. The SIRT1 inhibitor may be a protein. Useful SIRT1 inhibitors are disclosed, for example, in U.S. Patent Application US 2011-0092695 A1.

For the methods provided herein any SIRT1 inhibitor capable of altering (e.g. decreasing) the activity or function of a SIRT1 protein, SIRT1 encoding nucleic acid, or SIRT1 polysaccharide is contemplated. In some embodiments, the SIRT1 inhibitor is a small molecule or compound. In one embodiment, the SIRT1 inhibitor is a naphthol inhibitor, an indole inhibitor, a nicotinamide inhibitor, an urea inhibitor, a polyphenol inhibitor, a thienopyrimidine carboxamide inhibitor, inauhzin, a peptide inhibitor or an antisense nucleic acid (e.g., siRNA, shRNA, miRNA). Where the SIRT1 inhibitor is a naphthol inhibitor, an indole inhibitor, a nicotinamide inhibitor, an urea inhibitor, a polyphenol inhibitor, or a thienopyrimidine carboxamide inhibitor, the SIRT1 inhibitor is a compound including naphthol, indole, nicotinamide, urea, polyphenol or thienopyrimidine carboxamide, respectively.

In embodiments, a nucleic acid encoding a SIRT1 protein is contacted with a DNA-editing agent thereby forming an edited SIRT1 nucleic acid. In embodiments, the edited SIRT1 nucleic acid expresses a SIRT1 protein with altered (e.g. decreased) activity or function. In embodiments, the edited SIRT1 nucleic acid does not express a SIRT1 protein. In embodiments, the DNA-editing agent is a short target nucleotide sequence, a transcription activator-like effector nuclease (TALEN) or a zinc finger nuclease (ZFN). In embodiments, the nucleic acid forms part of the genome of a cell. In embodiments, the nucleic acid is a genomic nucleic acid.

In one embodiment, the SIRT1 inhibitor is a naphthol inhibitor (i.e. a SIRT1 inhibitor comprising a naphthol moiety, alternatively referred to as a naphthalenol moiety or a hydroxy-naphthalene moiety). In one embodiment, the naphthol inhibitor is sirtinol, cambinol, splitomicin or salermide. In one embodiment, the naphthol inhibitor is sirtinol. "Sirtinol" as provided herein refers to 2-[[(2-Hydroxy-1-naphthalenyl)methylene]amino]-N-(1-phenylethyl) benzamide, and in the customary sense, refers to CAS Registry No. 410536-97-9.

In one embodiment, the naphthol inhibitor is cambinol. "Cambinol" as provided herein refers to 5-[(2-hydroxy-1-naphthyl)methyl]-2-mercapto-6-phenyl-4(3H)-pyrimidinone, and in the customary sense, refers to CAS Registry No. 14513-15-6. In one embodiment, the naphthol inhibitor is splitomicin. "Splitomicin" as provided herein refers to 1,2-dihydro-3H-naphtho[2,1-b]pyran-3-one, and in the customary sense, refers to CAS Registry No. 5690-03-9. In one embodiment, the naphthol inhibitor is salermide. "Salermide" as provided herein refers to N-[3-[[(2-hydroxy-1-naphthalenyl)methylene]amino]phenyl]-a-methyl-benzeneacetamide, and in the customary sense, refers to CAS Registry No. 1105698-15-4.

In one embodiment, the SIRT1 inhibitor is an indole inhibitor (i.e. a SIRT1 inhibitor comprising an indole moiety, including an indolinone moiety or tetrahydocargazole moiety). In one embodiment, the indole inhibitor is EX-527, bisindolylmaleimide, AC-93253, arylidenindolinone, indolinone, GW5074, RO31-8220 or tryptamine. In one embodiment, the indole inhibitor is EX-527. "EX-527" as provided herein refers to 6-chloro-2,3,4,9-tetrahydro-1H-carbazole-1-carboxamide, and in the customary sense, refers to CAS Registry No. 49843-98-3. In one embodiment, the indole inhibitor is bisindolylmaleimide. "Bisindolylmaleimide" as provided herein refers to 3-[1-[3-(dimethylamino)propyl]-1H-indol-3-yl]-4-(1H-indol-3-yl)-1H-pyrrole-2,5-dione, and in the customary sense, refers to CAS Registry No. 133052-90-1. In one embodiment, the indole inhibitor is AC-93253. "AC-93253" as provided herein in the customary sense, refers to CAS Registry No. 108527-83-9. In one embodiment, the indole inhibitor is arylidenindolinone. In one embodiment, the indole inhibitor is indolinone. "Indolinone" as provided herein refers in the customary sense, to CAS Registry No. 59-48-3. In one embodiment, the indole inhibitor is GW5074. "GW5074" as provided herein refers to 3-(3,5-dibromo-4-hydroxy-benzylidene)-5-iodo-1,3-dihydro-indol-2-one and in the customary sense, refers to CAS Registry No. 220904-83-6. In one embodiment, the indole inhibitor is RO31-8220. "RO31-8220" as provided herein refers to 2-{1-[3-(Amidinothio)propyl]-1H-indol-3-yl}-3-(1-methylindol-3-yl)maleimide methanesulfonate salt and in the customary sense, refers to CAS Registry No. 557521. In one embodiment, the indole inhibitor is tryptamine. "Trypamine" as provided herein refers to 2-(3-Indolyl) ethylamine, 3-(2-Aminoethyl)indole and in the customary sense, refers to CAS Registry No. 61-54-1.

In one embodiment, the SIRT1 inhibitor is a nicotinamide inhibitor (i.e. a SIRT1 inhibitor comprising a nicotidamide moiety). In one embodiment, the nicotinamide inhibitor is carbanicotinamide adenine dinucleotide. As provided herein carbanicotinamide adenine dinucleotide refers in the customary sense, to CAS Registry No. 112345-60-5.

In one embodiment, the SIRT1 inhibitor is an urea inhibitor (i.e. a SIRT1 inhibitor comprising a urea moiety). In one embodiment, the urea inhibitor is tenovin or suramin. In one embodiment, the urea inhibitor is tenovin. "Tenovin" as provided herein refers to N-[[[4-[[5-(dimethylamino)-1-oxopentyl]amino]phenyl]amino]thioxomethyl]-4-(1,1-dimethylethyl)-benzamide and in the customary sense, refers to CAS Registry No. 1011557-82-6. In one embodiment, the urea inhibitor is suramin. "Suramin" as provided herein has the empirical formula $C_{51}H_{34}N_6Na_6O_{23}S_6$ and in the customary sense, refers to CAS Registry No. 129-46-4.

In one embodiment, the SIRT1 inhibitor is a polyphenol inhibitor (i.e. a SIRT1 inhibitor comprising two or more phenol moieties). In one embodiment, the polyphenol inhibitor is biphenylpolyphenol, erbstatin, rottlerin or a rottlerin derivative. In one embodiment, the polyphenol inhibitor is biphenylpolyphenol. "Biphenylpolyphenol" as provided herein refers to the compound having the formula

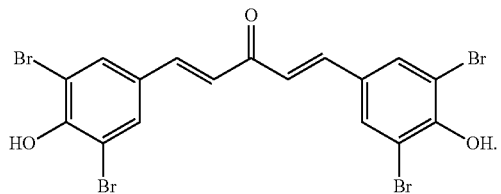 [SMILES: O=C(/C=C/c1cc(Br)c(O)c(Br)c1)/C=C/c1cc(Br)c(O)c(Br)c1]

In one embodiment, the polyphenol inhibitor is erbstatin. "Erbstatin" as provided herein refers to methyl 2,5-dihydroxycinnamate and in the customary sense, refers to CAS Registry No. 63177-57-1. In one embodiment, the polyphenol inhibitor is rottlerin. "Rottlerin" as provided herein refers to 3'-[(8-Cinnamoyl-5,7-dihydroxy-2,2-dimethyl-2H-1-benzopyran-6-yl)methyl]-2',4',6'-trihydroxy-5'-methylacetophenone and in the customary sense, refers to CAS Registry No. 82-08-6. In one embodiment, the polyphenol inhibitor is a rottlerin derivative. A "rotterlein derivative" as provided herein is a compound chemically derived from rottlerin.

In one embodiment, the SIRT1 inhibitor is a peptide inhibitor (i.e. a SIRT1 inhibitor that is a peptide). In one embodiment, the peptide inhibitor is a thioacetyllysine peptide, a fluoroacetyllysine peptide or a histone-3-lysine-9-thiosuccinyl (H3K9TSu) peptide. In one embodiment, the peptide inhibitor is a thioacetyllysine peptide. A thioacetyllysine peptide is known in the art and disclosed, for example, in Huhtiniemi, T. et al. J Med Chem 2011, 54: 6456-6468. In another embodiment, the peptide inhibitor is a fluoroacetyllysine peptide. A "fluoroacetyllysine peptide" as provided herein has the empirical formula $C_8H_{13}F_3N_2O_3$ and in the customary sense, refers to CAS Registry No. 10009-20-8. In one embodiment, the peptide inhibitor is histone-3-lysine-9-thiosuccinyl (H3K9TSu) peptide.

In another aspect, a method of increasing immune competence in a subject in need thereof is provided. The method includes administering a therapeutically effective amount of a SIRT1 inhibitor to a subject, thereby increasing immune competence in the subject. "Immune competence" as provided herein refers to the ability of an organism to produce an immune response following exposure to an antigen. The immune response is mediated by lymphocytes (e.g., T cells, B cells, NK cells) and immuno-proteins (e.g., antibodies, complement) and results in protection against the disease caused by said antigen. The immune competence of a subject may be compromised thereby resulting in the lack or deficiency of an immune response. The methods provided herein may be used to elicit an immune response or increase the efficiency of an immune response in a subject in need thereof, thereby increasing the immune competence of the subject. In one embodiment, the subject is an elderly subject. In one embodiment, the subject is an immuno-deficient subject. In one embodiment, the subject is an immuno-compromised subject. In one embodiment, the subject is an immuno-incompetent subject.

For the methods of increasing immune competence as provided herein any SIRT1 inhibitor capable of altering (e.g. decreasing) the activity or function of a SIRT1 protein, SIRT1 encoding nucleic acid, or SIRT1 polysaccharide is contemplated. In some embodiments, the SIRT 1 inhibitor is a small molecule or compound. In one embodiment, the SIRT 1 inhibitor is a naphthol inhibitor, an indole inhibitor, a nicotinamide inhibitor, an urea inhibitor, a polyphenol inhibitor, a thienopyrimidine carboxamide inhibitor, inauhzin, a peptide inhibitor or an antisense nucleic acid (e.g., siRNA, shRNA, miRNA). Where the SIRT1 inhibitor is a naphthol inhibitor, an indole inhibitor, a nicotinamide inhibitor, an urea inhibitor, a polyphenol inhibitor, or a thienopyrimidine carboxamide inhibitor, the SIRT1 inhibitor is a compound including or derived from naphthol, indole, nicotinamide, urea, polyphenol or thienopyrimidine carboxamide, respectively.

In one embodiment, the SIRT1 inhibitor is a naphthol inhibitor. In one embodiment, the naphthol inhibitor is sirtinol, cambinol, splitomicin or salermide. In one embodiment, the naphthol inhibitor is sirtinol. In one embodiment, the naphthol inhibitor is cambinol. In one embodiment, the naphthol inhibitor is splitomicin. In one embodiment, the naphthol inhibitor is salermide.

In one embodiment, the SIRT1 inhibitor is an indole inhibitor. In one embodiment, the indole inhibitor is EX-527, bisindolylmaleimide, AC-93253, arylidenindolinone, indolinone, GW5074, RO31-8220 or tryptamine. In one embodiment, the indole inhibitor is EX-527. In one embodiment, the indole inhibitor is bisindolylmaleimide. In one embodiment, the indole inhibitor is AC-93253. In one embodiment, the indole inhibitor is arylidenindolinone. In one embodiment, the indole inhibitor is indolinone. In one embodiment, the indole inhibitor is GW5074. In one embodiment, the indole inhibitor is RO31-8220. In one embodiment, the indole inhibitor is tryptamine.

In one embodiment, the SIRT1 inhibitor is a nicotinamide inhibitor. In one embodiment, the nicotinamide inhibitor is carbanicotinamide adenine dinucleotide.

In one embodiment, the SIRT1 inhibitor is an urea inhibitor. In one embodiment, the urea inhibitor is tenovin or suramin. In one embodiment, the urea inhibitor is tenovin. In one embodiment, the urea inhibitor is suramin.

In one embodiment, the SIRT1 inhibitor is a polyphenol inhibitor. In one embodiment, the polyphenol inhibitor is biphenylpolyphenol, erbstatin, rottlerin or a rottlerin derivative. In one embodiment, the polyphenol inhibitor is biphenylpolyphenol. In one embodiment, the polyphenol inhibitor is erbstatin. In one embodiment, the polyphenol inhibitor is rottlerin. In one embodiment, the polyphenol inhibitor is a rottlerin derivative.

In one embodiment, the SIRT1 inhibitor is a peptide inhibitor. In one embodiment, the peptide inhibitor is a thioacetyllysine peptide, a fluoroacetyllysine peptide or a histone-3-lysine-9-thiosuccinyl (H3K9TSu) peptide. In one embodiment, the peptide inhibitor is a thioacetyllysine peptide. In another embodiment, the peptide inhibitor is a fluoroacetyllysine peptide. In one embodiment, the peptide inhibitor is histone-3-lysine-9-thiosuccinyl (H3K9TSu) peptide.

The methods of treating or preventing a hematological disease in a subject in need thereof as provided herein include methods of administering a rejuvinated HSC to a subject. Provided herein are methods where the rejuvinated HSC is allowed to differentiate (e.g. in vitro) in the presence of appropriate growth factors to form for example, a red blood cell, a lymphoid cell or a myeloid cell. The red blood cell, the lymphoid cell or the myeloid cell may subsequently be administered to the subject, thereby treating the hematological disease. For the methods provided herein, the HSC may be isolated from a subject (e.g., from the bone marrow or peripheral blood) or the HSC may be derived in vitro from an iPSC or ES cell using established reprogramming methods well known in the art. Thus, in one aspect, a method of treating or preventing a hematological disease in a subject in need thereof is provided. The method includes isolating a hematopoietic stem cell (HSC) from a subject, thereby forming an isolated HSC. The isolated HSC is contacted with a SIRT1 inhibitor, thereby forming a rejuvinated HSC. The rejuvinated HSC is adminstered to the subject, thereby treating or preventing a hematological disease in the subject. In one embodiment, the rejuvinated HSC is allowed to divide prior to the administering of step (iii). In one embodiment, the isolating of step (i) includes isolating a somatic cell from the subject, reprogramming the somatic cell thereby forming an iPSC, and allowing the iPSC to differentiate thereby forming an isolated HSC.

In another aspect, a method of treating or preventing a hematological disease in a subject in need thereof is provided. The method includes isolating a hematopoietic stem cell (HSC) from a subject, thereby forming an isolated HSC. The isolated HSC is contacted with a SIRT1 inhibitor, thereby forming a rejuvinated HSC. The rejuvinated HSC is allowed to divide in the presence of lineage-specific growth factors (e.g., SCF, IL-3, IL-15), thereby forming a plurality of red blood cells, a plurality of lymphoid cells or a plurality of myeloid cells. The plurality of red blood cells, the plurality of lymphoid cells or the plurality of myeloid cells is adminstered to the subject, thereby treating or preventing a hematological disease in the subject. In one embodiment, the allowing of step (iii) includes forming a plurality of red blood cells. In another embodiment, the allowing of step (iii) includes forming a plurality of lymphoid cells. In another embodiment, the allowing of step (iii) includes forming a plurality of myeloid cells. In one embodiment, the isolating of step (i) includes isolating a somatic cell from the subject, reprogramming the somatic cell thereby forming an iPSC, and allowing the iPSC to differentiate thereby forming an isolated HSC.

In one embodiment, the isolating includes obtaining a biological sample from the subject and isolating the HSC from the biological sample. In one embodiment, the isolating includes obtaining a biological sample from the subject and isolating a somatic cell from the biological sample. In one embodiment, the biological sample is a blood sample or a bone marrow sample.

In one embodiment, the hematological disease is an age-related hematological disease. In another embodiment, the method is a method of preventing an age-related hematological disease.

The methods provided herein may be used for treating or preventing non-cancerous or cancerous hematological disease. Where the method of treating or preventing a hematological disease includes administering a therapeutically effective amount of a SIRT1 inhibitor to the subject, the disease is not a cancerous diseases. Thus, in one embodiment, the hematological disease is not a cancerous disease. Where the method of treating or preventing a hematological disease includes isolating a hematopoietic stem cell (HSC) from a subject, thereby forming an isolated HSC, contacting the isolated HSC with a SIRT1 inhibitor, thereby forming a rejuvinated HSC and administering the rejuvinated HSC to the subject, the disease may be a cancerous or non-cancerous diseases. Thus, in one embodiment, the hematological disease is a cancerous hematological disease or a non-cancerous hematological disease.

In one embodiment, the hematological disease is a red blood cell disease, a lymphoid disease or a myeloid disease. In another embodiment, the red blood cell disease is anemia. In another embodiment, the anemia is age-related anemia.

In another embodiment, the lymphoid disease is acute lymphocytic leukemia, chronic lymphocytic leukemia or lymphoma. In one embodiment, the lymphoid disease is age-related lymphocytopenia or lymphopenia.

In another embodiment, the myeloid disease is a pre-leukemic myeloid disease. In another embodiment, the pre-leukemic myeloid disease is an age-related pre-leukemic myeloid disease. In one embodiment, the pre-leukemic myeloid disease is a myelodysplastic syndrome or a chronic myeloproliferative disease. In one embodiment, the myelodysplastic syndrome is refractory anemia or refractory cytopenia. In another embodiment, the chronic myeloproliferative disease is polycythemia vera or essential thrombocythemia. In another embodiment, the myeloid disease is a leukemic myeloid disease. In one embodiment, the leukemic myeloid disease is acute myeloid leukemia, chronic myeloid leukemia, chronic neutrophilic leukemia or chronic eosinophilic leukemia.

As described above, for the methods of treating and preventing a hematological disease as provided herein any SIRT1 inhibitor capable of altering (e.g. decreasing) the activity or function of a SIRT1 protein, SIRT1 encoding nucleic acid, or SIRT1 polysaccharide is contemplated. In some embodiments, the SIRT1 inhibitor is a small molecule or compound. In one embodiment, the SIRT1 inhibitor is a naphthol inhibitor, an indole inhibitor, a nicotinamide inhibitor, an urea inhibitor, a polyphenol inhibitor, a thienopyrimidine carboxamide inhibitor, inauhzin, a peptide inhibitor or an antisense nucleic acid (e.g., siRNA, shRNA, miRNA). Where the SIRT1 inhibitor is a naphthol inhibitor, an indole inhibitor, a nicotinamide inhibitor, an urea inhibitor, a polyphenol inhibitor, or a thienopyrimidine carboxamide inhibitor, the SIRT1 inhibitor is a compound including or derived from naphthol, indole, nicotinamide, urea, polyphenol or thienopyrimidine carboxamide, respectively.

In one embodiment, the SIRT1 inhibitor is a naphthol inhibitor. In one embodiment, the naphthol inhibitor is sirtinol, cambinol, splitomicin or salermide. In one embodiment, the naphthol inhibitor is sirtinol. In one embodiment, the naphthol inhibitor is cambinol. In one embodiment, the naphthol inhibitor is splitomicin. In one embodiment, the naphthol inhibitor is salermide.

In one embodiment, the SIRT1 inhibitor is an indole inhibitor. In one embodiment, the indole inhibitor is EX-527, bisindolylmaleimide, AC-93253, arylidenindolinone, indolinone, GW5074, RO31-8220 or tryptamine. In one embodiment, the indole inhibitor is EX-527. In one embodiment, the indole inhibitor is bisindolylmaleimide. In one embodiment, the indole inhibitor is AC-93253. In one embodiment, the indole inhibitor is arylidenindolinone. In one embodiment, the indole inhibitor is indolinone. In one embodiment, the indole inhibitor is GW5074. In one embodiment, the indole inhibitor is RO31-8220. In one embodiment, the indole inhibitor is tryptamine.

In one embodiment, the SIRT1 inhibitor is a nicotinamide inhibitor. In one embodiment, the nicotinamide inhibitor is carbanicotinamide adenine dinucleotide.

In one embodiment, the SIRT1 inhibitor is an urea inhibitor. In one embodiment, the urea inhibitor is tenovin or suramin. In one embodiment, the urea inhibitor is tenovin. In one embodiment, the urea inhibitor is suramin.

In one embodiment, the SIRT1 inhibitor is a polyphenol inhibitor. In one embodiment, the polyphenol inhibitor is biphenylpolyphenol, erbstatin, rottlerin or a rottlerin derivative. In one embodiment, the polyphenol inhibitor is biphenylpolyphenol. In one embodiment, the polyphenol inhibitor is erbstatin. In one embodiment, the polyphenol inhibitor is rottlerin. In one embodiment, the polyphenol inhibitor is a rottlerin derivative.

In one embodiment, the SIRT1 inhibitor is a peptide inhibitor. In one embodiment, the peptide inhibitor is a thioacetyllysine peptide, a fluoroacetyllysine peptide or a histone-3-lysine-9-thiosuccinyl (H3K9TSu) peptide. In one embodiment, the peptide inhibitor is a thioacetyllysine peptide. In another embodiment, the peptide inhibitor is a fluoroacetyllysine peptide. In one embodiment, the peptide inhibitor is histone-3-lysine-9-thiosuccinyl (H3K9TSu) peptide.

In another aspect, a method of forming a red blood cell is provided. The method includes contacting a hematopoietic stem cell (HSC) with a SIRT1 inhibitor, thereby forming a rejuvenated HSC. And the rejuvenated HSC is allowed to divide, thereby forming a red blood cell. Where the rejuvinated HSC is allowed to divide, the HSC is cultured in the presence of appropriate growth factors known in the art to produce red blood cells. In one embodiment, the HSC is derived from an iPSC or an ES cell. In one embodiment, the HSC is derived from an iPSC. In one embodiment, the HSC is derived from an ES cell. In one embodiment the rejuvinated HSC is administered to a subject in need of treating or preventing a hematological disease. In one embodiment, the hematological disease is anemia. In one embodiment, the anemia is age-related anemia. In one embodiment, the contacting occurs in a subject. In another embodiment, the subject is an elderly subject. In one embodiment, the HSC is derived from a biological sample. In another embodiment, the biological sample is a blood sample or a bone marrow sample. In one embodiment, the contacting occurs in vitro. In another embodiment, after the contacting the rejuvenated HSC is administered to a subject.

In another aspect, a method of forming a lymphoid cell is provided. The method includes contacting a hematopoietic stem cell (HSC) with a SIRT1 inhibitor, thereby forming a rejuvenated HSC. And the rejuvenated HSC is allowed to divide, thereby forming a lymphoid cell. Where the rejuvinated HSC is allowed to divide, the HSC is cultured in the presence of appropriate growth factors known in the art to produce lymphoid cells. In one embodiment, the HSC is derived from an iPSC or an ES cell. In one embodiment, the HSC is derived from an iPSC. In one embodiment, the HSC is derived from an ES cell. In one embodiment the rejuvinated HSC is administered to a subject in need of treating or preventing a hematological disease. In one embodiment, the hematological disease is acute lymphocytic leukemia, chronic lymphocytic leukemia or lymphoma. In one embodiment, the hematological disease is age-related lymphocytopenia or lymphopenia. In one embodiment, the contacting occurs in a subject. In another embodiment, the subject is an elderly subject. In one embodiment, the HSC is derived from a biological sample. In another embodiment, the biological sample is a blood sample or a bone marrow sample. In one embodiment, the contacting occurs in vitro. In another embodiment, after the contacting the rejuvenated HSC is administered to a subject.

In another aspect, a method of forming a myeloid cell is provided. The method includes contacting a hematopoietic stem cell (HSC) with a SIRT1 inhibitor, thereby forming a rejuvenated HSC. And the rejuvenated HSC is allowed to divide, thereby forming a myeloid cell. Where the rejuvinated HSC is allowed to divide, the HSC is cultured in the presence of appropriate growth factors known in the art to produce myeloid cells. In one embodiment, the HSC is derived from an iPSC or an ES cell. In one embodiment, the HSC is derived from an iPSC. In one embodiment, the HSC is derived from an ES cell. In one embodiment the rejuvinated HSC is administered to a subject in need of treating or preventing a hematological disease. In one embodiment, the hematological disease is a pre-leukemic myeloid disease. In another embodiment, the hematological disease is a leukemic myeloid disease. In one embodiment, the contacting occurs in a subject. In another embodiment, the subject is an elderly subject. In one embodiment, the HSC is derived from a biological sample. In another embodiment, the biological sample is a blood sample or a bone marrow sample. In one embodiment, the contacting occurs in vitro. In another embodiment, after the contacting the rejuvenated HSC is administered to a subject.

In one embodiment, the SIRT1 inhibitor is a naphthol inhibitor. In one embodiment, the naphthol inhibitor is sirtinol, cambinol, splitomicin or salermide. In one embodiment, the naphthol inhibitor is sirtinol. In one embodiment, the naphthol inhibitor is cambinol. In one embodiment, the naphthol inhibitor is splitomicin. In one embodiment, the naphthol inhibitor is salermide.

In one embodiment, the SIRT1 inhibitor is an indole inhibitor. In one embodiment, the indole inhibitor is EX-527, bisindolylmaleimide, AC-93253, arylidenindolinone, indolinone, GW5074, RO31-8220 or tryptamine. In one embodiment, the indole inhibitor is EX-527. In one embodiment, the indole inhibitor is bisindolylmaleimide. In one embodiment, the indole inhibitor is AC-93253. In one embodiment, the indole inhibitor is arylidenindolinone. In one embodiment, the indole inhibitor is indolinone. In one embodiment, the indole inhibitor is GW5074. In one embodiment, the indole inhibitor is RO31-8220. In one embodiment, the indole inhibitor is tryptamine.

In one embodiment, the SIRT1 inhibitor is a nicotinamide inhibitor. In one embodiment, the nicotinamide inhibitor is carbanicotinamide adenine dinucleotide.

In one embodiment, the SIRT1 inhibitor is an urea inhibitor. In one embodiment, the urea inhibitor is tenovin or suramin. In one embodiment, the urea inhibitor is tenovin. In one embodiment, the urea inhibitor is suramin.

In one embodiment, the SIRT1 inhibitor is a polyphenol inhibitor. In one embodiment, the polyphenol inhibitor is biphenylpolyphenol, erbstatin, rottlerin or a rottlerin derivative. In one embodiment, the polyphenol inhibitor is biphenylpolyphenol. In one embodiment, the polyphenol inhibitor is erbstatin. In one embodiment, the polyphenol inhibitor is rottlerin. In one embodiment, the polyphenol inhibitor is a rottlerin derivative.

In one embodiment, the SIRT1 inhibitor is a peptide inhibitor. In one embodiment, the peptide inhibitor is a thioacetyllysine peptide, a fluoroacetyllysine peptide or a histone-3-lysine-9-thiosuccinyl (H3K9TSu) peptide. In one embodiment, the peptide inhibitor is a thioacetyllysine peptide. In another embodiment, the peptide inhibitor is a fluoroacetyllysine peptide. In one embodiment, the peptide inhibitor is histone-3-lysine-9-thiosuccinyl (H3K9TSu) peptide.

III. Hematopoietic Stem Cells

Provided herein are, inter alia, cellular compositions useful for treating or preventing hematological disease. In one aspect, a hematopoietic stem cell (HSC) including an exogenous SIRT1 inhibitor is provided. In one embodiment, the HSC is derived from an iPSC or an ES cell.

In one embodiment, the exogenous SIRT1 inhibitor is a naphthol inhibitor. In one embodiment, the naphthol inhibitor is sirtinol, cambinol, splitomicin or salermide. In one embodiment, the naphthol inhibitor is sirtinol. In one embodiment, the naphthol inhibitor is cambinol. In one embodiment, the naphthol inhibitor is splitomicin. In one embodiment, the naphthol inhibitor is salermide.

In one embodiment, the exogenous SIRT1 inhibitor is an indole inhibitor. In one embodiment, the indole inhibitor is EX-527, bisindolylmaleimide, AC-93253, arylidenindolinone, indolinone, GW5074, RO31-8220 or tryptamine. In one embodiment, the indole inhibitor is EX-527. In one embodiment, the indole inhibitor is bisindolylmaleimide. In one embodiment, the indole inhibitor is AC-93253. In one embodiment, the indole inhibitor is arylidenindolinone. In one embodiment, the indole inhibitor is indolinone. In one embodiment, the indole inhibitor is GW5074. In one embodiment, the indole inhibitor is RO31-8220. In one embodiment, the indole inhibitor is tryptamine.

In one embodiment, the exogenous SIRT1 inhibitor is a nicotinamide inhibitor. In one embodiment, the nicotinamide inhibitor is carbanicotinamide adenine dinucleotide.

In one embodiment, the exogenous SIRT1 inhibitor is an urea inhibitor. In one embodiment, the urea inhibitor is tenovin or suramin. In one embodiment, the urea inhibitor is tenovin. In one embodiment, the urea inhibitor is suramin.

In one embodiment, the exogenous SIRT1 inhibitor is a polyphenol inhibitor. In one embodiment, the polyphenol inhibitor is biphenylpolyphenol, erbstatin, rottlerin or a rottlerin derivative. In one embodiment, the polyphenol inhibitor is biphenylpolyphenol. In one embodiment, the polyphenol inhibitor is erbstatin. In one embodiment, the polyphenol inhibitor is rottlerin. In one embodiment, the polyphenol inhibitor is a rottlerin derivative.

In one embodiment, the exogenous SIRT1 inhibitor is a peptide inhibitor. In one embodiment, the peptide inhibitor is a thioacetyllysine peptide, a fluoroacetyllysine peptide or a histone-3-lysine-9-thiosuccinyl (H3K9TSu) peptide. In one embodiment, the peptide inhibitor is a thioacetyllysine peptide. In another embodiment, the peptide inhibitor is a fluoroacetyllysine peptide. In one embodiment, the peptide inhibitor is histone-3-lysine-9-thiosuccinyl (H3K9TSu) peptide.

IV. Examples

1. Example I

Applicants have demonstrated that SIRT1 plays a crucial role in pathobiology of chronic myelogenous leukemia (CML), a HSC disease caused by BCR-ABL oncogene. (Melo, J. V. & Barnes, D. J., *Nat Rev Cancer* 7, 441-453 (2007)) SIRT1 is activated by BCR-ABL transformation of hematopoietic stem/progenitor cells, and promotes leukemogenesis and leukemic stem cell resistance to BCR-ABL tyrosine kinase inhibitor imatinib. (Yuan, H. et al., *Blood* 119, 1904-1914 (2012); Li, L. et al., *Cancer Cell* 21, 266-281 (2012)) In addition, Applicants have shown that SIRT1 promotes de novo acquisition of BCR-ABL mutations for drug resistance in CML cells upon BCR-ABL inhibitor treatment, in association with the ability of SIRT1 to enhance error-prone NHEJ repair through deacetylating Ku70, a central factor for such repair. (Wang, Z. et al., *Oncogene* 32, 589-598 (2013))

Although mechanistically unclear, CR can significantly improve HSC functions in aged mice. (Chen, J. et al., *Experimental hematology* 31, 1097-1103 (2003)) It is also known that aged HSCs can be rejuvenated by inhibiting Cdc42, which restores acetylation of histone H4 K16 to a status seen in young mice. (Florian, M. C. et al., *Cell stem cell* 10, 520-530 (2012)) Over-expression of polycomb group protein Ezh2 extends HSC repopulation capacity and prevents them from rapid exhaustion. (Kamminga, L. M. et al., *Blood* 107, 2170-2179 (2006)) These studies suggest possible involvement of epigenetic regulation of HSC aging. In a gene profiling study, aged HSCs exhibit epigenetic dysregulation, particularly, with down regulation of sirtuin deacetylases SIRT2, SIRT3 and SIRT7. (Chambers, S. M. et al., *PLoS Biol* 5, e201 (2007)) However, reduction of these sirtuins contrasts the reduction of H4 K16 acetylation in aging HSCs, (Florian, M. C. et al., *Cell stem cell* 10, 520-530 (2012)) suggesting that other deacetylases may be responsible for the deacetylation.

To address the potential role of SIRT1 in HSC aging, Applicants have used serial bone marrow transplantation (BMT) to study the effect of SIRT1 knockout. Unexpectedly, Applicants found that SIRT1 knockout inhibits HSC aging phenotypes by suppressing age-dependent HSC expansion, promoting balanced lineage differentiation, blocking development of leukemia and lymphoma, and prolonging mouse survival. Applicants found that SIRT1 expression is up-regulated in aging mouse HSCs; but surprisingly SIRT1 knockout leads to suppression of a large number of genes that are activated in aging HSCs, particularly those for mitochondrial oxidative phosphorylation that may be responsible for generation of reactive oxygen species (ROS) and oxidative stress.

Characterization of HSCs in BALB/c Mice.

Figure 1:
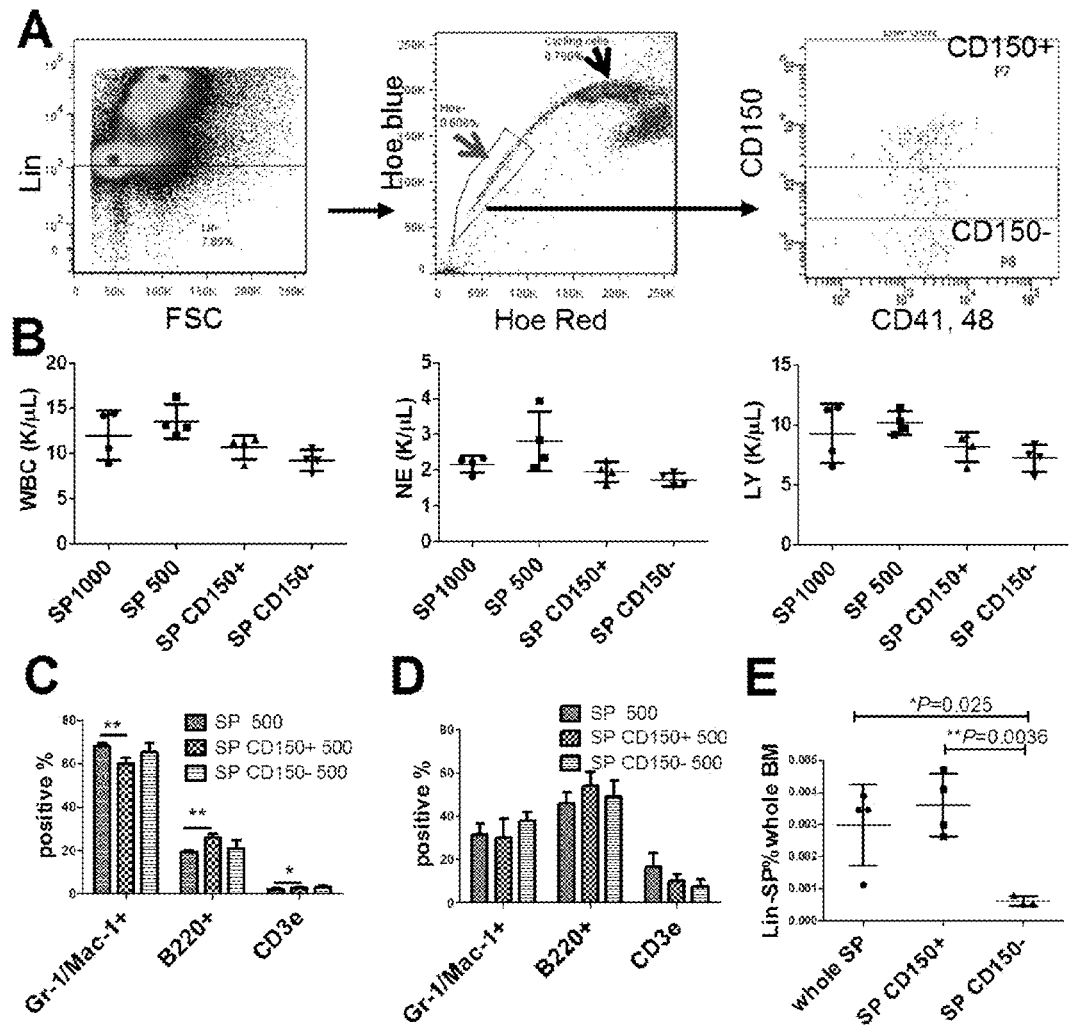
FIG. 1 Characterization of hematopoietic stem cells in BALB/c mice. (A) Sorting scheme for Lin− side population (SP, arrow), and further separation with CD150. Cycling cells indicated by black arrow. (B-D) Comparison of long term reconstitution of 500 and 1000 SP cells (spleen cells), and 500 each CD150$^+$SP and CD150-SP cells. B, blood cells were counted 4 months after transplantation. N=4 each. Note that all 4 control mice reconstituted with cycling cells died in three weeks. C,D, lineage distribution in bone marrow (C)

Applicants backcrossed SIRT1 constitutive knockout mice (Cheng, H. L. et al., *Proc Natl Acad Sci USA* 100, 10794-10799 (2003)) to both C57BL/6 and BALB/c strains for 9 generations. SIRT1$^{-/-}$ mice were found not viable in C57BL/6 strain after such backcross; but in BALB/c strain, a portion of such mice can survive through adulthood and were used to study HSC aging. Unlike HSCs in C57BL/6 mice, HSCs are less characterized in BALB/c strain. Side population (SP) analysis based on Hoechst dye exclusion is a well-adopted method for HSC analysis in different genetic background. (Goodell, M. A. et al., *Nat Med* 3, 1337-1345 (1997)) Furthermore, recent studies have showed that aging HSCs tend to express CD150$^{hi}$ cells, particularly in the SP$^{lo}$ fraction, favoring myeloid-biased differentiation during aging. (Challen, G. A. et al., *Cell stem cell* 6, 265-278 (2010)) Applicants first would like to validate HSC identity by SP in BALB/c mice. Using 3-month old BALB/c mice, Applicants sorted Lin-SP cells without or with CD150 separation (FIG. 1A). Long term reconstitution was found in all 16 mice transplanted with 500 or 1000 SP cells regardless of CD150 enrichment; in contrast, all 4 control recipient mice transplanted with 10,000 cycling cells each died in three weeks (p=0.0002), confirming HSCs are exclusively in SP fraction in BALB/c strain. Differential blood cell counts did not show significant difference among different groups of SP transplants (FIG. 1B). Compared to whole SP cells, CD150$^+$ SP cells from the young donors showed moderately increased B220$^+$cell output in bone marrow but not in blood or spleen (FIG. 1C,D and not shown). Interestingly, Applicants found that donor CD150$^-$ SP cells were significantly less efficient in reconstituting recipient bone marrow SP cells than donor CD150$^+$ SP or whole SP cells (FIG. 1E). This is perhaps because CD150$^-$ SP cells may exhaust faster during reconstitution process, as CD150$^-$ SP cells are known to be more proliferative than CD150$^+$ SP cells. (Weksberg, D. C. et al., *Blood* 111, 2444-2451 (2008)) Alternatively, CD150$^-$ SP cells may be less efficiently homing to bone marrow. In spite of this difference, both CD150$^+$ and CD150$^-$ SP cells are long term engrafting HSCs, in line with a previous report. (Weksberg, D. C. et al., *Blood* 111, 2444-2451 (2008))

SIRT1 Knockout Inhibits HSC Expansion During Aging in BALB/c Mice.

Several groups including ourselves showed that SIRT1 knockout does not affect adult mouse hematopoiesis at least in young adult mice. (Yuan, H. et al., *Blood* 119, 1904-1914 (2012); Leko, V. et al., *Blood* 119, 1856-1860 (2012); Narala, S. R. et al., *Molecular biology of the cell* 19, 1210-1219 (2008)) However, in a serial BMT study with original donors at the age of 3 months, Applicants surprisingly noted that in the third round BMT recipients, mice receiving SIRT1$^{-/-}$ bone marrow cells outlived those receiving wild type cells over one year period (not shown). This contrasts previous findings that SIRT1 promotes genome stability and loss of SIRT1 is expected to reduce lifespan in normal cells, (Oberdoerffer, P. et al., *Cell* 135, 907-918 (2008); Wang, R. H. et al., *Cancer Cell* 14, 312-323 (2008)) and suggests likely an unusual role of SIRT1 in HSC functions. This finding prompted Applicants to more systematically examine the impact of SIRT1 knockout on HSC aging. Applicants compared 16-20 month old SIRT1$^{-/-}$ (OKO) vs old SIRT1$^{+/+}$ (OWT) littermates, with young wild type (YWT) BALB/c mice as controls. Applicants found that there was no significant difference in differential blood cell counts between OWT vs YWT (FIG. 2A), but the lineage staining showed that OWT had moderately increased myeloid and reduced lymphoid output in bone marrow (FIG. 2B), consistent with a previous report that the BALB/c mice only have moderately biased lineage differentiation with age. (Cho, R. H. et al., *Blood* 111, 5553-5561 (2008)) Applicants found that OKO mice had significantly increased neutrophil output in both blood and bone marrow (FIG. 2A,B). This may be a neutrophilic response to chronic inflammation frequently seen in OKO mice that suffer from ophthalmia-like conditions with increased ocular discharge. (Cheng, H. L. et al., *Proc Natl Acad Sci USA* 100, 10794-10799 (2003)) Applicants found that OWT BALB/c mice expanded the HSC pool by an average of about 6 folds over YWT mice, similar to that seen in aging C57BL/6 mice; (Morrison, S. J. et al., *Nat Med* 2, 1011-1016 (1996)) strikingly, SIRT1 knockout inhibited this age-dependent HSC expansion (FIG. 2C). In line with moderate lineage differentiation change, CD150$^+$ SP cells were similar among YWT, OWT and OKO mice, with an average around 60% of SP each (not shown) as reported. (Weksberg, D. C. et al., *Blood* 111, 2444-2451 (2008))

SIRT1 Knockout Inhibited Skewed Lineage Differentiation in the 1$^{st}$ Round BMT Recipients.

Serial BMT has long been used to study HSC aging. (Rossi, D. J. et al., *Cell* 132, 681-696 (2008)) Applicants examined the effect of SIRT1 knockout on HSC aging in the first round BMT recipients. For easier tracking of serial BMT, Applicants used the following number codes: W—X—Y—Z, W for the age (month) of original donors, X for the age (month) of 1$^{st}$ round BMT recipients, Y for the age (month) of 2$^{nd}$ round BMT recipients, and Z for the age (month) of 3$^{rd}$ round BMT recipients. In 14-8 series (14-month old donors and recipients analyzed at 8 months after BMT), mice receiving wild type bone marrow cells exhibited significant lower total white blood cell and lymphocyte counts in peripheral blood than recipients with SIRT1$^{-/-}$ cells (FIG. 3A). In 20-10 series (20-month old donors and recipients analyzed 10 month after BMT), the skewed lineage differentiation was even more significant in some recipients with wild type cells: at the time of this submission, two out of ten mice exhibiting 10 fold reduction in B220$^+$ cells in blood and substantially increased Mac1$^+$ cells (83-91%) as compared to recipients with SIRT1$^{-/-}$ cells in which all (16 mice) exhibited normal blood phenotypes (FIG. 3B). Similar to aging donor mice, SP population was expanded more in recipients with wild type cells than with SIRT1 knockout cells (FIG. 3C). In line with skewed lineage differentiation, Applicants found that CD150$^-$ SP cells were significantly increased to over 80% in recipients with OWT cells, whereas CD150$^+$ SP cells in mice with OKO cells remained around 60% (FIG. 3D). These results are consistent with the previous finding that increased CD150$^+$ SP fraction favors myeloid differentiation during aging, (Challen, G. A. et al., *Cell stem cell* 6, 265-278 (2010)) and show that loss of SIRT1 inhibits skewed lineage differentiation during HSC aging.

SIRT1 Knockout Inhibited Hematological Malignancies in the 2$^{nd}$ and 3$^{rd}$ Round BMT Recipients.

Aging HSCs may contribute to pathophysiologies of blood cells, particularly anemia and hematological malignancies. (Rossi, D. J. et al., *Cell* 132, 681-696 (2008)) Applicants found that in both 2$^{nd}$ and 3$^{rd}$ round BMT, mice receiving wild type marrow cells were succumbed to frequent acute leukemia or lymphoma and occasional anemia; in contrast, mice receiving SIRT1 knockout cells were healthy. In 14-19-Y series, mice receiving wild type cells lived much shorter life than those receiving SIRT1 knockout cells (FIG. 4A), with splenomegaly and splenic lymphoma nodules clearly visible on some of the mice (FIG. 4B), and lymphoma histology (not shown) was confirmed. Starting 2 months after transplantation, abnormally differentiated cells were identified in the peripheral blood of many mice receiving wild type cells. These abnormal cells expressed intermediate levels of both lymphoid B220 and myeloid Mac1 markers, constituting an unusual fraction of immature cells on flow cytometric profile (FIG. 3C). Immunotyping of these cells showed that they were CD43$^+$CD19$^+$CD127$^+$, suggesting likely a blockage of B-cell development at the pro to pre-B stage. In another 2$^{nd}$ round BMT series 14-8-14, mice with wild type cells were subcombed to acute myeloid leukemia (AML), but with fully-developed B220 and Mac1 double positive cells (FIG. 4D,E). These B220$^+$Mac1$^+$ cells were found to be CD43$^+$CD19$^-$, suggesting likely a blockage at the pre-ProB stage (FIG. 4E). B220$^+$Mac1$^+$ myeloid leukemic cells with lymphoid characteristics were previously reported in a mouse AML model mediated by CALM/AF10, in which B220$^+$Mac1$^+$ cells suffer from V(D)J recombination defect. (Deshpande, A. J. et al., *Cancer Cell* 10, 363-374 (2006)) Similarly, Applicants found that B220$^+$Mac1$^+$ cells in Applicants' model retained the germline D-J allele (FIG. 4F), indicating the unproductive V(D)J recombination. Consistent with the phenotype in the 2$^{nd}$ BMT, Applicants found that mice receiving wild type cells in the 3$^{rd}$ BMT series 14-8-6-5 also developed AML characterized by B220$^+$Mac1$^+$ leukemic cells with a blockage at the pre-ProB stage (not shown). By genotyping peripheral blood and bone marrow cells, Applicants confirmed that mice receiving SIRT1$^{-/-}$ cells were indeed reconstituted with SIRT1$^{-/-}$ cells (not shown), further supporting the effect of SIRT1 knockout on inhibiting HSC aging and development of hematological malignancies. Given that both AML with lymphoid characteristics and lymphoma occur in the 2$^{nd}$ and 3$^{rd}$ BMT mice, it is likely that oncogenic lesions, genetic and/or epigenetic, may be acquired in HSCs during the process of skewed lineage determination or even early, leading to subsequent clonal expansion for malignancies. Together, the results show that BALB/c HSCs display stepwise changes of aging from HSC expansion, skewed lineage differentiation to hematological malignancies in serial BMT, and SIRT1 plays crucial roles in regulating these steps. This model also will provide an excellent tool for dissecting epigenetic changes of HSC aging in these steps.

Gene Expression Profiling of Aging HSCs and Effect of SIRT1 Knockout.

To gain insight into HSC aging, Applicants carried out microarray gene expression analysis of sorted Lin-SP HSCs from 4 young (10 weeks) BALB/c mice, and 2 each of old wild type and SIRT1$^{-/-}$ mice (16 to 20 months), using Affymetrix Mouse Genome 430 2.0 gene chips. Briefly, RNA of sorted SP cells was extracted with Arcturus PicoPure RNA Isolation kit. After quality control, RNA was subjected to amplification and cDNA synthesis using WT-Ovation One-Direct RNA Amplification System (NuGEN). Purified and quality-checked cDNA was then used for hybridization reaction on gene chips. Array data were processed by Partek Gene Expression Workflow. As shown in FIG. 5A, hierarchical clustering of young vs old mice showed that a large number of genes exhibited increased expression in OWT mice. But to Applicants' surprise, SIRT1 knockout partially restored gene expression pattern to YWT by repressing a large number of activated genes instead of de-repressing those repressed genes. This apparently contrasts that SIRT1 generally represses gene transcription by histone deacetylation in non-hematopoietic cells. (Oberdoerffer, P. et al., *Cell* 135, 907-918 (2008))

Gene Ontology and Ingenuity Pathways Analysis of the array data both revealed cell cycle as a top canonical pathway change in OWT vs YWT mice, including the increase of cyclin Dl expression in OWT mice (not shown), consistent with the observed expansion of aging SP HSCs. Using gene set enrichment analysis (GSEA) (Subramanian, A. et al., *Proc Natl Acad Sci USA* 102, 15545-15550 (2005)), Applicants found that TGF-β pathway was enriched in OWT mice compared to YWT (FIG. 5B). TGF-β signaling pathway plays a critical role in driving proliferation of myeloid-biased HSCs during aging. (Challen, G. A. et al., *Cell stem cell* 6, 265-278 (2010)) Intriguingly Applicants found that genes for Parkinson's and Huntington's diseases were among the most enriched in OWT cells as compared to OKO cells (FIG. 5C). Although precise connection of these age-dependent neurodegenerative disorders and HSC aging is not clear, most of these neurodegenerative genes that were enriched in OWT SP cells were involved in mitochondrial oxidative phosphorylation (OXPHOS), including numerous factors for complexes I to IV and ATP synthetase of the electron transport chain (FIG. 5D). However, no changes in Krebs cycle genes were noted, suggesting SIRT1 loss may selectively inactivate OXPHOS genes, but not overall gene expression for mitochondrial biogenesis, in HSCs. Increased OXPHOS leads to increased production of ATP accompanied by increased generation of reactive oxygen species (ROS) that has been postulated to increase cellular oxidative stress, and contribute to HSC aging. (Rossi, D. J. et al., *Cell* 132, 681-696 (2008)) Applicants' finding that SIRT1 loss suppressed OXPHOS and deterred the HSC aging coincides with the free radical hypothesis of aging. (Harman, D., *J Gerontol* 11, 298-300 (1956)) Noticeably, it has been shown that markers for oxidizied proteins and lipids are reduced in the brain of SIRT1 deficient mice, (Li, Y. et al., *Cell Metab* 8, 38-48 (2008)) suggesting reduced oxidative stress in the brain, in line with Applicants' findings. In addition, WNT signaling pathway was found enriched in OWT cells (FIG. 5E), consistent with their increased cell proliferation.

Applicants found that SIRT1 expression was increased in OWT compared to YWT SP cells on the array, which was confirmed by real-time PCR (FIG. 5F). Expression changes of several other genes in response to SIRT1 knockout were also confirmed, including SIRT1 downstream effector mGSK3 involving in WNT pathway and electron transport chain complex I factors Ndufb5 and Ndufa1 (FIG. 5G and not shown).

Opposing Roles of SIRT1 and LSD1 in DNA Damage Repair and Mutation Acquisition.

Although it is unclear how SIRT1 knockout led to repression of a large number of genes in aged HSCs, Applicants' recent studies of SIRT1 in cultured cells have identified a new mode of epigenetic stress response mediated by SIRT1 that may provide insight of SIRT1 functions in HSCs. In the CML acquired resistance model Applicants developed, (Yuan, H. et al., *J Biol Chem* 285, 5085-5096 (2010)) KCL-22 CML cells rapidly acquire T315I BCR-ABL kinase domain mutation upon imatinib treatment. Using chromatin immunoprecipitation (ChIP) analysis, Applicants found that SIRT1 presence on the ABL exon 5 where T315I mutation occurs was increased quickly after 12 h imatinib treatment and further increased towards 48 h, whereas Ku70 presence remained constant throughout 48 h (FIG. 6). Surprisingly, lysine specific demethylase LSD1 was also present on the locus but was reduced after imatinib treatment. LSD1 is a monoamine oxidase homolog that demethylates histone H3 K4 and K9 (Shi, Y. et al., *Cell* 119, 941-953 (2004); Metzger, E. et al., *Nature* 437, 436-439 (2005); Lee, M. G. et al., *Nature* 437, 432-435 (2005)) and functions to repress or activate gene expression (Wang, J. et al., *Nature* 446, 882-887 (2007); Whyte, W. A. et al., *Nature* 482, 221-225

(2012)). LSD1 also demethylates nonhistone protein DNA methyltransferase 1 for maintenance of global DNA methylation (Wang, J. et al., *Nat Genet* 41, 125-129 (2009)) and p53 for regulating transcription and cell survival (Huang, J. et al., *Nature* 449, 105-108 (2007)).

To address functions of LSD1 vs SIRT1 in CML cells, Applicants knocked down these genes. LSD1 knockdown increased histone H3K4 dimethylation as expected, but did not change Ku70 or SIRT1 expression (FIG. 7A). Using a chromatin-based NHEJ repair assay Applicants developed, (Wang, Z. et al., *Oncogene* 32, 589-598 (2013)) Applicants found that whereas SIRT1 knockdown reduced NHEJ repair, LSD1 knockdown increased the repair, and double knockdown neutralized the effect from individual knockdown (FIG. 7B). In spite of inhibiting cell growth and inducing moderate apoptosis (not shown), LSD1 knockdown increased formation of imatinib-resistant soft-agar colonies (FIG. 7C), opposing to the effect of SIRT1 inhibition. (Wang, Z. et al., *Oncogene* 32, 589-598 (2013)) These results suggest that LSD1 counteracts SIRT1 function for NHEJ repair and mutation acquisition in CML cells.

To explore the mechanisms, Applicants used immunoprecipitation (IP) assay to examine SIRT1, LSD1 and Ku70 interaction. Applicants found that LSD1 interacted with Ku70 but their interaction was reduced in response to imatinib treatment (FIG. 8A). In contrast, SIRT1 interaction with Ku70 was rapidly enhanced in response to imatinib, and even after the total SIRT1 level was partially reduced with 48 h drug treatment (Yuan, H. et al., *Blood* 119, 1904-1914 (2012)) (FIG. 8A). Similarly, treatment with hydrogen peroxide or DNA damage agent camptothecin also led to the switch of LSD1/SIRT1 interaction with Ku70 (FIG. 8B). These results suggest that the change of SIRT1 and LSD1 binding to Ku70 may be a cellular response to stress (therapeutic or oxidative) and DNA damage, and may underlie the dynamics of SIRT1 and LSD1 binding on the BCR-ABL chromatin locus and perhaps other loci in the cells.

The above results also indicate that LSD1 and SIRT1 may competitively bind to Ku70. To further examine this possibility, Applicants transfected 293 cells with varying amount of Flag tagged SIRT1 and HA tagged LSD1 along with the constant amount of Myc tagged Ku70. Myc-Ku70 was immunoprecipitated and probed for SIRT1 and LSD1 binding. Applicants found that increased expression of SIRT1 outcompeted LSD1, and conversely increased LSD1 expression outcompeted SIRT1, for Ku70 binding (FIG. 9). LSD1 also outcompeted SIRT1 for binding to a mutant Ku70 ($\Delta$SAP Ku70) with the deletion of a negative regulatory domain for LSD1 binding (detailed in next paragraph)

Applicants then determined the domains of Ku70 interacting with SIRT1 and LSD1, respectively. Applicants made a series of Myc-Ku70 truncation constructs for transfection in 293 cells and IP analysis. As shown in FIG. 10, Ku70 core domain (262-464) primarily mediated its interaction with SIRT1, whereas Ku70 N-terminus (1-257) served as a major repression domain and the nuclear localization signal (NLS)/linker region (464-573) as a positive regulation domain for this interaction. Consistent with the competitive binding of SIRT1 and LSD1 with Ku70, Applicants found that Ku70 core was also the major domain interacting with LSD1, in addition to the Ku70 N-terminus. Interestingly, the C-terminal SAP domain (574-609) was a strong repression domain for LSD1 interaction, and $\Delta$SAP Ku70 mutant preferentially bound with LSD1 as shown in FIG. 9. Together, Applicants' molecular studies suggest that SIRT1 and LSD1 play opposing roles in regulating certain chromatin events such as DNA repair and mutation acquisition, in part through competitive binding to Ku70. Interestingly, Ku70 also regulates transcription. (Giffin, W. et al., *Nature* 380, 265-268 (1996); Hoff, C. M. et al., *Proc Natl Acad Sci USA* 91, 762-766 (1994)) It is possible that knockout of SIRT1 may enhance the chromatin recruitment of LSD1 for transcriptional repression in HSCs, which will be explored in this proposal. In addition, Ku70 mediated NHEJ is the major DNA damage repair pathway in HSCs. (Mohrin, M. et al., *Cell stem cell* 7, 174-185 (2010)) Applicants will explore how epigenetic regulation of NHEJ activity affects mutation accumulation in aging HSCs.

In summary, Applicants' data show that HSCs of BALB/c mice exhibit step-wise aging process, with HSC expansion in mice undergoing physiological aging, then skewing of lineage potential in the $1^{st}$ round BMT recipients, and followed by hematological malignancies in the $2^{nd}$ round BMT recipients. Knockout of SIRT1 potently inhibits HSC aging phenotypes in all these steps. SIRT1 knockout partially restores transcriptome profile of aged HSCs to that of young HSCs, mainly by repressing activated genes in aged HSCs. Lysine modifiers LSD1 and SIRT1 competitively interact with Ku70, particularly under oxidative and DNA damage stress, which underlie DNA damage repair and mutation acquisition.

Characterization of Epigenetic Determinants of Self-renewal and Differentiation for HSC Aging.

Although intrinsic dysregulation of transcriptome has been recognized in alteration of self-renewal and lineage specification in aged HSCs, (Rossi, D. J. et al., *Proc Natl Acad Sci USA A* 102, 9194-9199 (2005); Chambers, S. M. et al., *PLoS Biol* 5, e201 (2007)) crucial epigenetic regulatory determinants underlying such dysregulation are not clear. Aged HSCs undergo deacetylation of histone H4 K16, and restoration of H4 K16 acetylation underlies rejuvenation of aging HSCs. (Florian, M. C. et al., *Cell stem cell* 10, 520-530 (2012)) H4 K16 is a preferred histone substrate of SIRT1. (Imai, S. et al., *Nature* 403, 795-800 (2000)) In line with these, Applicants' data showed that SIRT1 is upregulated in aged HSCs and SIRT1 knockout deters HSC aging, suggesting likely a critical role of SIRT1 in transcriptional reprogramming and functional regulation in aging HSCs once it is activated. This is supported by array data showing selective inactivation of OXPHOS genes, among others, in OKO HSCs. Applicants' identification of competitive binding of Ku70 by SIRT1 and LSD1 suggests another mode of epigenetic control of transcriptional regulation. Ku70 is one of the most abundant mammalian cellular proteins. (Lieber, M. R. et al., *Nature reviews* 4, 712-720 (2003)) It has been shown that Ku70 can bind to gene regulatory sequences and regulate transcription in a DNA damage repair-independent manner. (Giffin, W. et al., *Nature* 380, 265-268 (1996); Hoff, C. M. et al., *Proc Natl Acad Sci USA* 91, 762-766 (1994)) Alternating recruitment of deacetylase SIRT1 vs demethylase LSD1 by Ku70 may differentially remodel local chromatin architecture to regulate DNA repair and if at gene regulatory regions, affect transcription. Applicants speculate that loss of SIRT1 could allow Ku70 recruitment of LSD1 into regulatory domains of certain genes, resulting stronger transcriptional repression, instead of activation, in OKO HSCs.

Transcriptome Change at the Stage of Skewed Lineage Differentiation

HSC expansion sets the stage for HSC aging but is insufficient to drive phenotypical changes of differentiated cells until the skewing of lineage potential occurs. Therefore, additional gene expression changes may be needed specifically at the stage of lineage determination. To determine these changes and the influence of SIRT1 knockout, Applicants will carry out microarray gene expression analysis of sorted Lin-SP HSCs from $1^{st}$ round BMT recipient mice, at the time that differential blood cell counts exhibit lineage bias. Applicants will confirm by SRY (from male donor cells to female recipients) and knockout cassette genotyping that mice are fully reconstituted by the donor cells. Applicants will isolate Lin– SP cells from 4 mice each receiving BMT from YWT, OWT and OKO mice. RNA of sorted SP cells from each mouse will be extracted with Arcturus PicoPure RNA Isolation kit. After RNA quality control checked by Agilent Bioanalyzer, it will be amplified by WT-Ovation One-Direct RNA Amplification System (NuGEN). After quality control, amplified cDNA will be used for Affymetrix Mouse Genome 430 2.0 array analysis. The genes and pathways identified will be cross-examined with those found at the stage of HSC expansion in Applicants' study to sort out unique genes and pathways for skewing of lineage potential, and the effect of SIRT1 gene knockout. Applicants will validate expression of key genes by real-time PCR, and/or by flow cytometry analysis of the proteins if appropriate antibodies are available.

ChIP-Seq Analysis

Analysis of epigenomics in small number of HSCs has been historically difficult. ChIP-on-chip typically requires ≥1 μg DNA for successful analysis, and with optimization, it can be used to analyze 100,000 cells in the study of epigenomic imprinting of mouse germ cells (Singh, P. et al., *Mol Cell Biol* 31, 1757-1770 (2011); Singh, P. & Szabo, P. E., *Methods Mol Biol* 925, 159-172 (2012)). ChIP-seq requires about 10 ng immunoprecipitated DNA, and is much more sensitive. ChIP-seq allowed a previous study of 20,000 flow-cytometry sorted Lin-Sca1$^+$c-Kit$^+$ hematopoietic progenitor cells. (Adli, M. et al., *Nat Methods* 7, 615-618 (2010)) Most recently, combination of a modified small scale ChIP with deep sequencing has made possible epigenomic profiling of as low as 1000 cells. (Ng, J. H. et al., *Dev Cell* (2013)) The Applicants have developed a robust and routine ChIP assay protocol using 50,000 cells in a small volume setting, (Chen, W. Y. & Townes, T. M., *Proc Natl Acad Sci USA* 97, 377-382 (2000)) similar to the one employed by the study using 1000 cell ChIP-seq. (Ng, J. H. et al., *Dev Cell* (2013)) Applicants will combine small scale ChIP with the optimal library amplification protocol developed by Adli et al (Adli, M. et al., *Nat Methods* 7, 615-618 (2010)) for ChIP-seq of SP HSCs.

Applicants will first perform profiling of H3K4Me3 and H3K27Me3 of SP HSCs from YWT mice. Briefly, bone marrow cells collected from 15 YWT mice will be pooled, and purified Lin-SP cells will be divided into four doses, 20,000, 10,000, 5,000 and 2,000 cells, to determine the lowest optimal doses for ChIP-seq. After fixation with formaldehyde, cells will be lysed in 1% SDS buffer by freeze/thaw cycle. Nuclei will be collected and resuspended in 100 μl 0.1% SDS buffer and sheared by sonication on ice using a microprobe on Misonix S4000. Fragmented chromatin will be transferred to a 0.5 ml glass vial and pre-cleared with protein-A agarose bead. Immunoprecipitation will then be carried out with overnight incubation with H3K4Me3 and H3K27Me3 antibodies, followed by pull down with protein A-agarose bead. Eluted DNA will be reverse crosslinked, followed by treatment with RNase A, proteinase K and phenol:chloroform extraction as described before. (Chen, W. Y. & Townes, T. M., *Proc Natl Acad Sci USA* 97, 377-382 (2000)) To normalize ChIP variation among the genome regions and reduce false peak-calling, crosslinked and sonicated whole cell DNA will be reverse-crosslinked and purified for control in the same way except for IP. DNA will then be primed with a universal random primer containing a restriction site for BciVI as described (Adli, M. et al., *Nat Methods* 7, 615-618 (2010)). The product from the priming reaction will be PCR amplified for 15 cycles, followed by BciVI digestion to create 3' adenine overhang for ligation to Illumina adapters as described. (Adli, M. et al., *Nat Methods* 7, 615-618 (2010)) The ligation product is then PCR amplified for 18 cycles using standard Illumina primers to make a library for sequencing on Illumina Genome HiSeq 2000. Quality of amplified DNA will be assessed by Agilent Bioanalyzer and real-time PCR using primers described. (Adli, M. et al., *Nat Methods* 7, 615-618 (2010))

ChIP-seq data will be aligned to mouse reference genome (UCSC, mm9) using Bowtie aligner (Langmead, B. et al., *Genome Biol* 10, R25 (2009)) allowing maximum 2 mismatches. Reads mapped to more than one position in the genome will be excluded. DNA regions that are bound by H3K3Me3 will be identified by MACS (Zhang, Y. et al., *Genome Biol* 9, R137 (2008)) with default settings. FDR will be controlled at 5%. For H3K27Me3, a sliding window approach will be implemented similar to that described before. (Adli, M. et al., *Nat Methods* 7, 615-618 (2010)) The enriched regions showing at least 2-fold difference between the cells will be considered differentially modified. Applicants will compare H3K4Me3 and H3K27Me3 profiling of SP HSCs with that of Lin-Sca1$^+$c-Kit$^+$ cells (Adli, M. et al., *Nat Methods* 7, 615-618 (2010)), which should yield large similarity.

Applicants will then set to elucidate SIRT1 regulation of transcriptome in HSC aging. Applicants will carry out ChIP-seq to identify SIRT1, LSD1, and Ku70 binding on the genome loci that may correspond to transcriptional changes. Applicants will also perform ChIP-seq for three histone marks, H4K16Ac and H3K4Me2 affected by SIRT1 and LSD1 recruitment, respectively, and repressive mark H3K27Me3. Applicants will harvest Lin-SP HSCs from all 4 legs and spine of each animal for the maximal yield (typically about 3000 to 4000 cells from one YWT mouse, and more than 10,000 cells from an OWT mouse). Because ChIP-seq of HSCs from individual mouse remains challenging, Applicants will carry out the study more conservatively. Applicants will pool SP cells from 2 (for OWT) to 5 (for YWT & OKO) mice, aiming to have 20,000 SP HSCs for each ChIP reaction. Less cells may be used if Applicants will be successful in performing more sensitive ChIP-seq as described above. ChIP-seq will be carried out on both the stage of HSC expansion (original mice) and the stage of lineage skewing ($1^{st}$ round BMT mice).

Applicants will cross-examine ChIP-seq data with microarray expression data to identify the targeted gene regulation by SIRT1/LSD1/Ku70 at both stages of HSC expansion and lineage skewing. Applicants will also identify histone mark changes in the gene regulatory regions during HSC aging and in response to SIRT1 knockout. Those important genes in each stage of HSC aging, such as OXPHOS and TGFβ pathway genes will be carefully examined.

Validation Assays for ChIP-Seq.

To functionally validate that SIRT1 competition with LSD1 for chromatin binding is crucial for regulating HSC aging, Applicants will knockdown LSD1 in aging bone marrow cells of SIRT 1 knockout mice for serial BMT study. Bone marrow cells will be harvested and placed in growth factor medium for transduction/transplantation as Applicants described before. (Yuan, H. et al., Blood 119, 1904-1914 (2012)) Cells will be transduced by two-round infection with lentiviral shLSD1 and control scrambled shRNA. Cells will then be sorted for expression of green fluorescent protein (GFP) expressed from the vector, and equal number of mononuclear cells will be transplanted into lethally irradiated BALB/c mice. For comparison, Applicants will also perform the same transduction/transplantation procedure on old wild type bone marrow cells using scrambled shRNA. Recipient mice will be monitored through aging course and peripheral blood will be examined periodically for lineage change. Mouse bone marrow cells will be analyzed at sacrifice. If no significant phenotypic changes are observed in the first year, secondary BMT may be performed and followed similarly.

To validate that Ku70 may regulate alternating recruitment of SIRT1/LSD1 in transcriptional control, Applicants will examine the direct Ku70 binding to the regulatory sequences of the top-listed candidate genes from ChIP-Seq showing increased LSD1 binding and reduced H3K4Me2 upon SIRT1 knockout. The regulatory sequence will be subcloned to pBluescript vector. In vitro DNaseI footprinting of circular plasmids with recombinant Ku70 protein will then be performed using a standard protocol as described (Giffin, W. et al., Nature 380, 265-268 (1996)).

Characterization of Epigenetic Regulation of Genetic Lesion Accumulation Affecting HSC Aging.

Whereas dysregulation of transcriptome contributes to HSC aging, accumulation of genetic lesions is equally important for functional decline of aging HSCs. (Rossi, D. J. et al., Cell 132, 681-696 (2008)) While point mutations in codons affect protein functions, DNA insertion and deletion (Indel) on regulatory sequences as well as gene duplication and chromosomal loss can result in changes of gene expression. Aged HSCs accrue considerable DNA damage illustrated by yH2AX staining. (Rossi, D. J. et al., Nature 447, 725-729 (2007)) Multiple DNA repair mechanisms are involved in HSC maintenance. (Rossi, D. J. et al., Nature 447, 725-729 (2007); Nijnik, A. et al., Nature 447, 686-690 (2007)) In quiescent HSCs, NHEJ repair plays a prominent role in DNA repair but may inadvertently promote mutagenesis. (Mohrin, M. et al., Cell stem cell 7, 174-185 (2010)) Genome sequencing further reveals that certain genetic mutations have been accumulated in normal hematopoietic progenitor cells and are subsequently "captured" to cooperate with oncogenic events for malignant transformation and leukemogenesis. (Welch, J. S et al., Cell 150, 264-278 (2012)) But, whether mutation acquisition of aging HSCs can be regulated epigenetically is not known. Applicants have shown that SIRT1 promotes acquisition of genetic mutations in CML and prostate cancer cells for drug resistance in response to therapeutic stress and DNA damage, which is in association with its ability to enhance error-prone NHEJ repair through deacetylating Ku70. (Wang, Z. et al., Oncogene 32, 589-598 (2013)) Applicants' preliminary data support that mutation acquisition and DNA repair in CML cells can be regulated by epigenetic factors SIRT1 and LSD1, either through affecting Ku70, through local chromatin architecture, or both. Aging cells also suffer aberrant DNA repair with compromised fidelity, (Seluanov, A. et al., Proc Natl Acad Sci USA 101, 7624-7629 (2004)) which may predispose them to similar mutation acquisition process seen in cancer cells.

Genome-wide Analysis of Genetic Lesions in Aging HSCs.

We will sequence YWT, OWT and OKO HSCs in mice undergoing physiological aging, as well as the $1^{st}$ round BMT recipients at the time when they exhibit skewed lineage differentiation. Applicants aim to collect at least 100 ng genomic DNA (about 16,000 cells) for each sequencing. Purified Lin-HSCs from 2 to 5 YWT, OWT and OKO mice will be pooled, respectively, as described herein. Briefly, genomic DNA will be extracted and fragmented by sonication. After blunting, DNA fragments will be ligated with Illumina adapters. Fragments with approximately 200-250 by insert DNA will be selected and amplified to make a library. After purification, the library will be sequenced for paired-end 100 bp×2 using Illumina Genome HiSeq 2000.

The paired-end sequences will be aligned to mouse reference genome using Novoalign (http://www.novocraft.com). The reads aligned to unique genomic locations are piled up using Samtools v0.1.12. SNPs will be detected using VarScan V2.0. (Koboldt, D. C. et al., Genome Res 22, 568-576 (2012)) The subsequent analysis will be done using a custom developed bioinformatics pipeline implemented using R and Java. SNPs that are present in the YWT cells will be filtered out, and SNPs that are missense, nonsense or affecting splicing sites will be kept for further analysis. For copy number variations, the average coverage of each 10-kb non-overlapping window in the genome in OWT and OKO cells will be compared to the YWT cells to calculate the log 2 ratio to reflect the copy number difference. The copy number variations are detected by DNAcopy's CBS algorithm (http://www.bioconductor.org/packages/2.10/bioc/html/DNAcopy.html). For insertion and deletion (indel) detection, Applicants will use Pindel (Ye, K. et al., Bioinformatics 25, 2865-2871 (2009)) on the combined reads of old and young cells, and indels specific to old cells will be selected. For detecting other types of structural variation, e.g. translocation and inversion, BreakDancer (Chen, K. et al., Nat Methods 6, 677-681 (2009)) will be used. By comparing sequencing data, Applicants will identify the types of genetic mutations or lesions at the stage of HSC expansion versus those at the stage of lineage skewing, and how SIRT1 knockout affects these lesions. Applicants will use conventional DNA sequencing to confirm key new mutations, and use PCR to confirm top candidate deletion or insertion.

Recent studies have suggested that the mutation rates across genome are non-random, (Martincorena, I. et al., Nature 485, 95-98 (2012)) and affected by chromatin organization. (Schuster-Bockler, B. & Lehner, B., Nature 488, 504-507 (2012)) Applicants will cross-examine genome sequencing data with ChIP-seq data to identify epigenomic and genomic environment or domains affecting genetic lesions and the impact of SIRT1 knockout. Applicants will also cross-examine genome sequencing data with array expression data to identify the impact of indels and large genetic alterations on gene expression.

Genome-wide Mutation Analysis of Pathological Conditions from Aged HSCs.

To further enhance the understanding of biological importance of genetic lesions accumulated in aging HSCs and their contribution to diseases, Applicants will sequence two representative malignant progenitor samples, i.e. sorted precursor cells with intermediate B220 and Mac1 expression (see FIG. 4C) and $B220^+Mac1^+$ leukemia cells (see FIG. 4E). Genome sequencing of these cells and data analysis will be performed as described above to identify genetic lesions in malignant progenitors. By cross reference to those lesions found in pre-malignant aging HSCs, Applicants will be able to determine the impact of genetic lesions in aging HSCs on eventual clonal expansion and disease progression.

Effect of LSD1/SIRT1 Competition on Mutation Acquisition.

To functionally validate competitive interaction of SIRT1 and LSD1 on genome wide mutation acquisition in aging HSCs, Applicants will knockdown LSD1 in SIRT1 deficient bone marrow cells for transduction/transplantation assay as described herein. Mice will be followed for the aging course. When mice display the lineage skewing phenotype, Applicants will perform whole genome sequencing of SIRT1-deficient Lin-SP HSCs with mock and LSD1 knockdown. Mutation patterns will be compared to those described herein.

Characterization of Rejuvenation of Aging HSCs by SIRT1 Modulation.

Epigenetics underlines the plasticity of stem cells, and epigenetic reprogramming could reset the aging clock. (Pollina, E. A. & Brunet, A., *Oncogene* 30, 3105-3126 (2011); Rando, T. A. & Chang, H. Y., *Cell* 148, 46-57 (2012)) Aging HSCs can be rejuvenated by inhibition of mammalian target of rapamycin (mTOR), (Chen, C. et al., *Sci Signal* 2, ra75 (2009)) or inhibition of small RhoGTPase Cdc42. (Florian, M. C. et al., *Cell stem cell* 10, 520-530 (2012)) Inhibition of Cdc42 restores acetylation of histone H4K16 in aging HSCs to the level and pattern seen in young HSCs, suggesting that the possible underpinning mechanism for rejuvenation may be epigenetic reprogramming. (Florian, M. C. et al., *Cell stem cell* 10, 520-530 (2012)) Applicants' data further support epigenetic regulation of HSC aging by SIRT1. Although the genetic lesions are impossible to be reversed in aging HSCs, reversing key epigenetic changes could trigger transcriptome reprogramming in aged HSCs and rejuvenate the cells to a certain degree.

Characterization of Rejuvenation of Aging HSCs by SIRT1 Modulation.

The Effect of SIRT1 Knockdown on Rejuvenation of Aging HSCs.

Applicants will test HSC rejuvenation in old (18-22 months) physiologically aging wild type BALB/c mice and aging (12-16 months) $1^{st}$ round BMT recipient mice, to examine the effect of SIRT1 inhibition on two stages of HSC aging. Bone marrow will be harvested and used for lentiviral transduction with shSIRT1 or control scrambled shRNA as described herein. Transduced cells will be sorted for GFP expression, and equal numbers of mononuclear cells will be transplanted into lethally irradiated recipients. For young age mouse control, bone marrow cells from 10-12 week-old BALB/c mice will be similarly transduced by scrambled shRNA, sorted, and used for transplantation. Mice will be analyzed periodically for differential blood cell counts and lineage potential by immunophenotyping as described before. Applicants will sacrifice mice between 8 to 16 months post transplantation and analyze SP HSC frequency and cell cycle, lineage, and CD150 expression. The data will be compared with the profile of young BALB/c transplants. If phenotypic changes would not appear in one year, secondary BMT would be performed and similarly analyzed.

The Effect of Pharmacological Inhibition of SIRT1 on Rejuvenation of Aging HSCs.

Pharmacological inhibition of SIRT1 will be tested in both old (18-22 months) physiologically aging wild type BALB/c mice and aging (12-16 months) $1^{st}$ round BMT recipient mice, with the small molecule inhibitor tenovin-6. (Lain, S. et al., *Cancer Cell* 13, 454-463 (2008)) Mice will be given vehicle or the drug once a day at 50 mg/kg by I.P. injection as Applicants described before (Yuan, H. et al., *Blood* 119, 1904-1914 (2012)) for three weeks. Lineage output in peripheral blood along with other animal health indexes will be monitored and analyzed for two months after cessation of the drug. Then, mice will be sacrificed for analysis of bone marrow SP HSC frequency and cell cycle, lineage, and CD150 expression. The data will be compared with that of normal young BALB/c mice. In addition, bone marrow cells will be transplanted into lethally irradiated recipients to examine if the drug-induced rejuvenation can be transplantable. The recipient mice will be followed for the aging course and similarly examined periodically and at sacrifice.

Epigenomic Changes in Response to HSC Rejuvenation.

To determine if aged HSCs are molecularly rejuvenated, Applicants will perform epigenomic profiling of aged HSCs after SIRT1 inhibition. Applicants will carry out ChIP-seq for H4K16Ac, H3K4me2 and H3K27me3 as described herein, for Lin-SP HSCs with shSIRT1 vs scrambled shRNA, and tenovin-6 vs vehicle treatment.

2. Example II

During B-cell lymphomagenesis, the mechanisms for normal B-cell differentiation and activation are subverted for uncontrolled growth and survival of B-cell lymphomas. Although Epstein-Barr virus is associated with Burkitt lymphoma, the etiology of most of B-cell lymphomas is not clear. (Shaffer, A. L., *Annu Rev Immunol* 30, 565-610 (2012)) Like other cancers, the incidence of lymphomas increases exponentially in the elderly, and the age is one of the most significant contributing factors for lymphomagenesis. (Siegel, R. et al., *CA: a cancer journal for clinicians* 63, 11-30 (2013)) In the elderly, immune competence is highly compromised in both human and mouse (Linton, P. J. & Dorshkind, *Nat Immunol* 5, 133-139 (2004)). In recent years, it is believed that aging of hematopoietic stem cells (HSCs) may contribute to several pathophysiological conditions in the elderly including the decline of immune competence (Linton, P. J. & Dorshkind, *Nat Immunol* 5, 133-139 (2004)), the onset of anemia, and the increased incidence of hematological malignancies. (Lichtman, M. A. & Rowe, J. M., *Semin Oncol* 31, 185-197 (2004)) Aging HSCs exhibit increased cell cycle entry and a skewed differentiation program favoring myeloid lineage. (Morrison, S. J. et al., *Nat Med* 2, 1011-1016 (1996); Pang, W. W. et al., *Proc Natl Acad Sci USA* 108, 20012-20017 (2011)) However, molecular mechanisms of HSC aging and age-related lymphomagenesis are not well understood.

Sirtuins are a family of mammalian NAD-dependent lysine modifying enzymes involved in regulating metabolism, aging and cancer (Roth, M. & Chen, W. Y. *Oncogene* doi:10.1038/onc.2013.120 (2013)). Sirtuin 1 (SIRT1) is a histone/protein deacetylase that regulates gene expression, stress response, DNA damage repair, energy homeostasis and survival of mammalian cells. In 2005, Applicants first reported that SIRT1 is over-expressed in lymphomas in aging $HIC1^{+/-}$ mice (Chen, W. Y. et al., *Cell* 123, 437-448 (2005)). Subsequently, it is shown that SIRT1 expression is associated with poor prognosis of human diffuse large B-cell lymphoma (Jang, K. Y. et al., *The American journal of surgical pathology* 32, 1523-1531 (2008)), and Burkitt lymphoma is sensitive to SIRT1/2 inhibitor cambinol in a single agent (Roth, M. & Chen, W. Y. *Oncogene doi:*10.1038/onc.2013.120 (2013); Heltweg, B. et al., *Cancer Res* 66, 4368-4377 (2006)). SIRT1 over-expression is also found in Hodgkin's lymphoma, in particular, Reed-Sternberg cells (Frazzi, R. et al., *Int J Cancer* 132, 1013-1021 (2013)). However, precise roles of SIRT1 in lymphomagenesis are unknown.

Recently, Applicants have shown that SIRT1 is poorly expressed in normal hematopoietic stem/progenitor cells, but is dramatically up-regulated in response to oncogenic transformation in these cells. SIRT1 activation promotes leukemogenesis mediated by BCR-ABL and enhances survival of chronic myelogenous leukemia stem cells and their resistance to BCR-ABL kinase inhibitors. (Yuan, H. et al., *Blood* 119, 1904-1914 (2012); Li, L. et al., *Cancer Cell* 21, 266-281 (2012)) Applicants also showed that SIRT1 promotes Ku70-mediated nonhomologous end joining DNA damage repair to facilitate acquisition of genetic mutation and cancer cell adaptation for drug resistance. (Wang, Z. et al., *Oncogene* 32, 589-598 (2013)) SIRT1 has been proposed as an anti-aging gene (Roth, M. & Chen, W. Y. *Oncogene* doi:10.1038/onc.2013.120 (2013)). Towards understanding roles of SIRT1 in HSC aging, Applicants carried out serial bone marrow transplantation (BMT) studies in mice. Loss of SIRT1 does not affect hematopoiesis in young adult mice (Chen, W. Y. & Bhatia, R., *Current opinion in hematology* DOI:10.1097/MOH.0b013e328360ab64 (2013)), but surprisingly Applicants found that SIRT1 knockout suppresses mouse HSC aging phenotypes including HSC expansion, skewed lineage differentiation and age-related development of lymphomas and leukemia. SIRT1 knockout helps maintain activation of key molecular regulators for B-cell differentiation and lymphoid output during HSC aging, which may contribute to prevention of age-related mouse lymphomagenesis.

SIRT1 Knockout Inhibited HSC Expansion During Aging.

Applicants used SIRT1 knockout mice that were backcrossed to BALB/c background for HSC aging study since SIRT1 knockout mice are not viable in C57BL/6 background. (Yuan, H. et al., *Blood* 119, 1904-1914 (2012)) Unlike HSCs in C57BL/6 mice, HSCs are less characterized in BALB/c strain. Side population (SP) analysis based on Hoechst dye exclusion is a well-adopted method for HSC analysis in different genetic background. (Goodell, M. A. et al., *Nat Med* 3, 1337-1345 (1997)) Applicants confirmed that in the BABL/c strain, the long-term reconstituting HSCs are exclusively in SP population (not shown). Applicants found that in old wild type (OWT) mice (16-22 months), the HSC pool is expanded significantly as seen in aged C57BL/6 mice, and SIRT1 knockout partially inhibits this age-dependent HSC expansion (FIG. 11). Both old knockout (OKO) and OWT mice had increased myeloid and reduced lymphoid output (not shown), but the lineage analysis of OKO mice was confounded by chronic inflammation involving penile/anile prolapse and ophthalmia-like conditions that may trigger neutrophilic response (not shown). Therefore, serial BMT was used to further examine HSC aging.

SIRT1 Knockout Inhibited Skewed Lineage Differentiation in the 1$^{st}$ Round BMT Recipients.

For easier tracking of serial BMT, Applicants used the following number codes: W—X—Y—Z, W for the age (month) of original donors, X for the age (month) of 1$^{st}$ round BMT recipients, Y for the age (month) of 2$^{nd}$ round BMT recipients, and Z for the age (month) of 3$^{rd}$ round BMT recipients. In 14-8 series (14-month old donors and recipients analyzed at 8 months after BMT), mice receiving wild type bone marrow cells exhibited significant lower total white blood cell and lymphocyte counts in peripheral blood than recipients with SIRT1$^{-/-}$ cells (not shown). In 20-10 series, the skewed lineage differentiation was more significant in some recipients with wild type cells: three out of ten mice exhibited increased myeloid output as compared to recipients with SIRT1$^{-/-}$ cells in which all 16 mice exhibited normal blood phenotypes (FIG. 12A). In line with skewed lineage differentiation, CD150$^+$ SP cells were significantly increased to over 80% in recipients with OWT cells, whereas CD150$^+$ SP cells in mice with OKO cells remained around 60% (FIG. 12B). These results are consistent with the previous report that increased CD150$^+$ SP fraction favors myeloid differentiation during aging, (Challen, G. A. et al., *Cell stem cell* 6, 265-278 (2010)) and show that loss of SIRT1 inhibits skewed lineage differentiation during HSC aging.

SIRT1 Knockout Inhibited Hematological Malignancies in the 2$^{nd}$ and 3$^{rd}$ Round BMT Recipients.

Given that SIRT1 inhibition suppresses development of BCR-ABL mediated leukemogenesis (Yuan, H. et al., *Blood* 119, 1904-1914 (2012)), Applicants' current studies suggest that SIRT1 has a broader role in hematological malignancies, in particular, the age-related spontaneous lymphomas and leukemia.

Molecular Characterization of Aging HSCs and B-Cell Differentiation Defect.

To gain insight into HSC aging, Applicants carried out microarray gene expression analysis of Lin-SP HSCs from young wild type (YWT), OWT and OKO mice. As shown in FIG. 14A, hierarchical clustering of young vs old mice showed that a large number of genes exhibited increased expression in OWT mice. SIRT1 knockout partially restored gene expression pattern to YWT by repressing a large number of activated genes, thus molecularly rejuvenating old HSCs. Applicants used Gene Ontology, Ingenuity Pathways Analysis and gene set enrichment analysis (GSEA) to identify significant pathways involved in HSC aging. Among them, Applicants found that SIRT1 knockout inhibited mitochondrial oxidative phosphorylation (OXPHOS) in old HSCs, including numerous factors for complexes I to IV and ATP synthetase of the electron transport chain (FIG. 13B), but not Krebs cycle genes, suggesting SIRT1 loss may selectively inactivate OXPHOS genes. Increased OXPHOS leads to increased ATP production accompanied by increased generation of reactive oxygen species that have been postulated to increase cellular oxidative stress and DNA damage, and may contribute to HSC aging and increased risk for malignancies. (Rossi, D. J. et al., *Cell* 132, 681-696 (2008)) By real-time RT-PCR, Applicants found that E2A expression was increased in B220$^+$ cells from OKO recipients (FIG. 13C), and strikingly, E2A target genes Ebf1, Pax5 and Rag2 were all inactivated in OWT recipients but remained active in OKO recipients (FIG. 13D). In contrast, SIRT1 knockout did not affect E2A expression and B-cell differentiation in young and middle-age mice (not shown), suggesting SIRT1 affects B-cell differentiation selectively in old HSC-derived cells.

SIRT1 Regulates E2A in Human Cells.

To explore potential roles of SIRT1 in human cells, Applicants knocked down SIRT1 in human B-cell leukemia cell line Sup-15B, and E2A protein level was increased (FIG. 14A). Human E2A is modified by acetylation, which enhances E2A function as described above. To test if SIRT1 may interact with E2A, Applicants co-expressed E2A and flag-SIRT1 in 293 cells, and found that E2A and flag-SIRT1 were co-immunoprecipitated (FIG. 14B), suggesting the likelihood that SIRT1 may regulate E2A functions through protein interaction.

The largest categories of human non-Hodgkin's lymphomas, diffuse large B-cell lymphoma [(germinal center B cell-like (DLBCL-GCB) and activated B cell-like (DLBCL-ABC)] and follicular lymphoma (FL), have medium incidence age of 57 to 66. (Shaffer, A. L., *Annu Rev Immunol* 30, 565-610 (2012)) E2A regulates differentiation and maturation of normal B-cell counterparts of these lymphoma cells (Murre, C., *Nat Immunol* 6, 1079-1086 (2005)). Therefore, Applicants will examine SIRT1 regulation of E2A functions in human cell lines derived from these lymphomas at old ages and compared to lymphoma cells from young ages. Applicants will test Applicants' hypothesis that SIRT1 plays a critical role in controlling B-cell differentiation block in aged human cells, thus affecting lymphomagenesis. This will be achieved by examining SIRT1 deacetylation of E2A to control differentiation.

The SIRT1 Knockdown and E2A Expression.

Applicants will obtain four commercially (DSMZ) available DLBCL-GCB/ABC and FL cell lines derived from old (57-73) individuals: RI-1, HT, NU-DHL-1 and SC-1; and for comparison, two from young (7-17) individuals: DLBCL-GCB line SU-DHL-5 and lymphoblastic lymphoma line U-698-M. SIRT1 knockdown will be carried out in these lines followed by Western analysis of SIRT1 and E2A (E47, a larger splice variant of E2A will be examined and referred to hereafter). E2A expression in the old age group is expected to have better response to the knockdown.

Endogenous SIRT1 and E2A Interaction.

Reciprocal immunoprecipitation (IP) will be carried to examine interaction of endogenous SIRT1 and E2A in old vs young age lymphoma cell lines. Applicants anticipate the stronger interaction in cells from the old age group.

SIRT1 and E2A Acetylation.

Changes of endogenous E2A acetylation will be analyzed by IP and Western blot with pan-acetyl lysine antibody, following SIRT1 knockdown in old vs young age lymphoma cell lines. More pronounced acetylation is expected in old cells. As mentioned above, E2A can be acetylated by acetyltransferase CBP. Applicants will examine if SIRT1 can remove CBP-mediated acetylation by co-expressing an E2A construct with CBP in the presence and absence of a SIRT1 expressing vector in 293 cells, followed by IP and Western analysis.

SIRT1 Regulation of E2A Protein Stability.

E2A Protein half-life will be examined in young and old cells by Western blot following SIRT1 knockdown and then cycloheximide treatment to stop new protein synthesis. Applicants expect SIRT1 inhibition increases E2A half-life selectively in cells from the old age group.

SIRT1 Regulation of E2A Protein Functions.

Applicants will use immunofluorescence to examine E2A protein nuclear localization in young vs old cells following SIRT1 knockdown. Applicants will analyze expression of E2A targets EBF1, PAX5 and RAG2 by real-time RT-PCR and/or Western blot. V(D)J recombination will also be examined by PCR analysis. Applicants expect SIRT1 knockdown increases E2A nuclear localization and expression of target genes, and enhances V(D)J recombination selectively in old cells.

SIRT1 Inhibition on Cell Proliferation and Survival.

Applicants will analyze proliferation and apoptosis of cells after SIRT1 inhibition by shRNA and small molecule inhibitors as before. (Yuan, H. et al., *Blood* 119, 1904-1914 (2012)) Applicants anticipate that proliferation of cells from the old age group will be inhibited more significantly and similarly, more apoptosis will be induced.

To further examine gene expression changes in HSCs, Applicants carried out four-way Venn diagram analysis of the microarray data: up in OWT vs YWT (658 probesets), down in OKO vs OWT (1336 probesets), down in OWT vs YWT (138 probesets), and up in OKO vs OWT (972 probesets). This identified 250 genes that were up in OWT but down with SIRT1 knockout in OKO HSCs (FIG. 38), which represent most of HSC gene expression changes with aging that were reversed by SIRT1 knockout as shown in the hierarchy chart (FIG. 5A).

To more consistently validate expression changes of candidate genes using real-time quantitative RT-PCR, Applicants applied geometric averaging of multiple internal control genesl including β-actin, 18S RNA and CD45. RT-PCR data were processed with the publicly available software REST 2009 (URL: http://www.gene-quantification.com/rest-2009.html), and the relative gene expression levels were presented as Whisker-box plots. As shown in FIG. 39A, significantly increased SIRT1 expression was confirmed in aging HSCs, and the top listed genes Trim26 and Dnmt1 were up in aging HSCs but down with SIRT1 knockout. Dnmt1 regulates cellular DNA methylation and gene expression. Reduction of Dnmt1 results in derepression of genes normally silenced and marked by bivalent chromatin domains in leukemic progenitor cells but not normal HSCs, which leads to suppression of MLL-AF9 mediated leukemogenesis.2 Thus reduction of Dnmt1 expression in OKO HSCs may help suppress leukemogenesis in later stages. Trim26 is also involved in epigenetic regulation of stem cells as further described below. Similarly, SIRT1 knockout reversed or reduced expression of REDOX genes Lrrk2, Ndufa1, Ndufb5, and Aldh1a1 (FIG. 39B). Notably, it has been shown that over-expression of Aldh1a1 promotes myeloid differentiation at the expense of lymphopoiesis, 3 a phenotype consistent with differentiation of aging HSCs in which Aldh1a1 expression is increased. Applicants validated that SIRT1 knockout also reversed expression of HoxA5 and HoxA9 as well as the HoxA cofactor PBX3 (pre-B cell leukemia factor 3) in aging HSCs (FIG. 39C). It is known that increased expression of PBX3/HOXA promotes myeloid leukemogenesis.4 In addition, SIRT 1 knockout reversed or reduced expression of c-Myc, Gsk3b and c-Myb (FIG. 39D). Reduction of these three genes may reduce oncogenic potential of aging HSCs.5-9 The transcriptional factor Tcf3 encoding E2A is upregulated in OKO HSCs (FIG. 39D). Expression of E2A in HSCs promotes maintenance of long term HSCs and development of lymphoid-primed multipotent progenitors.10-12 Increased Tcf3 expression with SIRT1 knockout is consistent with better functions of aging HSCs with the knockout. Therefore, HSC aging may set up a transcriptional program involving multiple genes and pathways that favor myeloid differentiation and leukemogenesis at a very early stage, and SIRT1 knockout reverses or inhibits such a myeloid bias and oncogenic potential and thus improves long term HSC functions during aging.

To investigate potential mechanisms how SIRT1 knockout may reprogram aging HSC transcription, Applicants further examined the E3-ubiquitin ligase tripartite motif-containing (TRIM) protein Trim26, whose expression change is ranked top #2 and validated by RT-PCR (FIGS. 38B and 39A). It has been shown recently that Trim26 is recruited by lysine demethylase Jmjd3 in mouse induced pluripotent stem cells to mediate ubiquitin-dependent degradation of PHF20,13 an epigenome reader that binds dimethylated histone lysines of both active and repressive histone marks.14 Knockout of PHF20 in mice results in defects in multiple hematological organs and lineages, suggesting its potential roles in HSCs.14 Although PHF20 is a cofactor of mixed-lineage leukemia (MLL) H3K34 methyltransferase complex and a component of H4K16 acetyltransferase MOF complex,13,15 the facts that PHF20 can bind dimethylated histone repression marks and that PHF20 knockout does not affect global histone acetylation 14,16 suggest that PHF20 may serve as a cofactor for both transcriptional activation and repression. Accordingly, among 6,209 genes bound by PHF20 genome-wide in mouse induced pluripotent stem cells, only about one third are co-bound by another MLL complex co-activator Wdr5.13 Applicants performed Venn diagram analysis of altered genes in aging mouse HSCs from our microarray data and the data from the published PHF20 binding genes of mouse induced pluripotent stem cells.13 Remarkably, Applicants found that 37% of upregulated genes in aging HSCs and 41% downregulated genes by SIRT1 knockout overlapped with PHF20 target genes, respectively (FIG. 40A, B). Consistently, 36% of the annotated 250-gene list identified in FIG. 38 overlapped with PHF20 targets (FIG. 40C); in contrast, only 12% of the annotated 250-gene list overlapped with PHF20/Wdr5 co-targets (FIG. 40D). Many validated genes described above are among PHF20 targets including Dnmt1, Ndufb5, HoxA5 HoxA9, Pbx3, c-Myc, c-Myb, Tcf3, and Trim26 itself. It is possible that PHF20 normally mediates transcriptional repression of these genes in young HSCs; upon aging, PHF20 is degraded by increased levels of Trim26, leading to transcriptional activation of these PHF20 targets. SIRT1 knockout reduces Trim26, which stabilizes PHF20 and thus restores PHF20 repression of aging-related gene expression in HSCs. Our data suggest that Trim26 may be a novel SIRT1 effector in HSCs through regulating PHF20, which may contribute in part to HSC aging. Additional studies are underway to further illustrate how this novel SIRT1-Trim26-PHF20 pathway operates in aging of hematopoietic stem cells.

V. References

1. Vandesompele, J., De Preter, K., Pattyn, F., Poppe, B., Van Roy, N., De Paepe, A. & Speleman, F. Accurate normalization of real-time quantitative RT-PCR data by geometric averaging of multiple internal control genes. Genome Biol 3, RESEARCH0034 (2002).

2. Trowbridge, J. J., Sinha, A. U., Zhu, N., Li, M., Armstrong, S. A. & Orkin, S. H. Haploinsufficiency of Dnmt1 impairs leukemia stem cell function through derepression of bivalent chromatin domains. Genes Dev 26, 344-349 (2012).

3. Rice, K. L., Izon, D. J., Ford, J., Boodhoo, A., Kees, U. R. & Greene, W. K. Overexpression of stem cell associated ALDH1A1, a target of the leukemogenic transcription factor TLX inhibits lymphopoiesis and promotes myelopoiesis in murine hematopoietic progenitors. Leukemia research 32, 873-883 (2008).

4. Li, Z., Zhang, Z., Li, Y., Arnovitz, S., Chen, P., Huang, H., Jiang, X., Hong, G. M., Kunjamma, R. B., Ren, H., He, C., Wang, C. Z., Elkahloun, A. G., Valk, P. J., Dohner, K., Neilly, M. B., Bullinger, L., Delwel, R., Lowenberg, B., Liu, P. P., Morgan, R., Rowley, J. D., Yuan, C. S. & Chen, J. PBX3 is an important cofactor of HOXA9 in leukemogenesis. Blood 121, 1422-1431 (2013).

5. Slamon, D. J., Boone, T. C., Murdock, D. C., Keith, D. E., Press, M. F., Larson, R. A. & Souza, L. M. Studies of the human c-myb gene and its product in human acute leukemias. Science 233, 347-351 (1986).

6. Siegert, W., Beutler, C., Langmach, K., Keitel, C. & Schmidt, C. A. Differential expression of the oncoproteins c-myc and c-myb in human lymphoproliferative disorders. Eur J Cancer 26, 733-737 (1990).

7. Luscher, B. & Eisenman, R. N. New light on Myc and Myb. Part II. Myb. Genes Dev 4, 2235-2241 (1990).

8. Luscher, B. & Eisenman, R. N. New light on Myc and Myb. Part I. Myc. Genes Dev 4, 2025-2035 (1990).

9. Zhou, F., Zhang, L., van Laar, T., van Dam, H. & Ten Dijke, P. GSK3beta inactivation induces apoptosis of leukemia cells by repressing the function of c-Myb. Molecular biology of the cell 22, 3533-3540 (2011).

10. Dias, S., Mansson, R., Gurbuxani, S., Sigvardsson, M. & Kee, B. L. E2A proteins promote development of lymphoid-primed multipotent progenitors. Immunity 29, 217-227 (2008).

11. Semerad, C. L., Mercer, E. M., Inlay, M. A., Weissman, I. L. & Murre, C. E2A proteins maintain the hematopoietic stem cell pool and promote the maturation of myelolymphoid and myeloerythroid progenitors. Proc Natl Acad Sci USA 106, 1930-1935 (2009).

12. Santos, P. M., Ding, Y. & Borghesi, L. Cell-intrinsic in vivo requirement for the E47-p21 pathway in long-term hematopoietic stem cells. J Immunol 192, 160-168 (2014).

13. Zhao, W., Li, Q., Ayers, S., Gu, Y., Shi, Z., Zhu, Q., Chen, Y., Wang, H. Y. & Wang, R. F. Jmjd3 inhibits reprogramming by upregulating expression of INK4a/Arf and targeting PHF20 for ubiquitination. Cell 152, 1037-1050 (2013).

14. Badeaux, A. I., Yang, Y., Cardenas, K., Vemulapalli, V., Chen, K., Kusewitt, D., Richie, E., Li, W. & Bedford, M. T. Loss of the methyl lysine effector protein PHF20 impacts the expression of genes regulated by the lysine acetyltransferase MOF. J Biol Chem 287, 429-437 (2012).

15. Dou, Y., Milne, T. A., Tackett, A. J., Smith, E. R., Fukuda, A., Wysocka, J., Allis, C. D., Chait, B. T., Hess, J. L. & Roeder, R. G. Physical association and coordinate function of the H3 K4 methyltransferase MLL1 and the H4 K16 acetyltransferase MOF. Cell 121, 873-885 (2005).

16. Adams-Cioaba, M. A., Li, Z., Tempel, W., Guo, Y., Bian, C., Li, Y., Lam, R. & Min, J. Crystal structures of the Tudor domains of human PHF20 reveal novel structural variations on the Royal Family of proteins. FEBS Lett 586, 859-865 (2012).

VI. Embodiments

Embodiment 1. A method of treating or preventing a hematological disease in a subject in need thereof, said method comprising administering a therapeutically effective amount of a SIRT1 inhibitor to a subject, thereby treating or preventing a hematological disease in said subject, wherein said disease is not a cancerous hematological disease.

Embodiment 2. The method of embodiment 1, wherein said hematological disease is an age-related hematological disease.

Embodiment 3. The method of embodiment 1, wherein said method is a method of preventing an age-related hematological disease.

Embodiment 4. The method of embodiment 1, wherein said hematological disease is a red blood cell disease, a lymphoid disease or a myeloid disease.

Embodiment 5. The method of embodiment 4, wherein said red blood cell disease is anemia.

Embodiment 6. The method of embodiment 5, wherein said anemia is age-related anemia.

Embodiment 7. The method of embodiment 4, wherein said lymphoid disease is age-related lymphocytopenia or lymphopenia.

Embodiment 8. The method of embodiment 4, wherein said myeloid disease is a pre-leukemic myeloid disease.

Embodiment 9. The method of embodiment 8, wherein said pre-leukemic myeloid disease is an age-related pre-leukemic myeloid disease.

Embodiment 10. The method of embodiment 9, wherein said pre-leukemic myeloid disease is a myelodysplastic syndrome or a chronic myeloproliferative disease.

Embodiment 11. The method of embodiment 10, wherein said myelodysplastic syndrome is refractory anemia or refractory cytopenia.

Embodiment 12. The method of embodiment 10, wherein said chronic myeloproliferative disease is polycythemia vera or essential thrombocythemia.

Embodiment 13. The method of embodiment 1, wherein said SIRT1 inhibitor is a naphthol inhibitor, an indole inhibitor, a nicotinamide inhibitor, an urea inhibitor, a polyphenol inhibitor, a thienopyrimidine carboxamide inhibitor, inauhzin, a peptide inhibitor or an antisense nucleic acid.

Embodiment 14. The method of embodiment 13, wherein said naphthol inhibitor is sirtinol, cambinol, splitomicin or salermide.

Embodiment 15. The method of embodiment 13, wherein said indole inhibitor is EX-527, bisindolylmaleimide, AC-93253, arylidenindolinone, indolinone, GW5074, RO31-8220 or tryptamine.

Embodiment 16. The method of embodiment 13, wherein said nicotinamide inhibitor is carbanicotinamide adenine dinucleotide.

Embodiment 17. The method of embodiment 13, wherein said urea inhibitor is tenovin or suramin.

Embodiment 18. The method of embodiment 13, wherein said polyphenol inhibitor is biphenylpolyphenol, erbstatin or a rottlerin derivative.

Embodiment 19. The method of embodiment 13, wherein said peptide inhibitor is a thioacetyllysine peptide, a fluoroacetyllysine peptide or a histone-3-lysine-9-thiosuccinyl (H3K9TSu) peptide.

Embodiment 20. A method of increasing immune competence in a subject in need thereof, said method comprising administering a therapeutically effective amount of a SIRT1 inhibitor to a subject, thereby increasing immune competence in said subject.

Embodiment 21. The method of embodiment 20, wherein said subject is an elderly subject.

Embodiment 22. The method of embodiment 20, wherein said SIRT1 inhibitor is a naphthol inhibitor, an indole inhibitor, a nicotinamide inhibitor, an urea inhibitor, a polyphenol inhibitor, a thienopyrimidine carboxamide inhibitor, inauhzin, a peptide inhibitor or an antisense nucleic acid.

Embodiment 23. The method of embodiment 22, wherein said naphthol inhibitor is sirtinol, cambinol, splitomicin or salermide Embodiment 24. The method of embodiment 22, wherein said indole inhibitor is EX-527, bisindolylmaleimide, AC-93253, arylidenindolinone, indolinone, GW5074, RO31-8220 or tryptamine.

Embodiment 25. The method of embodiment 22, wherein said nicotinamide inhibitor is carbanicotinamide adenine dinucleotide.

Embodiment 26. The method of embodiment 22, wherein said urea inhibitor is tenovin or suramin.

Embodiment 27. The method of embodiment 22, wherein said polyphenol inhibitor is biphenylpolyphenol, erbstatin or a rottlerin derivative Embodiment 28. The method of embodiment 22, wherein said peptide inhibitor is a thioacetyllysine peptide, a fluoroacetyllysine peptide or a histone-3-lysine-9-thiosuccinyl (H3K9TSu) peptide.

Embodiment 29. A method of treating or preventing a hematological disease in a subject in need thereof, said method comprising: (i) isolating a hematopoietic stem cell (HSC) from a subject, thereby forming an isolated HSC; (ii) contacting said isolated HSC with a SIRT1 inhibitor, thereby forming a rejuvinated HSC; (iii) administering said rejuvinated HSC to said subject, thereby treating or preventing a hematological disease in said subject.

Embodiment 30. The method of embodiment 29, wherein said the hematological disease is a cancerous hematological disease or a non-cancerous hematological disease.

Embodiment 31. The method of embodiment 29, wherein said rejuvinated HSC is allowed to divide prior to said administering of step (iii).

Embodiment 32. The method of embodiment 29, wherein said isolating comprises obtaining a biological sample from said subject and isolating said HSC from said biological sample.

Embodiment 33. The method of embodiment 32, wherein said biological sample is a blood sample or a bone marrow sample.

Embodiment 34. The method of embodiment 29, wherein said hematological disease is an age-related hematological disease.

Embodiment 35. The method of embodiment 29, wherein said method is a method of preventing an age-related hematological disease.

Embodiment 36. The method of embodiment 29, wherein said hematological disease is a red blood cell disease, a lymphoid disease or a myeloid disease.

Embodiment 37. The method of embodiment 36, wherein said red blood cell disease is anemia.

Embodiment 38. The method of embodiment 37, wherein said anemia is age-related anemia.

Embodiment 39. The method of embodiment 36, wherein said lymphoid disease is acute lymphocytic leukemia, chronic lymphocytic leukemia or lymphoma.

Embodiment 40. The method of embodiment 36, wherein said lymphoid disease is age-related lymphocytopenia or lymphopenia.

Embodiment 41. The method of embodiment 36, wherein said myeloid disease is a pre-leukemic myeloid disease.

Embodiment 42. The method of embodiment 41, wherein said pre-leukemic myeloid disease is an age-related pre-leukemic myeloid disease.

Embodiment 43. The method of embodiment 41, wherein said pre-leukemic myeloid disease is a myelodysplastic syndrome or a chronic myeloproliferative disease.

Embodiment 44. The method of embodiment 43, wherein said myelodysplastic syndrome is refractory anemia or refractory cytopenia.

Embodiment 45. The method of embodiment 43, wherein said chronic myeloproliferative disease is polycythemia vera or essential thrombocythemia.

Embodiment 46. The method of embodiment 36, wherein said myeloid disease is a leukemic myeloid disease.

Embodiment 47. The method of embodiment 46, wherein said leukemic myeloid disease is acute myeloid leukemia, chronic myeloid leukemia, chronic neutrophilic leukemia or chronic eosinophilic leukemia.

Embodiment 48. The method of embodiment 29, wherein said SIRT1 inhibitor is a naphthol inhibitor, an indole inhibitor, a nicotinamide inhibitor, an urea inhibitor, a polyphenol inhibitor, a thienopyrimidine carboxamide inhibitor, inauhzin, a peptide inhibitor or an antisense nucleic acid.

Embodiment 49. The method of embodiment 48, wherein said naphthol inhibitor is sirtinol, cambinol, splitomicin or salermide.

Embodiment 50. The method of embodiment 48, wherein said indole inhibitor is EX-527, bisindolylmaleimide, AC-93253, arylidenindolinone, indolinone, GW5074, RO31-8220 or tryptamine.

Embodiment 51. The method of embodiment 48, wherein said nicotinamide inhibitor is carbanicotinamide adenine dinucleotide.

Embodiment 52. The method of embodiment 48, wherein said urea inhibitor is tenovin or suramin.

Embodiment 53. The method of embodiment 48, wherein said polyphenol inhibitor is biphenylpolyphenol, erbstatin or a rottlerin derivative.

Embodiment 54. The method of embodiment 48, wherein said peptide inhibitor is a thioacetyllysine peptide, a fluoroacetyllysine peptide or a histone-3-lysine-9-thiosuccinyl (H3K9TSu) peptide.

Embodiment 55. A method of forming a red blood cell, said method comprising: (i) contacting a hematopoietic stem cell (HSC) with a SIRT1 inhibitor, thereby forming a rejuvenated HSC; and (ii) allowing said rejuvenated HSC to divide, thereby forming a red blood cell.

Embodiment 56. The method of embodiment 55, wherein said contacting occurs in a subject.

Embodiment 57. The method of embodiment 56, wherein said subject is an elderly subject.

Embodiment 58. The method of embodiment 55, wherein said HSC is derived from a biological sample.

Embodiment 59. The method of embodiment 58, wherein said biological sample is a blood sample or a bone marrow sample.

Embodiment 60. The method of embodiment 55, wherein said contacting occurs in vitro.

Embodiment 61. The method of embodiment 55, wherein after said contacting said rejuvenated HSC is administered to a subject.

Embodiment 62. The method of embodiment 55, wherein said SIRT1 inhibitor is a naphthol inhibitor, an indole inhibitor, a nicotinamide inhibitor, an urea inhibitor, a polyphenol inhibitor, a thienopyrimidine carboxamide inhibitor, inauhzin, a peptide inhibitor or an antisense nucleic acid.

Embodiment 63. The method of embodiment 62, wherein said naphthol inhibitor is sirtinol, cambinol, splitomicin or salermide.

Embodiment 64. The method of embodiment 62, wherein said indole inhibitor is EX-527, bisindolylmaleimide, AC-93253, arylindenindolinone, indolinone, GW5074, RO31-8220 or tryptamine.

Embodiment 65. The method of embodiment 62, wherein said nicotinamide inhibitor is carbanicotinamide adenine dinucleotide.

Embodiment 66. The method of embodiment 62, wherein said urea inhibitor is tenovin or suramin.

Embodiment 67. The method of embodiment 62, wherein said polyphenol inhibitor is biphenylpolyphenol, erbstatin or a rottlerin derivative.

Embodiment 68. The method of embodiment 62, wherein said peptide inhibitor is a thioacetyllysine peptide, a fluoroacetyllysine peptide or a histone-3-lysine-9-thiosuccinyl (H3K9TSu) peptide.

Embodiment 69. A hematopoietic stem cell (HSC) comprising an exogenous SIRT1 inhibitor.

Embodiment 70. The HSC of embodiment 69, wherein said SIRT1 inhibitor is a naphthol inhibitor, an indole inhibitor, a nicotinamide inhibitor, an urea inhibitor, a polyphenol inhibitor, a thienopyrimidine carboxamide inhibitor, inauhzin, a peptide inhibitor or an antisense nucleic acid.

Embodiment 71. The HSC of embodiment 70, wherein said naphthol inhibitor is sirtinol, cambinol, splitomicin or salermide.

Embodiment 72. The HSC of embodiment 70, wherein said indole inhibitor is EX-527, bisindolylmaleimide, AC-93253, arylindenindolinone, indolinone, GW5074, RO31-8220 or tryptamine.

Embodiment 73. The HSC of embodiment 70, wherein said nicotinamide inhibitor is carbanicotinamide adenine dinucleotide.

Embodiment 74. The HSC of embodiment 70, wherein said urea inhibitor is tenovin or surami.

Embodiment 75. The HSC of embodiment 70, wherein said polyphenol inhibitor is biphenylpolyphenol, erbstatin or a rottlerin derivative.

Embodiment 76. The HSC of embodiment 70, wherein said peptide inhibitor is a thioacetyllysine peptide, a fluoroacetyllysine peptide or a histone-3-lysine-9-thiosuccinyl (H3K9TSu) peptide.

What is claimed is:

1. A method of treating or preventing a hematological disease in a subject in need thereof, said method comprising administering a therapeutically effective amount of a SIRT1 inhibitor to a subject, thereby treating or preventing a hematological disease in said subject, wherein said disease is not a cancerous hematological disease, said hematological disease is an age-related hematological disease in an elderly subject and said SIRT1 inhibitor is a naphthol inhibitor, an indole inhibitor, a nicotinamide inhibitor, inauhzin or an antisense nucleic acid.

2. The method of claim 1, wherein said hematological disease is a red blood cell disease, a lymphoid disease or a myeloid disease.

3. The method of claim 2, wherein said red blood cell disease is anemia.

4. A method of increasing immune competence in a subject in need thereof, said method comprising administering a therapeutically effective amount of a SIRT1 inhibitor to a subject, thereby increasing immune competence in said subject, wherein said subject is an elderly subject and said SIRT1 inhibitor is a naphthol inhibitor, an indole inhibitor, a nicotinamide inhibitor, inauhzin or an antisense nucleic acid.

5. A method of treating or preventing a hematological disease in a subject in need thereof said method comprising:
(i) isolating a hematopoietic stem cell (HSC) from a subject, thereby forming an isolated HSC;
(ii) contacting said isolated HSC with a SIRT1 inhibitor, thereby forming a rejuvinated HSC;
(iii) administering said rejuvinated HSC to said subject, thereby treating or preventing a hematological disease in said subject.

6. The method of claim 5, wherein said the hematological disease is a cancerous hematological disease or a non-cancerous hematological disease.

7. The method of claim 5, wherein said rejuvinated HSC is allowed to divide prior to said administering of step (iii).

8. The method of claim 5, wherein said hematological disease is an age-related hematological disease.

9. The method of claim 5, wherein said hematological disease is a red blood cell disease, a lymphoid disease or a myeloid disease.

10. The method of claim 5, wherein said SIRT1 inhibitor is a naphthol inhibitor, an indole inhibitor, a nicotinamide inhibitor, an urea inhibitor, a polyphenol inhibitor, a thienopyrimidine carboxamide inhibitor, inauhzin, a peptide inhibitor or an antisense nucleic acid.

11. A method of forming a red blood cell, said method comprising:

(i) contacting a hematopoietic stem cell (HSC) with a SIRT1 inhibitor, thereby forming a rejuvenated HSC; and
(ii) allowing said rejuvenated HSC to divide, thereby forming a red blood cell, wherein said contacting occurs in an elderly subject and said SIRT1 inhibitor is a naphthol inhibitor, an indole inhibitor, a nicotinamide inhibitor, inauhzin or an antisense nucleic acid.

* * * * *